United States Patent
Bencherif et al.

(10) Patent No.: US 8,846,715 B2
(45) Date of Patent: *Sep. 30, 2014

(54) (2S,3R)-N-(2((3-PYRIDINYL)METHYL)-1-AZABICYCLO[2.2.2]OCT-3-YL)BENZOFURAN-2-CARBOXAMIDE NOVEL SALT FORMS, AND METHODS OF USE THEREOF

(71) Applicant: Targacept, Inc., Winston-Salem, NC (US)

(72) Inventors: Merouane Bencherif, Winston-Salem, NC (US); Lisa Benson, Kernersville, NC (US); Gary Maurice Dull, Lewisville, NC (US); Nikolai Federov, Winston-Salem, NC (US); Gregory J. Gatto, Winston-Salem, NC (US); Kristen G. Jordan, Clemmons, NC (US); Anatoly A. Mazurov, Greensboro, NC (US); Lan Miao, Advance, NC (US); Julio A. Munoz, Walnut Cove, NC (US); Inigo Pfeiffer, Kernersville, NC (US); Sondra Pfeiffer, Kernersville, NC (US); Teresa Phillips, Greensboro, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/947,157

(22) Filed: Jul. 22, 2013

(65) Prior Publication Data

US 2014/0024673 A1    Jan. 23, 2014

Related U.S. Application Data

(63) Continuation of application No. 13/116,080, filed on May 26, 2011, now Pat. No. 8,541,446, which is a continuation of application No. 12/184,312, filed on Aug. 1, 2008, now Pat. No. 7,981,906.

(60) Provisional application No. 60/971,654, filed on Sep. 12, 2007, provisional application No. 60/953,610, filed on Aug. 2, 2007, provisional application No. 60/953,613, filed on Aug. 2, 2007, provisional application No. 60/953,614, filed on Aug. 2, 2007.

(51) Int. Cl.
  C07D 453/02   (2006.01)
  A61K 31/439   (2006.01)
  A61K 45/06    (2006.01)

(52) U.S. Cl.
  CPC ............ *C07D 453/02* (2013.01); *A61K 31/439* (2013.01); *A61K 45/06* (2013.01)
  USPC .......................................... 514/305; 546/133

(58) Field of Classification Search
  CPC ........................... C07D 453/02; A61K 31/439
  USPC .......................................... 514/305; 546/133
  See application file for complete search history.

(56) References Cited

U.S. PATENT DOCUMENTS

| 4,203,990 A | 5/1980 | Yen et al. |
| 4,922,901 A | 5/1990 | Brooks et al. |

(Continued)

FOREIGN PATENT DOCUMENTS

| IN | 173570 | 6/1994 |
| WO | WO 91/12254 A1 | 8/1991 |

(Continued)

OTHER PUBLICATIONS

Wu et al. (SAGE-Hindawi Access to Research, International Journal of Alzheimer's Disease, vol. 2010, Article ID 548913, 11 pages).*

(Continued)

Primary Examiner — Bong-Sook Baek
(74) Attorney, Agent, or Firm — Womble Carlyle Sandridge & Rice, LLP; Amy H. Fix

(57) ABSTRACT

The present invention relates to (2S,3R)—N-(2-((3-pyridinyl)methyl)-1-azabicyclo[2.2.2]oct-3-yl)benzofuran-2-carboxamide, novel salt forms thereof, methods for its preparation, novel intermediates, and methods for treating a wide variety of conditions and disorders, including those associated with dysfunction of the central and autonomic nervous systems.

3 Claims, 19 Drawing Sheets

(56) References Cited

U.S. PATENT DOCUMENTS

| | | | |
|---|---|---|---|
| 4,970,315 | A | 11/1990 | Schmidhalter et al. |
| 5,212,188 | A | 5/1993 | Caldwell et al. |
| 5,217,975 | A | 6/1993 | Wadsworth et al. |
| 5,219,849 | A | 6/1993 | Lotti et al. |
| 5,276,043 | A | 1/1994 | Lippiello et al. |
| 5,346,906 | A | 9/1994 | Baker et al. |
| 5,510,355 | A | 4/1996 | Bencherif et al. |
| 5,583,140 | A | 12/1996 | Bencherif et al. |
| 5,597,919 | A | 1/1997 | Dull et al. |
| 5,604,231 | A | 2/1997 | Smith et al. |
| 5,616,707 | A | 4/1997 | Crooks et al. |
| 5,616,716 | A | 4/1997 | Dull et al. |
| 5,663,356 | A | 9/1997 | Ruecroft et al. |
| 5,712,270 | A | 1/1998 | Sabb |
| 5,811,442 | A | 9/1998 | Bencherif et al. |
| 5,824,692 | A | 10/1998 | Lippiello et al. |
| 5,852,041 | A | 12/1998 | Cosford et al. |
| 5,853,696 | A | 12/1998 | Elmaleh et al. |
| 5,859,004 | A | 1/1999 | Olesen |
| 5,861,423 | A | 1/1999 | Caldwell et al. |
| 5,952,339 | A | 9/1999 | Bencherif et al. |
| 5,969,144 | A | 10/1999 | London et al. |
| 6,432,975 | B1 | 8/2002 | Schmitt et al. |
| 6,734,215 | B2 | 5/2004 | Shytle et al. |
| 6,953,855 | B2 | 10/2005 | Mazurov et al. |
| 7,115,629 | B2 | 10/2006 | Gallemi et al. |
| 7,425,561 | B2 | 9/2008 | Mazurov et al. |
| 2005/0255040 | A1 | 11/2005 | Mazurov et al. |
| 2008/0138287 | A1 | 6/2008 | Mazurov et al. |

FOREIGN PATENT DOCUMENTS

| | | |
|---|---|---|
| WO | WO 94/08992 A1 | 4/1994 |
| WO | WO 95/03306 A1 | 2/1995 |
| WO | WO 96/12711 A1 | 5/1996 |
| WO | WO 96/31475 A2 | 10/1996 |
| WO | WO 96/40682 A1 | 12/1996 |
| WO | WO 97/01556 A1 | 1/1997 |
| WO | WO 97/11072 A1 | 3/1997 |
| WO | WO 97/30998 A1 | 8/1997 |
| WO | WO 98/25619 A1 | 6/1998 |
| WO | WO 98/54181 A1 | 12/1998 |
| WO | WO 99/03859 A1 | 1/1999 |
| WO | WO 99/51602 A1 | 10/1999 |
| WO | WO 99/62505 A2 | 12/1999 |
| WO | WO 00/34276 A1 | 6/2000 |
| WO | WO 01/36417 A1 | 5/2001 |
| WO | WO 01/85727 A1 | 11/2001 |
| WO | WO 02/15662 A2 | 2/2002 |
| WO | WO 02/16356 A2 | 2/2002 |
| WO | WO 02/16357 A2 | 2/2002 |
| WO | WO 02/16358 A2 | 2/2002 |
| WO | WO 02/17358 A2 | 2/2002 |
| WO | WO 02/051841 A1 | 7/2002 |
| WO | WO2004/076449 A | 9/2004 |

OTHER PUBLICATIONS

Arneric, S., et al., "Cholinergic channel modulators as a novel therapeutic strategy for Alzheimer's disease," *Exp. Opin. Invest. Drugs*, 5(1): 79-100 (1996).

Arneric, S., et al., "Preclinical Pharmacology of ABT-418: A Prototypical Cholinergic Channel Activator for the Potential Treatment of Alzheimer's Disease," *CNS Drug Rev.*, 1(1): 1-26 (1995).

Astles, P.C., et al., "Recent progress in the development of subtype selective nicotinic acetylcholine receptor ligands," *Current Drug Targets—CNS & Neurological Disorders*, 1(4): 337-348 (2002).

Bannon, A.W., et al., "Broad-Spectrum, Non-Opioid Analgesic Activity by Selective Modulation of Neuronal Nicotinic Acetylcholine Receptors," *Science*, 279: 77-80 (1998).

Barnes, P.J., "Nuclear Factor-$_k$B," *Int.. J. Biochem. Cell Biol.*, 29 (6): 867-870 (1997).

Bencherif, M., et al., "RJR-2403: A Nicotinic Agonist with CNS Selectivity I: In Vitro *Characterization*," *JPET279*(3), 1413-1421 (1996).

Birtwistle, J., "The role of cigarettes and nicotine in the onset and treatment of ulcerative colitis," *Postgrad. Med. J.*, 72: 714-718 (1996).

CAS Printout for Begue et al., Dec. 1969.

Cas Printout for IN 173 570, Jun. 4, 1994.

Cas Printout for Schmidhalter et al., Nov. 1990.

Chiari, A., et al., "Sex Differences in Cholinergic Analgesia I: A Supplemental Nicotinic Mechanism in Normal Females," *Anesthesiology*, 91(5): 1447-1454 (1999).

Damaj, M.I., et al., "Antinociceptive and Pharmacological Effects of Metanicotine, a Selective Nicotinic Agonist," *J. Phannacol. Exp. Ther.*, 291(1): 390-398 (1999).

Dolle, F., et al., "Synthesis and preliminary evaluation of a carbon-11-labelled agonist of the a-7 nicotinic acetylcholine receptor," *J. Labelled Comp. Radiopharm.* 44: 785-795 (2001).

Dunlop, J., et al., "In vitro screening strategies for nicotinic receptor ligands," *Biochemical Pharmacology*, 74: 1172-1181 (2007).

Ebadi, M., et al., "Neurotrophins and Their Receptors in Nerve Injury and Repair," *Neurochem Int.*, 30(4/5), pp. 347-374 (1997).

Ennaceur, A., et al., "A new one-trial test for neurobiological studies of memory in rats. II: effects of piracetam and pramiracetam," *Behavioural Brain Research*, 33: 197-207 (1989).

Evans, E.A., Isotopic labeling with carbon-14 and tritium, *Principles of Radiopharmacology*, 11-13 (1992).

Freedman, R., et al., "Linkage of a neurophysiological deficit in schizophrenia to a chromosome 15 locus," *Proc. Natl. Acad. Sci.*, 94: 587-592 (1997).

Gavezzotti, Are Crystal Structures Predictable?, Accounts of Chemical Research, vol. 27, pp. 309-314 (1994).

Hanisch, U-K., et al., "Modulation of Hippocampal Acetylcholine Release: A Potent Central Action of Interleukin-2," *The Journal of Neuroscience*, 13(8): 3368-3374 (1993).

Hauser TA, Kucinski A, Jordan KG, Gatto GG, Wersinger SR, Hesse RZ, Stachowiak EK, Stachowiak MK, Lippiello PM, Bencherif M. TC-5619: An alpha7 neuronal nicotinic receptor-selective agonist that ameliorates positive and negative symptoms and enhances cognitive function in animal models of schizophrenia. *Biochem. Phamacol*, Oct. 1, 2009; 78 (7), 803-12.

Heeschen, C., et al., "A novel angiogenic pathway mediated by non-neuronal nicotinic acetylcholine receptors," *J. Clin. Invest.*, 110(4): 527-536 (2002).

Holladay, M.W., et al., "Neuronal Nicotinic Acetylcholine Receptors as Targets for Drug Discovery," *J. Med. Chem.*, 40(26): 4169-4194 (1997).

Hoyer, D. and H.W.G.M. Boddeke, "Partial agonists, full agonists, antagonists: dilemmas of definition," *TiPS Reviews*, 14 270-275 (1993).

International Search Report (PCT/US2004/005044, dated Nov. 3, 2004).

International Search Report (PCT/US2008/071872, dated Dec. 3, 2008).

International Search Report (PCT/US99/19906, dated Jan. 13, 2000).

Jeyarasasingam, G., et al., "Stimulation of Non-a7 Nicotinic Receptors Partially Protects Dopaminergic Neurons from 1-Methyl-4 Phenylpyridinium-Induced Toxicity in Culture," *Neuroscience* 109(2), 275-285 (2002).

Jonakait, G. M., "Neural-immune interactions in sympathetic ganglia," *TINS*, 16(10): 419-423 (1993).

Lavand'homme, P.M., and J.C. Eisenach, "Sex Differences in Cholinergic Analgesia II: Differing Mechanisms in Two Models of Allodynia," *Anethesiology*, 91(5) 1455-1461 (1999).

Leonard, S., et al., "Nicotinic Receptor Function in Schizophrenia," *Schizophrenia Bulletin*, 22(3): 431-445 (1996).

Levin, E.D., and A.H. Rezvani, "Nicotinic Treatment for Cognitive Dysfunction," *Current Drug Targets: CNS and Neurological Disorders*, 1(4): 423-431 (2002).

Levin, E.D., et al., "AR-R17779, an a7 nicotinic agonist, improves learning and memory in rats," *Behavioural Pharmacology*, 10(6/7): 675-780 (1999).

(56) References Cited

OTHER PUBLICATIONS

Macor, J.E., et al., "The 5-HT₃ Antagonist Tropisetron (ICS 205-930) is a Potent and Selective a7 Nicotinic Receptor Partial Agonist," *Bioorg. Med. Chem. Lett.*, 11: 319-321 (2001).

Madretsma, G.S., et al., "Nicotine inhibits the in vitro production of interleukin 2 and tumour necrosis factor-a by human mononuclear cells," *Immunopharmacology*, 35: 47-51(1996).

Madretsma, S., et al., "In-vivo effect of nicotine on cytokine production by human non-adherent mononuclear cells," *European Journal of Gastroenterology & Hepatology*, 8(10): 1017-1020 (1996).

Marrero M, Lucas R, Salet C, Hauser TA, Mazarov A, Lippiello PM, Bencherif M. An Alpha7 Receptor-Selective Agonist Reduces Weight Gain and Metabolic Changes in a Mouse Model of Diabetes. *J Pharmacol Exper Ther Fast Forward* Sep. 28, 2009 ; e-pub.

Matthys, P., et al., "Cytokines and Cachexia," *Nutrition*, 13(9): 763-770 (1997).

Mazurov, A., et al., "Selective a7 Nicotinic Acetylcholine Receptor Ligands," *Current Medical Chemistry*, 13(13): 1567-1584 (2006).

Olesen, P.H., et al., *Bioorganic & Medicinal Chemistry Letters*, 7(15): 1963-1968 (1997).

O'Neill, M.J., et al., "The Role of Neuronal Nicotinic Acetylcholine Receptors in Acute and Chronic Neurodegeneration," *Current Drug Targets: CNS and Neurological Disorders*, 1(4): 399-411 (2002).

Papke, R.L., and J.K.P. Papke, "Comparative pharmacology of rat and human a7 nAChR conducted with net charge analysis," *Brit. J. Pharmacol.*, 137: 49-61 (2002).

Peacock, Mark E., et al., "The Effect of Nicotine on Reproduction and Attachment of Human Gingival Fibroblasts In Vitro," *J. Periodontal*, 64(7): 658-665 (1993).

Placzek, A.N., et al., "An a7 Nicotinic Acetylcholine Receptor Gain-of-Function Mutant that Retains Pharmacological Fidelity," *Molecular Pharmacology*, 68(6): 1863-1876 (2005).

Pullan, Robert D. et al., "Transdermal Nicotine for Active Ulcerative Colitis," *The New England Journal of Medicine*, 330(12): 811-815 (1994).

Pullan, Rupert D., "Colonic mucus, smoking and ulcerative colitis," *Ann R. Coll. Surg Engl.*, 78: 8591 (1996).

Roux, S., et al, "Models for Assessing Antipsychotics: Antagonism of Amphetamine-Induced Hyperactivity and Sterotypies in Mice," *Curr. Protocols in Pharmacol.*, Unit 5.17.1 (1999). —.

Sandbom, W.J., et al., "Nicotine tartrate liquid enemas for mildly to moderately active left-sided ulcerative colitis unresponsive to first-line therapy: a pilot study," *Ailment Pharmacol. Ther.*, 11: 663-671 (1997).

Sartor, R.B., "Pathogenesis and Immune Mechanisms of Chronic Inflammatory Bowel Diseases," *The American Journal of Gastroenterology*, 92(12): 5S-11S (1997).

Schmitt, J.D., "Exploring the Nature of Molecular Recognition in Nicotinic Acetylcholine Receptors," *Curr. Med. Chem.*, 7(8): 749-800 (Aug. 2000).

Sharma, T. and L. Antonova, "Cognitive function in schizophrenia: Deficits, functional consequences, and future treatment," *Psychiatr,. Clin. N. Am.*, 26: 25-40 (2003).

Silverstein, M., et al., "Cigarette Smoking and Ulcerative Colitis: A Case-Control Study," *Mayo Clinic Proc.*, 69: 425-429 (1994).

Stevens, K.E., et al., "Selective a-₇-nicotinic agonists normalize inhibition of auditory response in DBA mice," *Psychopharm.*, 136: 320-327 (1998).

Suemaru, K., et al., Nicotine blocks apomorphine-induced disruption of prepulse inhibition of the acoustic startle in rats: possible involvement of central nicotinic a7 receptors, *British I of Pharmacology*, 142(5): 843-850 (2004).

Tracey, K.J., "The Inflammatory Reflex," *Nature*, 420: 853-859 (2002).

Utsugisawa, K., et al., "Over-expression of a7 nicotinic acetylcholine receptor induces sustained ERK phosphorylation and N-cadherin expression in PC12cells," *Molecular Brain Research*, 106: 88-93 (2002).

Van Dijk, J.P.M., et al., "Nicotine inhibits cytokine synthesis by mouse colonic mucosa." *European Journal of Pharmacology*, 278: R11-R12 (1995).

Villemagne, V.L., et al., "Nicotine and Related Compounds as PET and SPECT Ligands," *Neuronal Nicotinic Receptors Pharmacology and Therapeutic Opportunities*, 235-250 (1999).

Vippagunta et al, "Crystalline Solids", Advanced Drug Delivery Reviews, vol. 48, pp. 3-26 (2001).

Vitti, G., et al., "Synthesis of a Benzo[b]-1,5,-naphtyridine Derivative as a Potential Constrained Nk, Receptor Antagonist," *Tetrahedron Letters*, 35(32): 5939-5942 (1994).

Wallace, J.L., et al., "Inflammatory Mediators in Gastrointestinal Defense and Injury," *Proc. Soc. Exp. Biol. Med.*, 214: 192-203 (1997).

Wang, H., et al., "Nicotinic Acetylcholine Receptor a7 subunit is an Essential Regulator of Inflammation," *Nature*, advance online publication, Dec. 22, 2002: 1-4 (Dec. 2002).

Warawa, E.J., and N.J. Mueller, "Quinuclidine Chemistry. 4' Diuretic Properties of cis-3-Amino-2-benzhythylquinuclidine," *Journal of Medicinal Chemistry*, 18(6): 587-593 (1975).

Williams, M., et al., "Neuronal Nicotinic Acetylcholine Receptors," *Drug News Perspec.*, 7(4): 205223 (1994).

Wu, J., et al., "Roles of nicotinic acetylcholine receptors 13subunits in function of human a4-containing nicotinic receptors," *J. Physiol.* 576.1: 103-118 (2006).

Xiao, H-S., et al., "Identification of gene expression profile of dorsal root ganglion in the rat peripheral axotomy model of neuropathic pain," *Proc. Nat. Acad. Sci.* 99(12): 8360-8365 (2002).

Yanina, et al., *Khim.-Karm*, 21(7): 808-811 (1987).

Zijlstra, F. J. et al., "Effect of nicotine on rectal mucus and mucosal eicosanoids," *Gut*, 35: 247-251 (1994).

Mazurov et al., *2-(Arylmethyl)-3-substituted Quinuclidines as Selective A7 Nicotinic Receptor Ligands*, Bioorganic & Medicinal Chemistry Letters, Pergamon, Elsevier Science, vol. 15, No. 8, Apr. 15, 2005, pp. 2073-2077.

EP Search Report for EP Application No. 11194161 mailed May 23, 2012.

Williams et al. *Foye's Principles of Medicinal Chemistry*, 5th Edition, p. 50, 2002.

\* cited by examiner

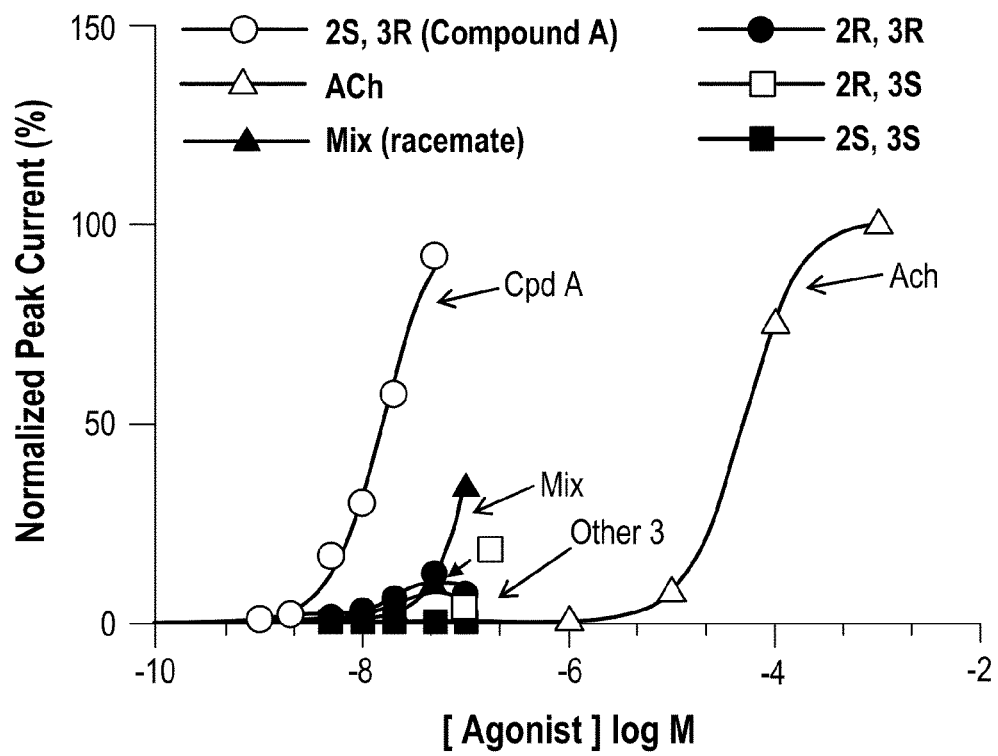
Figure 1A.1
Figure 1A.2

Compound A in a7 rat GH4C1 Cell line
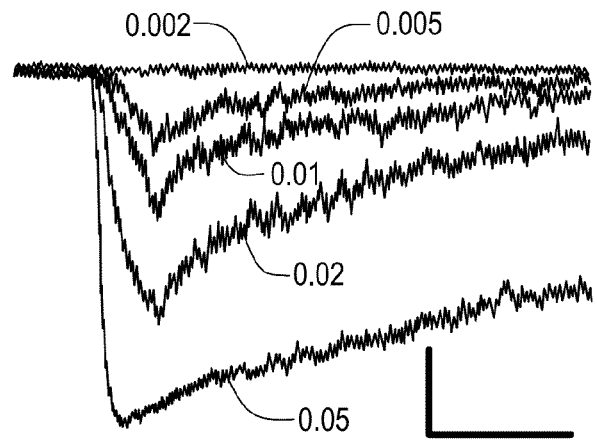
Figure 1A.3
A Ch in a7 rat GH4C1 Cell line
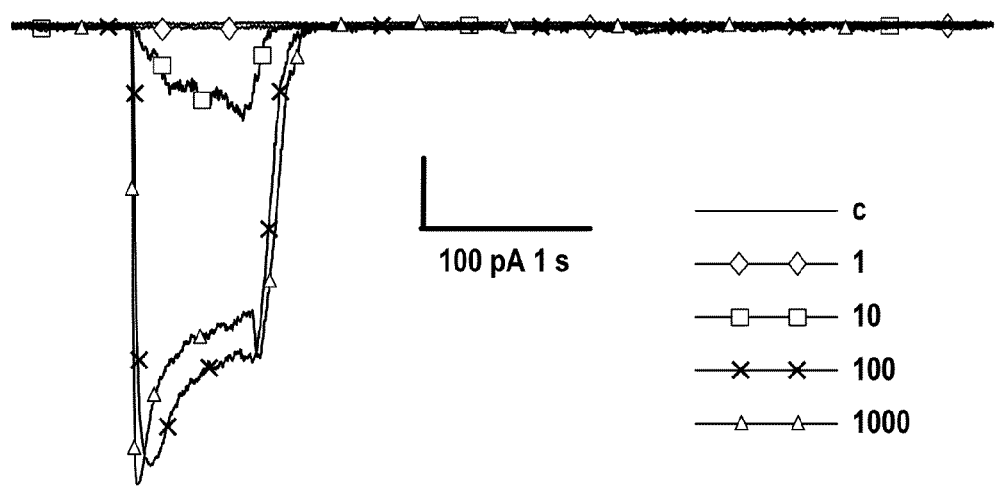
Figure 1A.4

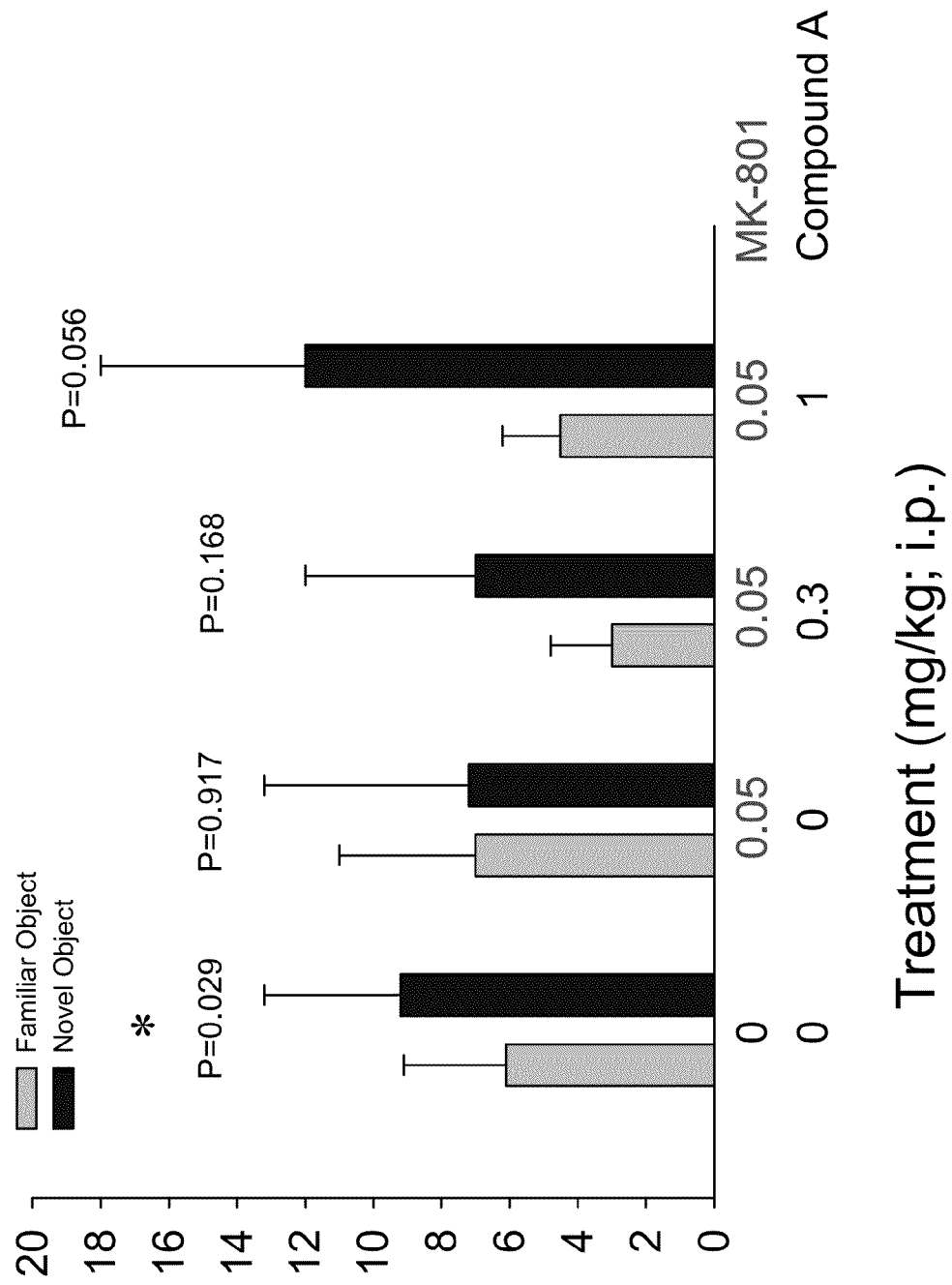

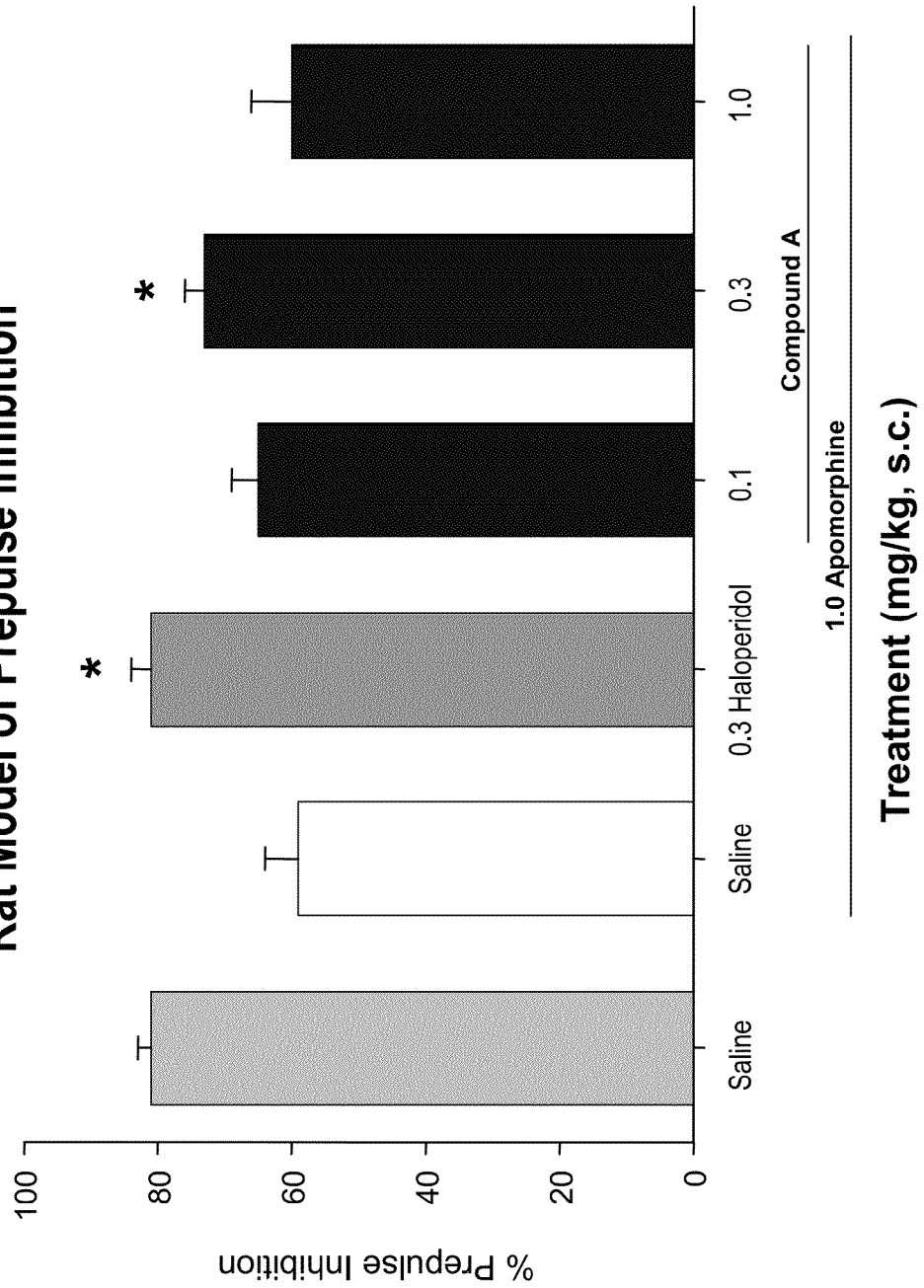

(2S,3R)-N-(2((3-PYRIDINYL)METHYL)-1-AZABICYCLO[2.2.2]OCT-3-YL) BENZOFURAN-2-CARBOXAMIDE NOVEL SALT FORMS, AND METHODS OF USE THEREOF

CROSS RELATION TO PRIOR APPLICATIONS

The present invention is a continuation of U.S. patent application Ser. No. 13/116,080, filed May 26, 2011, which is a continuation of U.S. patent application Ser. No. 12/184,312, filed Aug. 1, 2008, now U.S. Pat. No. 7,981,906 issued Jul. 19, 2011, which claims benefit to U.S. Provisional Application Nos. 60/971,654, filed Sep. 12, 2007, 60/953,610, filed Aug. 2, 2007, 60/953,613, filed Aug. 2, 2007, and 60/953,614 filed Aug. 2, 2007, each of which is incorporated herein by reference in its entirety.

FIELD OF THE INVENTION

The present invention relates to (2S,3R)—N-(2-((3-pyridinyl)methyl)-1-azabicyclo[2.2.2]oct-3-yl)benzofuran-2-carboxamide, novel salt forms thereof, methods for its preparation, novel intermediates, and methods for treating a wide variety of conditions and disorders, including those associated with dysfunction of the central and autonomic nervous systems.

BACKGROUND OF THE INVENTION

The neuronal nicotinic receptors (NNRs) characteristic of the central nervous system (CNS) have been shown to occur in several subtypes, the most common of which are the α4β2 and α7 subtypes. See, for example, Schmitt, *Current Med. Chem.* 7: 749 (2000), herein incorporated by reference. Ligands that interact with the α7 NNR subtype have been proposed to be useful in the treatment of a variety of conditions and disorders. See Mazurov et al., *Curr. Med. Chem.* 13: 1567-1584 (2006) and references therein herein incorporated by reference with regard to background understanding of the α7 neuronal nicotinic receptor subtype. Prominent among those conditions and disorders are cognitive impairment, schizophrenia, inflammation, angiogenesis, neuropathic pain, and fibromyalgia.

There are a decreased number of hippocampal NNRs in postmortem brain tissue of schizophrenic patients. Also, there is improved psychological effect in smoking versus non-smoking schizophrenic patients. Nicotine improves sensory gating deficits in animals and schizophrenics. Blockade of the α7 NNR subtype induces a gating deficit similar to that seen in schizophrenia. See, for example, Leonard et al., *Schizophrenia Bulletin* 22(3): 431 (1996), herein incorporated by reference. Biochemical, molecular, and genetic studies of sensory processing in patients with the P50 auditory-evoked potential gating deficit suggest that the α7 NNR subtype may function in an inhibitory neuronal pathway. See, for example, Freedman et al., *Biological Psychiatry* 38(1): 22 (1995), incorporated by reference.

More recently, α7 NNRs have been proposed to be mediators of angiogenesis, as described by Heeschen et al., *J. Clin. Invest.* 100: 527 (2002), incorporated by reference. In these studies, inhibition of the α7 subtype was shown to decrease inflammatory angiogenesis. Also, α7 NNRs have been proposed as targets for controlling neurogenesis and tumor growth (Utsugisawa et al., *Molecular Brain Research* 106(1-2): 88 (2002) and U.S. Patent Application 2002/0016371, each incorporated by reference). Finally, the role of the α7 subtype in cognition (Levin and Rezvani, *Current Drug Targets: CNS and Neurological Disorders* 1(4): 423 (2002)), neuroprotection (O'Neill et al., *Current Drug Targets: CNS and Neurological Disorders* 1(4): 399 (2002) and Jeyarasasingam et al., *Neuroscience* 109(2): 275 (2002)), and neuropathic pain (Xiao et al., *Proc. Nat. Acad. Sci. (US)* 99(12): 8360 (2002)) has recently been recognized, each citation herein incorporated by reference.

Various compounds have been reported to interact with α7 NNRs and have been proposed as therapies on that basis. See, for instance, PCT WO 99/62505, PCT WO 99/03859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens et al., *Psychopharm.* 136: 320 (1998), Dolle et al., *J. Labelled Comp. Radiopharm.* 44: 785 (2001) and Macor et al., *Bioorg. Med. Chem. Lett.* 11: 319 (2001) and references therein, such references incorporated by reference with regard to background teaching of α7 NNRs and proposed therapies. Among these compounds, a common structural theme is that of the substituted tertiary bicyclic amine (e.g., quinuclidine). Similar substituted quinuclidine compounds have also been reported to bind at muscarinic receptors. See, for instance, U.S. Pat. No. 5,712,270 to Sabb and PCTs, WO 02/00652 and WO 02/051841, each of which is incorporated by reference with regard to such compounds.

A limitation of some nicotinic compounds is that they are associated with various undesirable side effects, for example, by stimulating muscle and ganglionic receptors. There continues to be a need for compounds, compositions, and methods for preventing or treating various conditions or disorders, such as CNS disorders, including alleviating the symptoms of these disorders, where the compounds exhibit nicotinic pharmacology with a beneficial effect, namely upon the functioning of the CNS, but without significant associated side effects. There is a need for compounds, compositions, and methods that affect CNS function without significantly affecting those nicotinic receptor subtypes which have the potential to induce undesirable side effects, such as appreciable activity at cardiovascular and skeletal muscle sites. The present invention provides such compounds, compositions, and methods.

SUMMARY OF THE INVENTION

One aspect of the present invention is (2S,3R)N-(2-((3-pyridinyl)methyl-1-azabicyclo[2.2.2]oct-3-yl)benzofuran-2-carboxamide or a pharmaceutically acceptable salt thereof. Another aspect is (2S,3R)N-(2-((3-pyridinyl)methyl-1-azabicyclo[2.2.2]oct-3-yl)benzofuran-2-carboxamide, in substantially pure form, or a pharmaceutically acceptable salt thereof. A further aspect is (2S,3R)N-(2-((3-pyridinyl)methyl-1-azabicyclo[2.2.2]oct-3-yl)benzofuran-2-carboxamide, substantially free of (2S,3S), (2R,3S), or (2R,3R) isomers, or a pharmaceutically acceptable salt thereof.

Further, another aspect is stereoisomerically enriched (2S,3R)—N-(2-((3-pyridinyl)methyl-1-azabicyclo[2.2.2]oct-3-yl)benzofuran-2-carboxamide, or a pharmaceutically acceptable salt thereof. In one embodiment, the enantiomeric and/or diastereomeric excess is 90% or greater. In one embodiment, the enantiomeric and/or diastereomeric excess is 95% or greater. In one embodiment, the enantiomeric and/or diastereomeric excess is 98% or greater. In one embodiment, the enantiomeric and/or diastereomeric excess is 99% or greater. In one embodiment, the enantiomeric and/or diastereomeric excess is 99.5% or greater.

Another aspect of the present invention is an acid salt of (2S,3R)N-(2-((3-pyridinyl)methyl-1-azabicyclo[2.2.2]oct-3-yl)benzofuran-2-carboxamide, wherein the acid is selected from hydrochloric acid, sulfuric acid, phosphoric acid, maleic acid, p-toluenesulfonic acid, galactaric (mucic) acid, D-mandelic acid, D-tartaric acid, methanesulfonic acid, R— and S-10-camphorsulfonic acids, ketoglutaric acid, or hippuric acid. In one embodiment, the stoichiometry of (2S,3R)—N-(2-((3-pyridinyl)methyl-1-azabicyclo[2.2.2]oct-3-yl)benzofuran-2-carboxamide to the acid is 2:1, 1:1, or 1:2. In one embodiment, the stoichiometry is 1:1. One embodiment of the present invention is (2S,3R)—N-(2-((3-pyridinyl)methyl)-1-azabicyclo[2.2.2]oct-3-yl)benzofuran-2-carboxamide hydrochloride or a hydrate or solvate thereof, including partial hydrates or solvates. A further embodiment is (2S,3R)—N-(2-((3-pyridinyl)methyl)-1-azabicyclo[2.2.2]oct-3-yl)benzofuran-2-carboxamide monohydrochloride or a hydrate or solvate thereof, including partial hydrates or solvates.

The present invention also provides a scalable syntheses of (2S,3R)—N-(2-((3-pyridinyl)methyl)-1-azabicyclo[2.2.2]oct-3-yl)benzofuran-2-carboxamide and novel intermediates.

The scope of the present invention includes all combinations of aspects, embodiments, and preferences herein described.

BRIEF DESCRIPTION OF THE FIGURES

FIGS. 1A1-1A4 illustrate responses of rat α7 receptors expressed in mammalian GH4C1 cells to (2S,3R)—N-(2-((3-pyridinyl)methyl)-1-azabicyclo [2.2.2]oct-3-yl)benzofuran-2-carboxamide; the racemate, namely a mixture of (2S,3R), (2R,3S), (2R,3R), and (2S,3S); the individual stereoisomers; and acetylcholine (ACh).

FIG. 4 illustrates an assessment of cognitive effects in an OR paradigm, demonstrating that (2S,3R)—N-(2-((3-pyridinyl)methyl)-1-azabicyclo [2.2.2]oct-3-yl)benzofuran-2-carboxamide administered p.o. has positive effects over a wide dose range (0.3-10 mg/kg), *p<0.5.

FIGS. 5A and 5B illustrate effects of (2S,3R)—N-(2-((3-pyridinyl)methyl)-1-azabicyclo [2.2.2]oct-3-yl)benzofuran-2-carboxamide administered i.p. in preventing cognitive deficits induced by MK-801, also known as dizocilpine, a commercially available non-competitive antagonist of the NMDA receptor, in the OR task.

FIG. 9 illustrates an antipsychotic assessment, prepulse inhibition, indicating that apomorphine-induced deficits are reversed with pretreatment of (2S,3R)—N-(2-((3-pyridinyl)methyl)-1-azabicyclo [2.2.2]oct-3-yl)benzofuran-2-carboxamide following subcutaneous administration.

DETAILED DESCRIPTION OF THE INVENTION

Figure 1B:
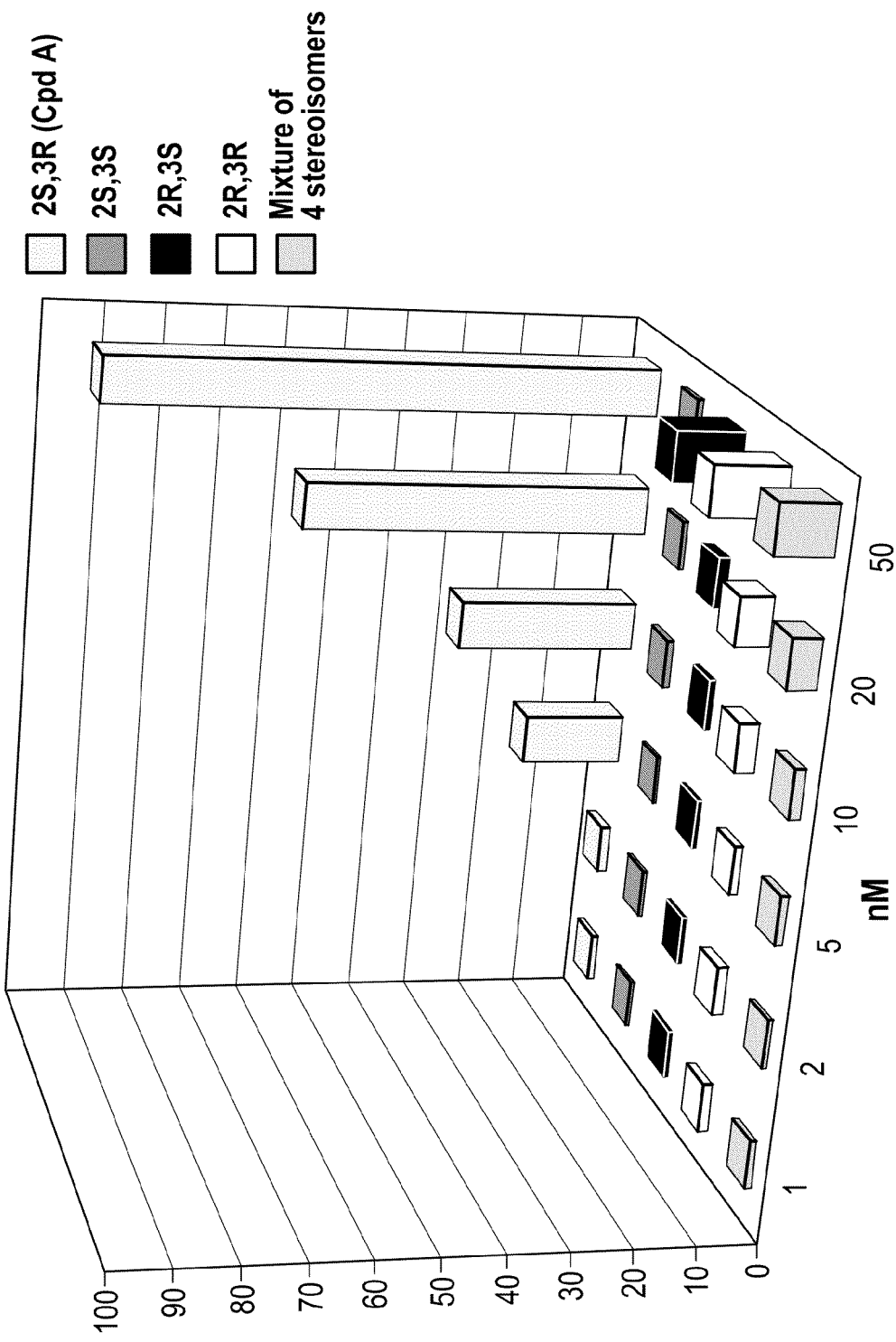
FIG. 1B illustrates a comparison of the functional responses of rat α7 receptors expressed in mammalian GH4C1 cells to (2S,3R)—N-(2-((3-pyridinyl)methyl)-1-azabicyclo [2.2.2]oct-3-yl)benzofuran-2-carboxamide; the racemate, namely a mixture of (2S,3R), (2R,3S), (2R,3R), and (2S,3S); and the individual stereoisomers within the effective plasma concentration range.
Figure 2A:
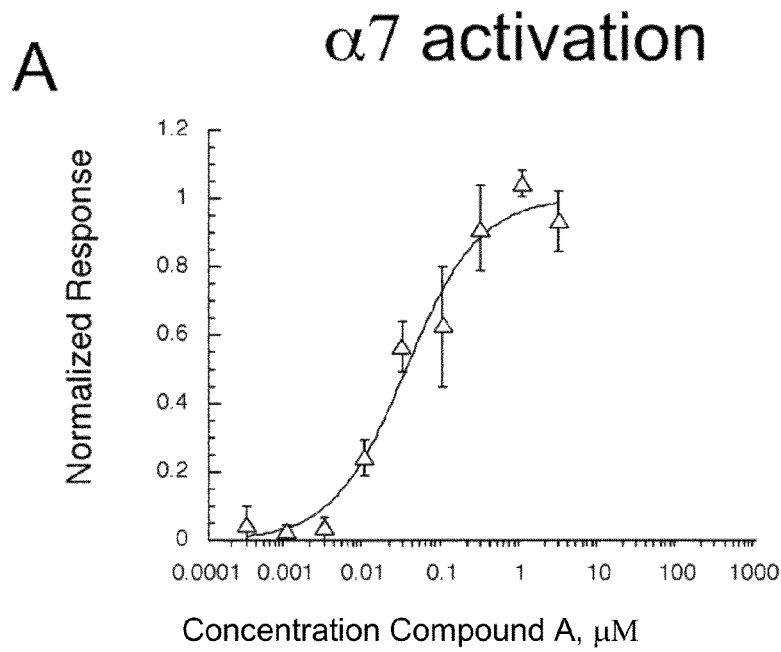
FIG. 2A illustrates responses of human α7 receptors expressed in Xenopus oocytes to (2S,3R)—N-(2-((3-pyridinyl)methyl)-1-azabicyclo [2.2.2]oct-3-yl)benzofuran-2-carboxamide.
Figure 2B:
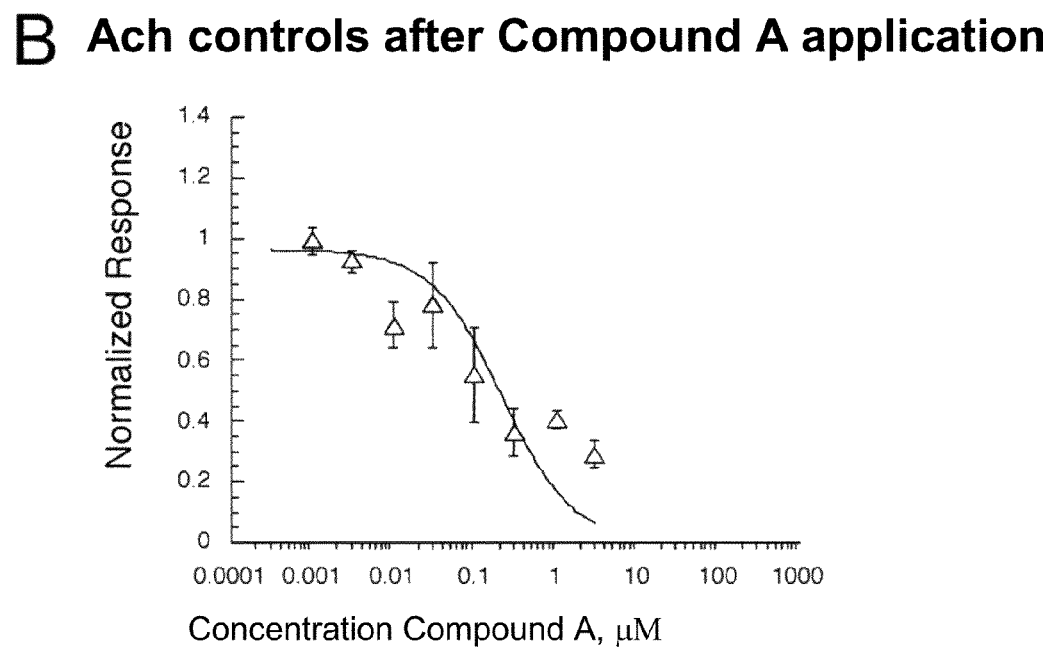
FIG. 2B illustrates control responses of human α7 receptors following the application of the compound at the indicated concentrations. Data were normalized to the net charge of control 300 μM ACh responses obtained 5 min before the experimental agonist-evoked responses. Each point represents the average±SEM of the normalized responses of at least 4 oocytes.

A specific compound, (2S,3R)—N-(2-((3-pyridinyl)methyl)-1-azabicyclo[2.2.2]oct-3-yl)benzofuran-2-carboxamide, with affinity (≤1 nM Ki value) and selective for the α7 NNR subtype demonstrates efficacy in animal models of cognition (cognitive enhancement) and psychosis (anti-psychotic effects).

One aspect of the present invention is (2S,3R)N-(2-((3-pyridinyl)methyl-1-azabicyclo[2.2.2]oct-3-yl)benzofuran-2-carboxamide or a pharmaceutically acceptable salt thereof. Another aspect is (2S,3R)N-(2-((3-pyridinyl)methyl-1-azabicyclo[2.2.2]oct-3-yl)benzofuran-2-carboxamide, in substantially pure form, or a pharmaceutically acceptable salt thereof. A further aspect is (2S,3R)N-(2-((3-pyridinyl)methyl-1-azabicyclo[2.2.2]oct-3-yl)benzofuran-2-carboxamide, substantially free of (2S,3S), (2R,3S), or (2R,3R) isomers, or a pharmaceutically acceptable salt thereof.

Further, another aspect is stereoisomerically enriched (2S,3R)—N-(2-((3-pyridinyl)methyl-1-azabicyclo[2.2.2]oct-3-yl)benzofuran-2-carboxamide, or a pharmaceutically acceptable salt thereof. In one embodiment, the enantiomeric and/or diastereomeric excess is 90% or greater. In one embodiment, the enantiomeric and/or diastereomeric excess is 95% or greater. In one embodiment, the enantiomeric and/or diastereomeric excess is 98% or greater. In one embodiment, the enantiomeric and/or diastereomeric excess is 99% or greater. In one embodiment, the enantiomeric and/or diastereomeric excess is 99.5% or greater.

Another aspect of the present invention is an acid salt of (2S,3R)N-(2-((3-pyridinyl)methyl-1-azabicyclo[2.2.2]oct-3-yl)benzofuran-2-carboxamide, wherein the acid is selected from hydrochloric acid, sulfuric acid, phosphoric acid, maleic acid, p-toluenesulfonic acid, galactaric (mucic) acid, D-mandelic acid, D-tartaric acid, methanesulfonic acid, R— and S-10-camphorsulfonic acids, ketoglutaric acid, or hippuric acid. In one embodiment, the stoichiometry of (2S,3R)—N-(2-((3-pyridinyl)methyl-1-azabicyclo[2.2.2]oct-3-yl)benzofuran-2-carboxamide to the acid is 2:1, 1:1, or 1:2. In one embodiment, the stoichiometry is 1:1. One embodiment of the present invention is (2S,3R)—N-(2-((3-pyridinyl)methyl)-1-azabicyclo[2.2.2]oct-3-yl)benzofuran-2-carboxamide hydrochloride or a hydrate or solvate thereof, including partial hydrates or solvates. A further embodiment is (2S,3R)—N-(2-((3-pyridinyl)methyl)-1-azabicyclo[2.2.2]oct-3-yl)benzofuran-2-carboxamide monohydrochloride or a hydrate or solvate thereof, including partial hydrates or solvates.

Another aspect of the present invention is (2S,3R)-(2-((3-pyridinyl)methyl)-3-amino-1-azabicyclo[2.2.2]octane.

Another aspect of the present invention is a pharmaceutical composition comprising a compound of the present invention and one or more pharmaceutically acceptable carrier.

Another aspect of the present invention is a method for treating or preventing a central nervous system disorder, inflammation, pain, or neovascularization comprising administering a compound of the present invention. In one embodiment, the central nervous system disorder is characterized by an alteration in normal neurotransmitter release. In one embodiment, the central nervous system disorder is selected from mild cognitive impairment, age-associated memory impairment, pre-senile dementia, early onset Alzheimer's disease, senile dementia, dementia of the Alzheimer's type, Alzheimer's disease, Lewy Body dementia, micro-infarct dementia, AIDS-related dementia, HIV-dementia, multiple cerebral infarcts, Parkinsonism, Parkinson's disease, Pick's disease, progressive supranuclear palsy, Huntington's chorea, tardive dyskinesia, hyperkinesia, mania, attention deficit disorder, attention deficit hyperactivity disorder, anxiety, depression, dyslexia, schizophrenia, cognitive dysfunction in schizophrenia, depression, obsessive-compulsive disorders, or Tourette's syndrome. In one embodiment, the central nervous system disorder is selected from Alzheimer's disease, mania, attention deficit disorder, attention deficit hyperactivity disorder, anxiety, dyslexia, schizophrenia, cognitive dysfunction in schizophrenia, depression, obsessive-compulsive disorders, or Tourette's syndrome.

Another aspect of the present invention includes use of a compound of the present invention for the manufacture of a medicament for the treatment or prevention of a central nervous system disorder, inflammation, pain, or neovascularization. In one embodiment, the central nervous system disorder is characterized by an alteration in normal neurotransmitter release. In one embodiment, the central nervous system disorder is selected from mild cognitive impairment, age-associated memory impairment, pre-senile dementia, early onset Alzheimer's disease, senile dementia, dementia of the Alzheimer's type, Alzheimer's disease, Lewy Body dementia, micro-infarct dementia, AIDS-related dementia, HIV-dementia, multiple cerebral infarcts, Parkinsonism, Parkinson's disease, Pick's disease, progressive supranuclear palsy, Huntington's chorea, tardive dyskinesia, hyperkinesia, mania, attention deficit disorder, attention deficit hyperactivity disorder, anxiety, depression, dyslexia, schizophrenia, cognitive dysfunction in schizophrenia, depression, obsessive-compulsive disorders, or Tourette's syndrome. In one embodiment, the central nervous system disorder is selected from Alzheimer's disease, mania, attention deficit disorder, attention deficit hyperactivity disorder, anxiety, dyslexia, schizophrenia, cognitive dysfunction in schizophrenia, depression, obsessive-compulsive disorders, or Tourette's syndrome.

Another aspect of the present invention is a compound of the present invention for use in the treatment or prevention of a central nervous system disorder, inflammation, pain, or neovascularization. In one embodiment, the central nervous system disorder is characterized by an alteration in normal neurotransmitter release. In one embodiment, the central nervous system disorder is selected from mild cognitive impairment, age-associated memory impairment, pre-senile dementia, early onset Alzheimer's disease, senile dementia, dementia of the Alzheimer's type, Alzheimer's disease, Lewy Body dementia, micro-infarct dementia, AIDS-related dementia, HIV-dementia, multiple cerebral infarcts, Parkinsonism, Parkinson's disease, Pick's disease, progressive supranuclear palsy, Huntington's chorea, tardive dyskinesia, hyperkinesia, mania, attention deficit disorder, attention deficit hyperactivity disorder, anxiety, depression, dyslexia, schizophrenia, cognitive dysfunction in schizophrenia, depression, obsessive-compulsive disorders, or Tourette's syndrome. In one embodiment, the central nervous system disorder is selected from Alzheimer's disease, mania, attention deficit disorder, attention deficit hyperactivity disorder, anxiety, dyslexia, schizophrenia, cognitive dysfunction in schizophrenia, depression, obsessive-compulsive disorders, or Tourette's syndrome.

In the above-mentioned methods and uses, in one embodiment of the invention the effective does is between about 1 mg and 10 mg per 24-hour period.

Another aspect of the present invention is a method for manufacturing (2S,3R)—N-(2-((3-pyridinyl)methyl-1-azabicyclo[2.2.2]oct-3-yl)benzofuran-2-carboxamide or a pharmaceutically acceptable salt thereof by sequential dynamic resolution and stereoselective reductive amination of (2-((3-pyridinyl)methyl-1-azabicyclo[2.2.2]oct-3-one.

The scope of the present invention includes all combinations of aspects, embodiments, and preferences herein described.

The commercial development of drug candidates involves many steps, including scaling up the chemical synthesis and purification, finding optimal salt forms, and the like. In the formulation of drug compositions, the drug substance is preferably in a form in which it can be conveniently handled and processed. Considerations include commercial viability as well as consistency in manufacturing. Further, in the manufacture of drug compositions, it is important that a reliable, reproducible and constant plasma concentration profile of drug is provided following administration to a patient.

Chemical stability, solid state stability, and "shelf life" of the active ingredients are also very important factors. The drug substance, and compositions containing it, should preferably be capable of being effectively stored over appreciable periods of time, without exhibiting a significant change in the active component's physico-chemical characteristics (e.g. its chemical composition, density, hygroscopicity and solubility). Moreover, it is also important to be able to provide drug in a form which is as chemically pure as possible. These features of the invention are discussed in more detail below.

I. Compounds

The compound of the present invention is (2S,3R)—N(2-((3-pyridinyl)methyl)-1-azabicyclo[2.2.2]oct-3-yl)benzofuran-2-carboxamide, represented as Compound A below, or a pharmaceutically acceptable salt forms of Compound A.

Compound A

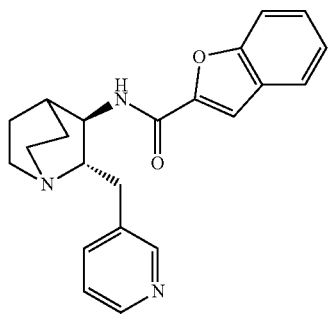

The racemic compound N-(2-((3-pyridinyl)methyl-1-azabicyclo[2.2.2]oct-3-yl)benzofuran-2-carboxamide, a synthesis, and utility in medical treatment, is described in U.S. Pat. No. 6,953,855 to Mazurov et al, herein incorporated by reference.

Racemic N-(2-((3-pyridinyl)methyl-1-azabicyclo[2.2.2]oct-3-yl)benzofuran-2-carboxamide is a high affinity ligand for the α7 subtype of the neuronal nicotinic receptor (N NR). Racemic N-(2-((3-pyridinyl)methyl-1-azabicyclo[2.2.2]oct-3-yl)benzofuran-2-carboxamide contains two asymmetrically substituted carbon atoms. Thus, racemic N-(2-((3-pyridinyl)methyl-1-azabicyclo[2.2.2]oct-3-yl)benzofuran-2-carboxamide occurs in four stereoisomer forms, namely (S,S), (S,R), (R,R), and (R,S). The (S,R), namely (2S,3R), is Compound A.

Previously, it was believed that the predominant stereoisomeric forms produced in the reported synthesis, including U.S. Pat. No. 6,953,855, were characterized by the cis relative configuration at the 2 and 3 positions of the 1-azabicyclo[2.2.2]octane (quinuclidine) ring. In other words, there was an understanding that the cis diastereomer (the (2R,3R) and the (2S,3S) pair of enantiomers), were the predominant forms that resulted when prepared by the reported methods. This determination, of predominantly cis synthesis, was based on: (i) the comparison of $^1$H coupling constants of the 2 and 3 position hydrogen nuclei of the quinuclidine ring and of the isolated diastereomeric (cis and trans) intermediates to the coupling constants reported in the literature; and on (ii) the expected stereochemical outcome of the synthetic chemistry used to produce the compound mixture, by analogy to the literature, with reference to Warawa et al., *J. Med. Chem.* 18(6): 587-593 (1975) and Viti et al., *Letrahedron Lett.* 35(32): 5939-5942 (1994), both of which are incorporated by reference. Thus, there was an expectation that the cis configuration would be formed. As such, the biological testing with the racemate produced results that were presumed attributable to the predominant cis configuration.

It has now been discovered, via x-ray diffraction analysis of crystalline salt forms and analogs, that the predominant diastereomer produced in the original synthesis was, in fact, the trans diastereomer. Furthermore, it has been discovered that the two enantiomers with the trans relative stereochemistry, namely the (2S,3R) and the (2R,3S), differ substantially from one another in their ability to interact with the α7 NNR subtype. The (2S,3R) configuration, Compound A, has greater activity.

With further analysis, it has been discovered that Compound A has pharmacological properties that distinguish it from: i) each of the other three stereoisomers, taken individually; ii) the mixture of all four stereoisomers, namely the racemate; and iii) other α7 NNR ligands reported in the literature.

(2S,3R)—N(2-((3-Pyridinyl)methyl)-1-azabicyclo[2.2.2]oct-3-yl)benzofuran-2-carboxamide (Compound A) is a highly selective, full agonist at the α7 NNR receptor with a remarkably low $EC_{50}$ (for activation) value and a good separation between $EC_{50}$ and the $IC_{50}$ (for residual inhibition), providing functional agonism over a broad range of therapeutically useful concentrations.

II. Scalable Synthesis of (2S,3R)—N-(2-((3-pyridinyl)methyl)-1-azabicyclo[2.2.2]oct-3-yl)benzofuran-2-carboxamide Particular synthetic steps vary in their amenability to scale-up. Reactions are found lacking in their ability to be scaled-up for a variety of reasons, including safety concerns, reagent expense, difficult work-up or purification, reaction energetics (thermodynamics or kinetics), and reaction yield.

The synthesis of (2S,3R)—N-(2-((3-pyridinyl)methyl-1-azabicyclo[2.2.2]oct-3-yl)benzofuran-2-carboxamide described herein has been used to produce kilogram quantities of material, and the component reactions have been carried out on multi-kilogram scale in high yield.

The scalable synthesis utilizes both the dynamic resolution of a racemizable ketone (2-((3-pyridinyl)methyl)-1-azabicyclo[2.2.2]octan-3-one) and the stereoselective reduction of the (R)-α-methylbenzylamine imine derivative (reductive amination) of the resolved ketone.

The synthetic sequences reported herein are readily scalable and avoid chromatographic purifications.

III. Preparation of novel salt forms of (2S,3R)—N-(2-((3-pyridinyl)methyl-1-azabicyclo[2.2.2]oct-3-yl)benzofuran-2-carboxamide (2S,3R)—N-(2-((3-Pyridinyl)methyl-1-azabicyclo[2.2.2]oct-3-yl)benzofuran-2-carboxamide as a free base is an amorphous powder with very limited water solubility. The free base will react with both inorganic and organic acids to make certain acid addition salts that have physical and chemical properties that are advantageous for the preparation of pharmaceutical compositions, including but not limited to crystallinity, water solubility, and stability. The stoichiometry of the salts of the present invention can vary.

Depending upon the manner by which the salts described herein are formed, the salts can have crystal structures that occlude solvents that are present during salt formation. Thus, the salts can occur as hydrates and other solvates of varying stoichiometry of solvent relative to the (2S,3R)—N-(2-((3-pyridinyl)methyl-1-azabicyclo[2.2.2]oct-3-yl)benzofuran-2-carboxamide.

The method for preparing the salt forms can vary. The preparation of (2S,3R)—N-(2-((3-pyridinyl)methyl-1-azabicyclo[2.2.2]oct-3-yl)benzofuran-2-carboxamide salt forms generally involves:
(i) mixing the free base or a solution of the free base, namely (2S,3R)—N-(2-((3-pyridinyl)methyl-1-azabicyclo[2.2.2]oct-3-yl)benzofuran-2-carboxamide in a suitable solvent with an acid neat, or as a solution of an acids in a suitable solvent;
(iia) cooling the resulting salt solution, if necessary to cause precipitation; or
(iib) adding a suitable anti-solvent to cause precipitation; or
(iic) evaporating the first solvent and adding a new solvent and repeating either steps (iia) or step (iib); and
(iii) filtering and collecting the resulting salt.

In one embodiment, the (2S,3R)—N-(2-((3-pyridinyl)methyl-1-azabicyclo[2.2.2]oct-3-yl)benzofuran-2-carboxamide is stereoisomerically enriched. In one embodiment, the enantiomeric and/or diastereomeric excess is 90% or greater. In one embodiment, the enantiomeric and/or diastereomeric excess is 95% or greater. In one embodiment, the enantiomeric and/or diastereomeric excess is 98% or greater. In one embodiment, the enantiomeric and/or diastereomeric excess is 99% or greater. In one embodiment, the enantiomeric and/or diastereomeric excess is 99.5% or greater.

The stoichiometry, solvent mix, solute concentration, and temperature employed can vary. Representative solvents that can be used to prepare or recrystallize the salt forms include, without limitation, ethanol, methanol, isopropyl alcohol, acetone, ethyl acetate, and acetonitrile.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; and salts with amino acids such as aspartate and glutamate. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al, each of which is incorporated by reference.

Salt screening for the free base (2S,3R)—N-(2-((3-pyridinyl)methyl-1-azabicyclo[2.2.2]oct-3-yl)benzofuran-2-carboxamide revealed that, while many salts of pharmaceutically acceptable acids could be formed, only a few of these salts had acceptable properties for commercial manufacture. The ability to predict the characteristics exemplified by a commercially viable salt, therefore, does not exist. Acids that provided salts that were crystalline, namely salts that demonstrate some degree of crystallinity, dependent upon the method by which they are prepared, include hydrochloric acid, sulfuric acid, phosphoric acid, p-toluenesulfonic acid, galactaric (mucic) acid, D-mandelic acid, D-tartaric acid, methanesulfonic acid, R- and S-10-camphorsulfonic acids, maleic acid, ketoglutaric acid and hippuric acid. Of these salts, the hydrochloric acid, phosphoric acid, maleic acid and p-toluenesulfonic acid salts each exhibited additional desirable properties, including high melting points, good water solubility, and low hygroscopicity. These characteristics in these salts were unexpected.

IV. Pharmaceutical Compositions

The pharmaceutical compositions of the present invention include the salts described herein, in the pure state or in the form of a composition in which the compounds are combined with any other pharmaceutically compatible product, which can be inert or physiologically active. The resulting pharmaceutical compositions can be used to prevent a condition or disorder in a subject susceptible to such a condition or disorder, and/or to treat a subject suffering from the condition or disorder. The pharmaceutical compositions described herein include the compound of the present invention and/or pharmaceutically acceptable salts thereof.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Standard excipients include binders, fillers, colorants, solubilizers, and the like. Compositions can be formulated in unit dose form, or in multiple or subunit doses. Preferred compositions are in liquid or semisolid form. Compositions including a liquid pharmaceutically inert carrier such as water or other pharmaceutically compatible liquids or semisolids can be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is the preferred method of injection. Suitable carriers for injection are well known to those of skill in the art and include 5% dextrose solutions, saline, and phosphate-buffered saline. The drug product can also be administered as an infusion or injection (e.g., as a suspension or as an emulsion in a pharmaceutically acceptable liquid or mixture of liquids).

The formulations can also be administered using other means, for example, rectal administration. Formulations useful for rectal administration, such as suppositories, are well known to those of skill in the art. The drug product can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); transdermally (e.g., using a transdermal patch) or iontophoretically; or by sublingual or buccal administration. Although it is possible to administer a compound in the form of a bulk active chemical, it is preferred to present a drug product in the form of a pharmaceutical composition or formulation for efficient and effective administration.

Exemplary methods for administering compounds will be apparent to the skilled artisan. The usefulness of these formulations can depend on the particular composition used and the particular subject receiving the treatment. These formulations can contain a liquid carrier that can be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Other suitable methods for administering the compounds of the present invention are described in U.S. Pat. No. 5,604,231 to Smith et al., the contents of which are hereby incorporated by reference.

In an embodiment of the present invention and as will be appreciated by those skilled in the art, the compound of the present invention may be administered in combination with other therapeutic compounds. For example, a compound of this invention can be used in combination with other NNR ligands (such as varenicline), antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), antipyretics, analgesics, anesthetics (such as used in surgery), acetylcholinesterase inhibitors (such as donepezil and galantamine), antipsychotics (such as haloperidol, clozapine, olanzapine, and quetiapine), immuno-suppressants (such as cyclosporin and methotrexate), neuroprotective agents, steroids (such as steroid hormones), corticosteroids (such as dexamethasone, predisone, and hydrocortisone), vitamins, minerals, nutraceuticals, anti-depressants (such as imipramine, fluoxetine, paroxetine, escitalopram, sertraline, venlafaxine, and duloxetine), anxiolytics (such as alprazolam and buspirone), anticonvulsants (such as phenyloin and gabapentin), vasodilators (such as prazosin and sildenafil), mood stabilizers (such as valproate and aripiprazole), anti-cancer drugs (such as anti-proliferatives), antihypertensive agents (such as atenolol, clonidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole).

The compounds of the present invention may be employed alone or in combination with other therapeutic agents. Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination may be by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The compounds of the present invention may be used in the treatment of a variety of disorders and conditions and, as such, the compounds of the present invention may be used in combination with a variety of other suitable therapeutic agents useful in the treatment or prophylaxis of those disorders or conditions.

The appropriate dose of the compound is that amount effective to prevent occurrence of the symptoms of the disorder or to treat some symptoms of the disorder from which the patient suffers. As noted, by "effective amount", "therapeutic amount" or "effective dose" is meant that amount sufficient to elicit the desired pharmacological or therapeutic effects, thus resulting in effective prevention or treatment of the disorder.

When treating a CNS disorder, an effective amount of compound is an amount sufficient to pass across the blood-brain barrier of the subject, to bind to relevant receptor sites in the brain of the subject and to modulate the activity of relevant NNR subtypes (e.g., provide neurotransmitter secretion, thus resulting in effective prevention or treatment of the disorder). An example of prevention of a disorder is manifested by delaying the onset of the symptoms of the disorder. An example of treatment of a disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate the activity of relevant NNRs, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds described herein, when employed in effective amounts in accordance with the methods described herein, can provide some degree of prevention of the progression of, ameliorate symptoms of, or ameliorate, to some degree, the recurrence of CNS or other disorders. The effective amounts of those compounds are typically below the threshold concentration required to elicit any appreciable side effects, for example those effects relating to skeletal muscle or ganglia. The compounds can be administered in a therapeutic window in which certain CNS and other disorders are treated and certain side effects are avoided. Ideally, the effective dose of the compounds described herein is sufficient to provide the desired effects upon the disorder but is insufficient (i.e., is not at a high enough level) to provide undesirable side effects. Preferably, the compounds are administered at a dosage effective for treating the CNS or other disorders but less than, often less than ⅕, and often less than 1/10, the amount required to elicit certain side effects to any significant degree.

Most preferably, effective doses are at very low concentrations, where maximal effects are observed to occur, with a minimum of side effects. Typically, the effective dose of such compounds generally requires administering the compound in an amount of less than 5 mg/kg of patient weight. Often, the compounds of the present invention are administered in an amount from less than about 1 mg/kg patent weight and usually less than about 100 μg/kg of patient weight, but frequently between about 10 μg to less than 100 μg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 100 mg/24 hr/patient. For human patients, the effective dose of typical compounds requires administering the compound which generally does not exceed about 500, often does not exceed about 400, and frequently does not exceed about 300 mg/24 hr/patient. In addition, the compositions are advantageously administered at an effective dose such that the concentration of the compound within the plasma of the patient normally does not exceed 50 ng/mL, often does not exceed 30 ng/mL, and frequently does not exceed 10 ng/mL. In one embodiment of the present invention, an effective dose is between about 1 mg and 10 mg in a 24-hour period.

IV. Method of Using Pharmaceutical Compositions

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., *Trends Pharmacol. Sci.* 14(7): 270-5 (1993), herein incorporated by reference with regard to such teaching. Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As used herein, neurotransmitters whose release is mediated by the compounds described herein include, but are not limited to, acetylcholine, dopamine, norepinephrine, serotonin, and glutamate, and the compounds described herein function as modulators at the α7 subtype of the CNS NNRs.

As used herein, the terms "prevention" or "prophylaxis" include any degree of reducing the progression of or delaying the onset of a disease, disorder, or condition. The term includes providing protective effects against a particular disease, disorder, or condition as well as amelioration of the recurrence of the disease, disorder, or condition. Thus, in another aspect, the invention provides a method for treating a subject having or at risk of developing or experiencing a recurrence of a NNR or nAChR mediated disorder. The compounds and pharmaceutical compositions of the invention may be used to achieve a beneficial therapeutic or prophylactic effect, for example, in a subject with a CNS dysfunction.

As noted above, the free base and salt compounds of the present invention modulates the α7 NNR subtype, characteristic of the CNS, and can be used for preventing or treating various conditions or disorders, including those of the CNS, in subjects which have or are susceptible to such conditions or disorders, by modulation of the α7 NNR. The compounds have the ability to selectively bind to the α7 NNR and express nicotinic pharmacology, for example, to act as agonists, partial agonists, antagonists, as described.

For example, compounds of the present invention, when administered in effective amounts to patients in need thereof, provide some degree of prevention of the progression of the CNS disorder, namely, providing protective effects, amelioration of the symptoms of the CNS disorder, or amelioration of the reoccurrence of the CNS disorder, or a combination thereof.

The compounds of the present invention can be used to treat or prevent those types of conditions and disorders for which other types of nicotinic compounds have been proposed or are shown to be useful as therapeutics. See, for example, the references previously listed hereinabove, as well as Williams et al., *Drug News Perspec.* 7(4): 205 (1994), Arneric et al., *CNS Drug Rev.* 1(1): 1-26 (1995), Arneric et al., *Exp. Opin. Invest. Drugs* 5(1): 79-100 (1996), Bencherif et al., *J. Pharmacol. Exp. Ther.* 279: 1413 (1996), Lippiello et al., *J. Pharmacol. Exp. Ther.* 279: 1422 (1996), Damaj et al., *J. Pharmacol. Exp. Ther.* 291: 390 (1999); Chiari et al., *Anesthesiology* 91: 1447 (1999), Lavand'homme and Eisenbach, *Anesthesiology* 91: 1455 (1999), Holladay et al., *J. Med. Chem.* 40(28): 4169-94 (1997), Bannon et al., *Science* 279:

77 (1998), PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al., the disclosures of which are incorporated herein by reference with regard to such therapeutic teaching.

The compounds and their pharmaceutical compositions are useful in the treatment or prevention of a variety of CNS disorders, including neurodegenerative disorders, neuropsychiatric disorders, neurologic disorders, and addictions. The compounds and their pharmaceutical compositions can be used to treat or prevent cognitive deficits and dysfunctions, age-related and otherwise; attentional disorders and dementias, including those due to infectious agents or metabolic disturbances; to provide neuroprotection; to treat convulsions and multiple cerebral infarcts; to treat mood disorders, compulsions and addictive behaviors; to provide analgesia; to control inflammation, such as mediated by cytokines and nuclear factor kappa B; to treat inflammatory disorders; to provide pain relief; to treat metabolic disorders such as diabetes or metabolic syndrome; and to treat infections, as anti-infectious agents for treating bacterial, fungal, and viral infections.

CNS Disorders

Among the disorders, diseases and conditions that the compounds and pharmaceutical compositions of the present invention can be used to treat or prevent are: age-associated memory impairment (AAMI), mild cognitive impairment (MCI), age-related cognitive decline (ARCD), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, vascular dementia, Down syndrome, head trauma, traumatic brain injury (TBI), dementia pugilistica, Creutzfeld-Jacob Disease and prion diseases, stroke, ischemia, attention deficit disorder, attention deficit hyperactivity disorder, dyslexia, schizophrenia, schizophreniform disorder, schizoaffective disorder, cognitive dysfunction in schizophrenia, cognitive deficits in schizophrenia such as memory, including working memory, executive function, attention, vigilance, information processing, and learning, dementia (whether mild, moderate or severe) associated with schizophrenia, dementia (whether mild, moderate or severe) associated with schizophrenia, Parkinsonism including Parkinson's disease, postencephalitic parkinsonism, parkinsonism-dementia of Gaum, frontotemporal dementia Parkinson's Type (FTDP), Pick's disease, Niemann-Pick's Disease, Huntington's Disease, Huntington's chorea, tardive dyskinesia, hyperkinesia, progressive supranuclear palsy, progressive supranuclear paresis, restless leg syndrome, multiple sclerosis, amyotrophic lateral sclerosis (ALS), motor neuron diseases (MND), multiple system atrophy (MSA), corticobasal degeneration, Guillain-Barré Syndrome (GBS), chronic inflammatory demyelinating polyneuropathy (CIDP), epilepsy, autosomal dominant nocturnal frontal lobe epilepsy, mania, anxiety, depression, premenstrual dysphoria, panic disorders, bulimia, anorexia, narcolepsy, excessive daytime sleepiness, bipolar disorders, generalized anxiety disorder, obsessive compulsive disorder, rage outbursts, oppositional defiant disorder, Tourette's syndrome, autism, drug and alcohol addiction, tobacco addiction, obesity, cachexia, psoriasis, lupus, acute cholangitis, aphthous stomatitis, ulcers, asthma, ulcerative colitis, inflammatory bowel disease, Crohn's disease, post operative ileus, spastic dystonia, diarrhea, constipation, pouchitis, pancreatitis, viral pneumonitis, arthritis, including, rheumatoid arthritis and osteoarthritis, endotoxaemia, sepsis, atherosclerosis, idiopathic pulmonary fibrosis, acute pain, chronic pain, neuropathies, urinary incontinence, diabetes, and neoplasias.

Cognitive impairments or dysfunctions may be associated with psychiatric disorders or conditions, such as schizophrenia and other psychotic disorders, including but not limited to psychotic disorder, schizophreniform disorder, schizoaffective disorder, delusional disorder, brief psychotic disorder, shared psychotic disorder, and psychotic disorders due to one or more general medical conditions, dementias, and other cognitive disorders, including but not limited to mild cognitive impairment, pre-senile dementia, Alzheimer's disease, senile dementia, dementia of the Alzheimer's type, age-related memory impairment, Lewy body dementia, vascular dementia, AIDS dementia complex, dyslexia, Parkinsonism including Parkinson's disease, cognitive impairment and dementia of Parkinson's Disease, cognitive impairment of multiple sclerosis, cognitive impairment caused by traumatic brain injury, dementias due to other general medical conditions, anxiety disorders, including but not limited to panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder and generalized anxiety disorder due to a general medical condition, mood disorders, including but not limited to major depressive disorder, dysthymic disorder, bipolar depression, bipolar mania, bipolar I disorder, depression associated with manic, depressive or mixed episodes, bipolar II disorder, cyclothymic disorder, and mood disorders due to general medical conditions, sleep disorders, including but not limited to dyssomnia disorders, primary insomnia, primary hypersomnia, narcolepsy, parasomnia disorders, nightmare disorder, sleep terror disorder and sleepwalking disorder, mental retardation, learning disorders, motor skills disorders, communication disorders, pervasive developmental disorders, attention-deficit and disruptive behavior disorders, attention deficit disorder, attention deficit hyperactivity disorder, feeding and eating disorders of infancy, childhood, or adults, tic disorders, elimination disorders, substance-related disorders, including but not limited to substance dependence, substance abuse, substance intoxication, substance withdrawal, alcohol-related disorders, amphetamine or amphetamine-like-related disorders, caffeine-related disorders, *cannabis*-related disorders, cocaine-related disorders, hallucinogen-related disorders, inhalant-related disorders, nicotine-related disorders, opioid-related disorders, phencyclidine or phencyclidine-like-related disorders, and sedative-, hypnotic- or anxiolytic-related disorders, personality disorders, including but not limited to obsessive-compulsive personality disorder and impulse-control disorders.

The symptoms of schizophrenia are generally divided into three categories: Positive, Negative, and Cognitive. Positive Symptoms, may also be referred to as "psychotic" symptoms, and include delusions and hallucinations. "Positive" refers to having overt symptoms. Negative Symptoms include emotional flatness or lack of expression, an inability to start and follow through with activities, speech that is brief and devoid of content, and a lack of pleasure or interest in activities. "Negative" refers to a lack of certain characteristics that would otherwise be present in a healthy individual. Cognitive Symptoms pertain to thinking processes. Cognitive symptoms include cognitive deficits such as memory, including working memory, executive function, attention, vigilance, information processing, and learning, with reference to Sharma et al., *Cognitive Function in Schizophrenia: Deficits, Functional Consequences, and Future Treatment*, Psychiatr. Clin. N. Am. 26 (2003) 25-40, herein incorporated by reference. Schizophrenia also affects mood. While many individuals affected with schizophrenia become depressed, some also have apparent mood swings and even bipolar-like states.

The above conditions and disorders are discussed in further detail, for example, in the American Psychiatric Association: Diagnostic and Statistical Manual of Mental Disorders, Fourth Edition, Text Revision, Washington, D.C., American Psychiatric Association, 2000; incorporated herein by reference with regard to defining such conditions and disorders. This Manual may also be referred to for greater detail on the symptoms and diagnostic features associated with substance use, abuse, and dependence.

Preferably, the treatment or prevention of diseases, disorders, and conditions occurs without appreciable adverse side effects, including, for example, significant increases in blood pressure and heart rate, significant negative effects upon the gastro-intestinal tract, and significant effects upon skeletal muscle.

The compounds of the present invention, when employed in effective amounts, are believed to modulate the activity of the α7 NNR without appreciable interaction with the nicotinic subtypes that characterize the human ganglia, as demonstrated by a lack of the ability to elicit nicotinic function in adrenal chromaffin tissue, or skeletal muscle, further demonstrated by a lack of the ability to elicit nicotinic function in cell preparations expressing muscle-type nicotinic receptors. Thus, these compounds are believed capable of treating or preventing diseases, disorders, and conditions without eliciting significant side effects associated activity at ganglionic and neuromuscular sites. Thus, administration of the compounds is believed to provide a therapeutic window in which treatment of certain diseases, disorders, and conditions is provided, and certain side effects are avoided. That is, an effective dose of the compound is believed sufficient to provide the desired effects upon the disease, disorder, or condition, but is believed insufficient, namely is not at a high enough level, to provide undesirable side effects.

Thus, the present invention provides the use of a compound of the present invention, or a pharmaceutically acceptable salt thereof, for use in therapy, such as a therapy described above.

In yet another aspect the present invention provides the use of a compound of the present invention, or a pharmaceutically acceptable salt thereof, in the manufacture of a medicament for use in the treatment of a CNS disorder, such as a disorder, disease or condition described hereinabove.

Inflammation

The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, "The inflammatory reflex," *Nature* 420: 853-9 (2002), herein incorporated by reference). Excessive inflammation and tumor necrosis factor synthesis cause morbidity and even mortality in a variety of diseases. These diseases include, but are not limited to, endotoxemia, rheumatoid arthritis, osteoarthritis, psoriasis, asthma, atherosclerosis, idiopathic pulmonary fibrosis, and inflammatory bowel disease.

Inflammatory conditions that can be treated or prevented by administering the compounds described herein include, but are not limited to, chronic and acute inflammation, psoriasis, endotoxemia, gout, acute pseudogout, acute gouty arthritis, arthritis, rheumatoid arthritis, osteoarthritis, polymyositis, dermatomyositis, ankylosing spondylitis, Still's disease, adult onset Still's disease, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, pouchitis, glomerulonephritis, lupus nephritis, thrombosis, and graft vs. host reaction.

Inflammatory Response Associated with Bacterial and/or Viral Infection

Many bacterial and/or viral infections (e.g., meningitis, hepatitis and nephritis) are associated with side effects brought on by the formation of toxins, and the body's natural response to the bacteria or virus and/or the toxins. As discussed above, the body's response to infection often involves generating a significant amount of TNF and/or other cytokines. The over-expression of these cytokines can result in significant injury, such as septic shock (when the bacteria is sepsis), endotoxic shock, urosepsis, and toxic shock syndrome.

Cytokine expression is mediated by NNRs, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Examples of such bacterial infections include anthrax, botulism, and sepsis. Some of these compounds may also have antimicrobial properties.

These compounds can also be used as adjunct therapy in combination with existing therapies to manage bacterial, viral, and fungal infections, such as antibiotics, antivirals, and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle et al., incorporated herein by reference. Other agents effective against bacterial and other toxins can be effective and their therapeutic effect can be complemented by co-administration with the compounds described herein.

Pain

The compounds can be administered to treat and/or prevent pain, including acute, neurologic, inflammatory, neuropathic, and chronic pain. The analgesic activity of compounds described herein can be demonstrated in models of persistent inflammatory pain and of neuropathic pain, performed as described in U.S. Published Patent Application No. 20010056084 A1 (Allgeier et al.), incorporated by reference, wherein is demonstrated hyperalgesia in the complete Freund's adjuvant rat model of inflammatory pain and mechanical hyperalgesia in the mouse partial sciatic nerve ligation model of neuropathic pain.

The analgesic effect is suitable for treating pain of various genesis or etiology, in particular in treating inflammatory pain and associated hyperalgesia, neuropathic pain, and associated hyperalgesia, chronic pain (e.g., severe chronic pain, post-operative pain, and pain associated with various conditions including cancer, angina, renal or biliary colic, menstruation, migraine, and gout). Inflammatory pain may be of diverse genesis, including arthritis and rheumatoid disease, tenosynovitis, and vasculitis. Neuropathic pain includes trigeminal or herpetic neuralgia, diabetic neuropathy pain, causalgia, low back pain, and deafferentation syndromes such as brachial plexus avulsion.

Neovascularization

The α7 NNR is associated with neovascularization. Inhibition of neovascularization, for example, by administering antagonists (or at certain dosages, partial agonists) of the α7 NNR can treat or prevent conditions characterized by undesirable neovascularization or angiogenesis. Such conditions can include those characterized by inflammatory angiogenesis and/or ischemia-induced angiogenesis. Neovascularization associated with tumor growth can also be inhibited by administering those compounds described herein that function as antagonists or partial agonists of α7 NNR.

Specific antagonism of α7 NNR-specific activity reduces the angiogenic response to inflammation, ischemia, and neoplasia. Guidance regarding appropriate animal model systems for evaluating the compounds described herein can be found, for example, in Heeschen, C. et al., "A novel angiogenic pathway mediated by non-neuronal nicotinic acetylcholine receptors," *J. Clin. Invest.* 110(4):527-36 (2002), incorporated herein by reference regarding disclosure of α7-specific inhibition of angiogenesis and cellular (in vitro) and animal modeling of angiogenic activity relevant to human disease, especially the Lewis lung tumor model (in vivo, in mice—see, in particular, pages 529, and 532-533).

Representative tumor types that can be treated using the compounds described herein include NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas, and the plaques and tumors of mycosis fungoides and cutaneous T-cell lymphoma/leukemia), and solid tumors arising from lymphomas.

The compounds can also be administered in conjunction with other forms of anti-cancer treatment, including co-administration with antineoplastic antitumor agents such as cis-platin, adriamycin, daunomycin, and the like, and/or anti-VEGF (vascular endothelial growth factor) agents, as such are known in the art.

The compounds can be administered in such a manner that they are targeted to the tumor site. For example, the compounds can be administered in microspheres, microparticles or liposomes conjugated to various antibodies that direct the microparticles to the tumor. Additionally, the compounds can be present in microspheres, microparticles or liposomes that are appropriately sized to pass through the arteries and veins, but lodge in capillary beds surrounding tumors and administer the compounds locally to the tumor. Such drug delivery devices are known in the art.

Other Disorders

In addition to treating CNS disorders, inflammation, neovascularization, and pain, the compounds of the present invention can be also used to prevent or treat certain other conditions, diseases, and disorders in which NNRs play a role. Examples include autoimmune disorders such as Lupus, disorders associated with cytokine release, cachexia secondary to infection (e.g., as occurs in AIDS, AIDS related complex and neoplasia), metabolic disorders, including type I diabetes, type II diabetes, metabolic syndrome, obesity, or hyperglycemia, pemphitis, urinary incontinence, retinal diseases, infectious diseases, myasthenia, Eaton-Lambert syndrome, hypertension, osteoporosis, vasoconstriction, vasodilatation, cardiac arrhythmias, bulimia, anorexia as well as those indications set forth in published PCT application WO 98/25619, herein incorporated by reference with regard to such disorders. The compounds of this invention can also be administered to treat convulsions such as those that are symptomatic of epilepsy, and to treat conditions such as syphillis and Creutzfeld-Jakob disease.

Diagnostic Uses

The compounds can be used in diagnostic compositions, such as probes, particularly when they are modified to include appropriate labels. The probes can be used, for example, to determine the relative number and/or function of specific receptors, particularly the α7 receptor subtype. For this purpose the compounds of the present invention most preferably are labeled with a radioactive isotopic moiety such as $^{11}C$, $^{18}F$, $^{76}Br$, $^{123}I$ or $^{125}I$.

The administered compounds can be detected using known detection methods appropriate for the label used. Examples of detection methods include position emission topography (PET) and single-photon emission computed tomography (SPECT). The radiolabels described above are useful in PET (e.g., $^{11}C$, $^{18}F$ or $^{76}Br$) and SPECT (e.g., $^{123}I$) imaging, with half-lives of about 20.4 minutes for $^{11}C$, about 109 minutes for $^{18}F$, about 13 hours for $^{123}I$, and about 16 hours for $^{76}Br$. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al., incorporated herein by reference with regard to administration of such compounds.

The compounds can be administered using known techniques. See, for example, U.S. Pat. No. 5,969,144 to London et al., as noted, incorporated by reference with regard to such administration. The compounds can be administered in formulation compositions that incorporate other ingredients, such as those types of ingredients that are useful in formulating a diagnostic composition. Compounds useful in accordance with carrying out the present invention most preferably are employed in forms of high purity. See, U.S. Pat. No. 5,853,696 to Elmalch et al., herein incorporated by reference with regard to such analysis.

After the compounds are administered to a subject (e.g., a human subject), the presence of that compound within the subject can be imaged and quantified by appropriate techniques in order to indicate the presence, quantity, and functionality of selected NNR subtypes. In addition to humans, the compounds can also be administered to animals, such as mice, rats, dogs, and monkeys. SPECT and PET imaging can be carried out using any appropriate technique and apparatus. See Villemagne et al., In: Arneric et al. (Eds.) *Neuronal Nicotinic Receptors: Pharmacology and Therapeutic Opportunities*, 235-250 (1998) and U.S. Pat. No. 5,853,696 to Elmalch et al., each herein incorporated by reference, for a disclosure of representative imaging techniques.

The radiolabeled compounds bind with high affinity to selective NNR subtypes (e.g., α7) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected NNR subtypes (e.g., α7 receptor subtype). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al., herein incorporated by reference.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes namely, the α7 receptor subtype.

Receptor Binding

The compounds of this invention can be used as reference ligands in binding assays for compounds which bind to NNR subtypes, particularly the α7 receptor subtype. For this purpose the compounds of this invention are preferably labeled with a radioactive isotopic moiety such as $^3$H, or $^{14}$C.

V. Synthetic Examples

The following synthetic examples are provided to illustrate the present invention and should not be construed as limiting the scope thereof. In these examples, all parts and percentages are by weight, unless otherwise noted. All solutions are aqueous unless otherwise noted.

Example 1

Small scale synthesis of (2S,3R)—N-(2-((3-pyridinyl)methyl)-1-azabicyclo[2.2.2]octan-3-yl)benzofuran-2-carboxamide (Compound A) and its enantiomer, (2R,3S)—N-(2-((3-pyridinyl)methyl)-1-azabicyclo[2.2.2]octan-3-yl)benzofuran-2-carboxamide 2-((3-Pyridinyl)methylene)-1-azabicyclo[2.2.2]octan-3-one Potassium hydroxide (56 g, 0.54 mole) was dissolved in methanol (420 mL). 3-Quinuclidinone hydrochloride (75 g, 0.49 mole) was added and the mixture was stirred for 30 min at ambient temperature. 3-Pyridinecarboxaldehyde (58 g, 0.54 mole) was added and the mixture stirred for 16 h at ambient temperature. The reaction mixture became yellow during this period, with solids caking on the walls of the flask. The solids were scraped from the walls and the chunks broken up. With rapid stirring, water (390 mL) was added. When the solids dissolved, the mixture was cooled at 4° C. overnight. The crystals were collected by filtration, washed with water, and air dried to obtain 80 g of yellow solid. A second crop (8 g) was obtained by concentration of the filtrate to ~10% of its former volume and cooling at 4° C. overnight. Both crops were sufficiently pure for further transformation (88 g, 82% yield).

2-((3-Pyridinyl)methyl)-1-azabicyclo[2.2.2]octan-3-one 2-((3-Pyridinyl)methylene)-1-azabicyclo[2.2.2]octan-3-one (20 g, 93 mmol) was suspended in methanol (200 mL) and treated with 46 mL of 6 M hydrochloric acid. 10% Palladium on carbon (1.6 g) was added and the mixture was shaken under 25 psi hydrogen for 16 h. The mixture was filtered through diatomaceous earth, and the solvent was removed from the filtrate by rotary evaporation. This provided crude 2-((3-pyridinyl)methyl)-1-azabicyclo[2.2.2]octan-3-one hydrochloride, as a white gum (20 g), which was subsequently treated with 2 M sodium hydroxide (50 mL) and chloroform (50 mL) and stirred for an hour. The chloroform layer was separated, and the aqueous phase was treated with 2 M sodium hydroxide (~5 mL, enough to raise the pH to 10) and saturated aqueous Sodium chloride (25 mL). This aqueous mixture was extracted with chloroform (3×10 mL), and the combined chloroform extracts were dried (anhydrous magnesium sulfate) and concentrated by rotary evaporation. The residue (18 g) was dissolved in warm ether (320 mL) and cooled to 4° C. The white solid was filtered off, washed with a small portion of cold ether and air dried. Concentration of the filtrate to ~10% of its former volume and cooling at 4° C. produced a second crop. A combined yield 16 g (79%) was obtained.

3-Amino-2-((3-pyridinyl)methyl)-1-azabicyclo[2.2.2]octane

To a stirred solution of 2-((3-pyridinyl)methyl)-1-azabicyclo[2.2.2]octan-3-one (3.00 g, 13.9 mmol) in dry methanol (20 mL), under nitrogen, was added a 1 M solution of zinc chloride in ether (2.78 mL, 2.78 mmol). After stirring at ambient temperature for 30 min, this mixture was treated with solid ammonium formate (10.4 g, 167 mmol). After stirring another hour at ambient temperature, solid sodium cyanoborohydride (1.75 g, 27.8 mmol) was added in portions. The reaction was then stirred at ambient temperature overnight and terminated by addition of water (~5 mL). The quenched reaction was partitioned between 5 M sodium hydroxide (10 mL) and chloroform (20 mL). The aqueous layer was extracted with chloroform (20 mL), and combined organic layers were dried (sodium sulfate), filtered and concentrated. This left 2.97 g of yellow gum. GCMS analysis indicated that the product was a 1:9 mixture of the cis and trans amines, along with a trace of the corresponding alcohol (98% total mass recovery).

(2R,3S) and (2S,3R)-3-amino-2-((3-pyridinyl)methyl)-1-azabicyclo[2.2.2]octane

Di-p-toluoyl-D-tartaric acid (5.33 g, 13.8 mmol) was added to a stirred solution of crude 3-amino-2-((3-pyridinyl)methyl)-1-azabicyclo[2.2.2]octane (6.00 g, 27.6 mmol of 1:9 cis/trans) in methanol (20 mL). After complete dissolution, the clear solution was then concentrated to a solid mass by rotary evaporation. The solid was dissolved in a minimum amount of boiling methanol (~5 mL). The solution was cooled slowly, first to ambient temperature (1 h), then for ~4 h at 5° C. and finally at −5° C. overnight. The precipitated salt was collected by suction filtration and recrystallized from 5 mL of methanol. Air drying left 1.4 g of white solid, which was partitioned between chloroform (5 mL) and 2 M sodium hydroxide (5 mL). The chloroform layer and a 5 mL chloroform extract of the aqueous layer were combined, dried (anhydrous sodium sulfate) and concentrated to give a colorless oil (0.434 g). The enantiomeric purity of this free base was determined by conversion of a portion into its N-(tert-butoxycarbonyl)-L-prolinamide, which was then analyzed for diastereomeric purity (98%) using LCMS.

The mother liquor from the initial crystallization was made basic (~pH 11) with 2 M sodium hydroxide and extracted twice with chloroform (10 mL). The chloroform extracts were dried (anhydrous sodium sulfate) and concentrated to give an oil. This amine (3.00 g, 13.8 mmol) was dissolved in methanol (10 mL) and treated with di-p-toluoyl-L-tartaric acid (2.76 g, 6.90 mmol). The mixture was warmed to aid dissolution and then cooled slowly to −5° C., where it remained overnight. The precipitate was collected by suction filtration, recrystallized from methanol and dried. This left 1.05 g of white solid. The salt was converted into the free base (yield=0.364 g), and the enantiomeric purity (97%) was assessed using the prolinamide method, as described above for the other enantiomer.

Trans enantiomer A of N-(2-((3-pyridinyl)methyl)-1-azabicyclo[2.2.2]octan-3-yl)benzofuran-2-carboxamide Diphenylchlorophosphate (0.35 mL, 0.46 g, 1.7 mmol) was added drop-wise to a solution of benzofuran-2-carboxylic acid (0.28 g, 1.7 mmol) and triethylamine (0.24 mL, 0.17 g, 1.7 mmol) in dry dichloromethane (5 mL). After stirring at ambient temperature for 30 min, a solution of (2S,3R)-3-amino-2-((3-pyridinyl)methyl)-1-azabicyclo[2.2.2]octane (0.337 g, 1.55 mmol) (that derived from the di-p-toluoyl-D-tartaric acid salt) and triethylamine (0.24 mL, 0.17 g, 1.7 mmol) in dry dichloromethane (5 mL) was added. The reaction mixture was stirred overnight at ambient temperature, and then treated with 10% sodium hydroxide (1 mL). The biphasic mixture was separated, and the organic layer was concentrated on a Genevac centrifugal evaporator. The residue was dissolved in methanol (6 mL) and purified by HPLC on a C18 silica gel column, using an acetonitrile/water gradient, containing 0.05% trifluoroacetic acid, as eluent. Concentration of selected fractions, partitioning of the resulting residue between chloroform and saturated aqueous sodium bicarbonate, and evaporation of the chloroform gave 0.310 g (42% yield) of white powder (95% pure by GCMS). $^1$H NMR (300 MHz, CDCl$_3$) δ 8.51 (d, 1H), 8.34 (dd, 1H), 7.66 (d, 1H), 7.58 (dt, 1H), 7.49 (d, 1H), 7.44 (s, 1H), 7.40 (dd, 1H), 7.29 (t, 1H), 7.13 (dd, 1H), 6.63 (d, 1H), 3.95 (t, 1H), 3.08 (m, 1H), 2.95 (m, 4H), 2.78 (m, 2H), 2.03 (m, 1H), 1.72 (m, 3H), 1.52 (m, 1H).

This material (trans enantiomer A) was later determined to be identical, by chiral chromatogrphic analysis, to material whose absolute configuration is 2S,3R (established by x-ray crystallographic analysis).

Trans enantiomer B of N-(2-((3-pyridinyl)methyl)-1-azabicyclo[2.2.2]octan-3-yl)benzofuran-2-carboxamide Diphenylchlorophosphate (96 µL, 124 mg, 0.46 mmol) was added drop-wise to a solution of the benzofuran-2-carboxylic acid (75 mg, 0.46 mmol) and triethylamine (64 µL, 46 mg, 0.46 mmol) in dry dichloromethane (1 mL). After stirring at ambient temperature for 45 min, a solution of (2R,3S)-3-amino-2-((3-pyridinyl)methyl)-1-azabicyclo[2.2.2]octane (0.10 g, 0.46 mmol) (that derived from the di-p-toluoyl-L-tartaric acid salt) and triethylamine (64 µL, 46 mg, 0.46 mmol) in dry dichloromethane (1 mL) was added. The reaction mixture was stirred overnight at ambient temperature, and then treated with 10% sodium hydroxide (1 mL). The biphasic mixture was separated, and the organic layer and a chloroform extract (2 mL) of the aqueous layer was concentrated by rotary evaporation. The residue was dissolved in methanol and purified by HPLC on a C18 silica gel column, using an acetonitrile/water gradient, containing 0.05% trifluoroacetic acid, as eluent. Concentration of selected fractions, partitioning of the resulting residue between chloroform and saturated aqueous sodium bicarbonate, and evaporation of the chloroform gave 82.5 mg (50% yield) of a white powder. The NMR spectrum was identical to that obtained for the 2S,3R isomer.

Since the immediate precursor of this material (trans enantiomer B) is enantiomeric to the immediate precursor of 2S,3R compound (trans enantiomer A), the absolute configuration of trans enantiomer B is presumed to be 2R,3S.

Example 2

Large scale synthesis of (2S,3R)—N-(2-((3-pyridinyl)methyl)-1-azabicyclo[2.2.2]octan-3-yl)benzofuran-2-carboxamide and (2S,3R)—N-(2-((3-pyridinyl)methyl)-1-azabicyclo[2.2.2]oct-3-yl)-1-benzofuran-2-carboxamide p-toluenesulfonate salt 2-((3-Pyridinyl)methylene)-1-azabicyclo[2.2.2]octan-3-one 3-Quinuclidinone hydrochloride (8.25 kg, 51.0 mol) and methanol (49.5 L) were added to a 100 L glass reaction flask, under an nitrogen atmosphere, equipped with a mechanical stirrer, temperature probe, and condenser. Potassium hydroxide (5.55 kg, 99.0 mol) was added via a powder funnel over an approximately 30 min period, resulting in a rise in reaction temperature from 50° C. to 56° C. Over an approximately 2 h period, 3-pyridinecarboxaldehyde (4.80 kg, 44.9 mol) was added to the reaction mixture. The resulting mixture was stirred at 20° C.±5° C. for a minimum of 12 h, as the reaction was monitored by thin layer chromatography (TLC). Upon completion of the reaction, the reaction mixture was filtered through a sintered glass funnel and the filter cake was washed with methanol (74.2 L). The filtrate was concentrated, transferred to a reaction flask, and water (66.0 L) was added. The suspension was stirred for a minimum of 30 min, filtered, and the filter cake was washed with water (90.0 L) until the pH of the rinse was 7-9. The solid was dried under vacuum at 50° C.±5° C. for a minimum of 12 h to give 8.58 kg (89.3%) of 2-((3-pyridinyl)methylene)-1-azabicyclo[2.2.2]octan-3-one.

(2S)-2-((3-pyridinyl)methyl)-1-azabicyclo[2.2.2]octan-3-one-di-p-toluoyl-D-tartrate salt 2-((3-Pyridinyl)methylene)-1-azabicyclo[2.2.2]octan-3-one (5.40 kg, 25.2 mol) and methanol (40.5 L) were added to a 72 L reaction vessel under an inert atmosphere equipped with a mechanical stirrer, temperature probe, low-pressure gas regulator system, and pressure gauge. The headspace was filled with nitrogen, and the mixture was stirred to obtain a clear yellow solution. To the flask was added 10% palladium on carbon (50% wet) (270 g). The atmosphere of the reactor was evacuated using a vacuum pump, and the headspace was replaced with hydrogen to 10 to 20 inches water pressure. The evacuation and pressurization with hydrogen were repeated 2 more times, leaving the reactor under 20 inches water pressure of hydrogen gas after the third pressurization. The reaction mixture was stirred at 20° C.±5° C. for a minimum of 12 h, and the reaction was monitored via TLC. Upon completion of the reaction, the suspension was filtered through a bed of Celite®545 (1.9 kg) on a sintered glass funnel, and the filter cake was washed with methanol (10.1 L). The filtrate was concentrated to obtain a semi-solid which was transferred, under an nitrogen atmosphere, to a 200 L reaction flask fitted with a mechanical stirrer, condenser, and temperature probe. The semi-solid was dissolved in ethanol (57.2 L), and di-p-toluoyl-D-tartaric acid (DTTA) (9.74 kg, 25.2 mol) was added. The stirring reaction mixture was heated at reflux for a minimum of 1 h, and for an additional minimum of 12 h while the reaction was cooled to between 15° C. and 30° C. The suspension was filtered using a tabletop filter, and the filter cake was washed with ethanol (11.4 L). The product was dried under vacuum at ambient temperature to obtain 11.6 kg (76.2% yield, 59.5% factored for purity) of (2S)-2-((3-pyridinyl)methyl)-1-azabicyclo[2.2.2]octan-3-one di-p-toluoyl-D-tartrate salt.

(2S,3R)-3-Amino-2-((3-Pyridinyl)methyl)-1-azabicyclo[2.2.2]octane di-p-toluoyl-D-tartrate salt Water (46.25 L) and sodium bicarbonate (4.35 kg, 51.8 mol) were added to a 200 L flask. Upon complete dissolution, dichloromethane (69.4 L) was added. (2S)-2-((3-Pyridinyl)methyl)-1-azabicyclo[2.2.2]octan-3-one di-p-toluoyl-D-tartrate salt (11.56 kg, 19.19 mol) was added, and the reaction mixture was stirred for between 2 min and 10 min. The layers were allowed to separate for a minimum of 2 min (additional water (20 L) was added when necessary to partition the layers). The organic phase was removed and dried over anhydrous sodium sulfate. Dichloromethane (34.7 L) was added to the remaining aqueous phase, and the suspension was stirred for between 2 min and 10 min. The layers were allowed to separate for between 2 min and 10 min. Again, the organic phase was removed and dried over anhydrous sodium sulfate. The extraction of the aqueous phase with dichloromethane (34.7 L) was repeated one more time, as above. Samples of each extraction were submitted for chiral HPLC analysis. The sodium sulfate was removed by filtration, and the filtrates were concentrated to obtain (2S)-2-((3-pyridinyl)methyl)-1-azabicyclo[2.2.2]octan-3-one (4.0 kg) as a solid.

The (2S)-2-((3-pyridinyl)methyl)-1-azabicyclo[2.2.2]octan-3-one (3.8 kg) was transferred to a clean 100 L glass reaction flask, under a nitrogen atmosphere, fitted with a mechanical stirrer and temperature probe. Anhydrous tetrahydrofuran (7.24 L) and (+)-(R)-α-methylbenzylamine (2.55 L, 20.1 mol) were added. Titanium(IV) isopropoxide (6.47 L, 21.8 mol) was added to the stirred reaction mixture over a 1 h period. The reaction was stirred under a nitrogen atmosphere for a minimum of 12 h. Ethanol (36.17 L) was added to the reaction mixture. The reaction mixture was cooled to below −5° C., and sodium borohydride (1.53 kg, 40.5 mol) was added in portions, keeping the reaction temperature below 15° C. (this addition took several hours). The reaction mixture was then stirred at 15° C.±10° C. for a minimum of 1 h. The reaction was monitored by HPLC, and upon completion of the reaction (as indicated by less than 0.5% of (2S)-2-((3-pyridinyl)methyl)-1-azabicyclo[2.2.2]octan-3-one remaining), 2 M sodium hydroxide (15.99 L) was added and the mixture was stirred for a minimum of 10 min. The reaction mixture was filtered through a bed of Celite®545 in a tabletop funnel. The filter cake was washed with ethanol (15.23 L), and the filtrate was concentrated to obtain an oil.

The concentrate was transferred to a clean 100 L glass reaction flask equipped with a mechanical stirrer and temperature probe under an inert atmosphere. Water (1 L) was added, and the mixture was cooled to 0° C.±5° C. 2 M Hydrochloric acid (24 L) was added to the mixture to adjust the pH of the mixture to pH 1. The mixture was then stirred for a minimum of 10 min, and 2 M sodium hydroxide (24 L) was slowly added to adjust the pH of the mixture to pH 14. The mixture was stirred for a minimum of 10 min, and the aqueous phase was extracted with dichloromethane (3×15.23 L). The organic phases were dried over anhydrous sodium sulfate (2.0 kg), filtered, and concentrated to give (2S,3R)—N-((1R)-phenylethyl)-3-amino-2-((3-pyridinyl)methyl))-1-azabicyclo[2.2.2]octane (4.80 kg, 84.7% yield).

The (2S,3R)—N-((1R)-phenylethyl)-3-amino-2-((3-pyridinyl)methyl)-1-azabicyclo[2.2.2]octane was transferred to a 22 L glass flask equipped with a mechanical stirrer and temperature probe under an inert atmosphere. Water (4.8 L) was added, and the stirring mixture was cooled to 5° C.±5° C. Concentrated hydrochloric acid (2.97 L) was slowly added to the reaction flask, keeping the temperature of the mixture below 25° C. The resulting solution was transferred to a 72 L reaction flask containing ethanol (18 L), equipped with a mechanical stirrer, temperature probe, and condenser under an inert atmosphere. To the flask was added 10% palladium on carbon (50% wet) (311.1 g) and cyclohexene (14.36 L). The reaction mixture was heated at near-reflux for a minimum of 12 h, and the reaction was monitored by TLC. Upon completion of the reaction, the reaction mixture was cooled to below 45° C., and it was filtered through a bed of Celite®545 (1.2 kg) on a sintered glass funnel. The filter cake was rinsed with ethanol (3 L) and the filtrate was concentrated to obtain an aqueous phase. Water (500 mL) was added to the concentrated filtrate, and this combined aqueous layer was washed with methyl tert-butyl ether (MTBE) (2×4.79 L). 2 M Sodium hydroxide (19.5 L) was added to the aqueous phase to adjust the pH of the mixture to pH 14. The mixture was then stirred for a minimum of 10 min. The aqueous phase was extracted with chloroform (4×11.96 L), and the combined organic phases were dried over anhydrous sodium sulfate (2.34 kg). The filtrate was filtered and concentrated to obtain (2S,3R)-3-amino-2-((3-pyridinyl)methyl)-1-azabicyclo[2.2.2]octane (3.49 kg, >quantitative yield) as an oil.

The (2S,3R)-3-amino-2-((3-pyridinyl)methyl)-1-azabicyclo[2.2.2]octane was transferred to a clean 100 L reaction flask equipped with a mechanical stirrer, condenser, and temperature probe under an inert atmosphere. Ethanol (38.4 L) and di-p-toluoyl-D-tartaric acid (3.58 kg, 9.27 mol) were added. The reaction mixture was heated at gentle reflux for a minimum of 1 h. The reaction mixture was then stirred for a minimum of 12 h while it was cooled to between 15° C. and 30° C. The resulting suspension was filtered, and the filter cake was washed with ethanol (5.76 L). The filter cake was transferred to a clean 100 L glass reaction flask equipped with a mechanical stirrer, temperature probe, and condenser under an inert atmosphere. A 9:1 ethanol/water solution (30.7 L) was added, and the resulting slurry was heated at gentle reflux for a minimum of 1 h. The reaction mixture was then stirred for a minimum of 12 h while cooling to between 15° C. and 30° C. The mixture was filtered and the filter cake was washed with ethanol (5.76 L). The product was collected and dried under vacuum at 50° C.±5° C. for a minimum of 12 h to give 5.63 kg (58.1% yield) of (2S,3R)-3-amino-2-((3-pyridinyl)methyl)-1-azabicyclo[2.2.2]octane di-p-toluoyl-D-tartrate salt.

(2S,3R)—N-(2-((3-Pyridinyl)methyl)-1-azabicyclo[2.2.2]octan-3-yl)benzofuran-2-carboxamide (2S,3R)-3-Amino-2-((3-pyridinyl)methyl)-1-azabicyclo[2.2.2]octane di-p-toluoyl-D-tartrate salt (3.64 kg, 5.96 mol) and 10% aqueous sodium chloride solution (14.4 L, 46.4 mol) were added to a 72 L glass reaction flask equipped with a mechanical stirrer under an inert atmosphere. 5 M Sodium hydroxide (5.09 L) was added to the stirring mixture to adjust the pH of the mixture to pH 14. The mixture was then stirred for a minimum of 10 min. The aqueous solution was extracted with chloroform (4×12.0 L), and the combined organic layers were dried over anhydrous sodium sulfate (1.72 kg). The combined organic layers were filtered, and the filtrate was concentrated to obtain (2S,3R)-3-amino-2-((3-pyridinyl)methyl)-1-azabicyclo[2.2.2]octane (1.27 kg) as an oil.

The (2S,3R)-3-amino-2-((3-pyridinyl)methyl)-1-azabicyclo[2.2.2]octane was transferred to a 50 L glass reaction flask equipped with a mechanical stirrer under an inert atmosphere. Dichloromethane (16.5 L), triethylamine (847 mL, 6.08 mol), benzofuran-2-carboxylic acid (948 g, 5.85 mol) and O-(benzotriazol-1-yl)-N,N,N,1-tetramethyluronium hexafluorophosphate (HBTU) (2.17 kg, 5.85 mol) were added to the reaction mixture. The mixture was stirred for a minimum of 4 h at ambient temperature, and the reaction was monitored by HPLC. Upon completion of the reaction, 10% aqueous potassium carbonate (12.7 L, 17.1 mol) was added to the reaction mixture and the mixture was stirred for a minimum of 5 min. The layers were separated and the organic phase was washed with 10% brine (12.7 L). The layers were separated and the organic phase was cooled to 15° C.±10° C. 3 M Hydrochloric acid (8.0 L) was slowly added to the reaction mixture to adjust the pH of the mixture to pH 1. The mixture was then stirred for a minimum of 5 min, and the layers were allowed to partition for a minimum of 5 min. The solids were filtered using a table top filter. The layers of the filtrate were separated, and the aqueous phase and the solids from the funnel were transferred to the reaction flask. 3 M Sodium hydroxide (9.0 L) was slowly added to the flask in portions to adjust the pH of the mixture to pH 14. The aqueous phase was extracted with dichloromethane (2×16.5 L). The combined organic phases were dried over anhydrous sodium sulfate (1.71 kg). The mixture was filtered, and the filtrate was concentrated to give (2S,3R)—N-(2-((3-pyridinyl)methyl)-1-azabicyclo[2.2.2]octan-3-yl)benzofuran-2-carboxamide (1.63 kg, 77.0% yield) as a yellow solid.

(2S,3R)—N-(2-((3-pyridinyl)methyl)-1-azabicyclo[2.2.2]oct-3-yl]benzofuran-2-carboxamide D-toluenesulfonate (2S,3R)—N-(2-((3-Pyridinyl)methyl)-1-azabicyclo[2.2.2]octan-3-yl)benzofuran-2-carboxamide (1.62 kg, 4.48 mol) and dichloromethane (8.60 kg) were added into a carboy. The weight/weight percent of the material in solution was determined through HPLC analysis. The solution was concentrated to an oil, acetone (4 L) was added, and the mixture was concentrated to an oily solid. Additional acetone (12 L) was added to the oily solid in the rotary evaporator bulb, and the resulting slurry was transferred to a 50 L glass reaction flask with a mechanical stirrer, condenser, temperature probe, and condenser under an inert atmosphere. The reaction mixture was heated to 50° C.±5° C. Water (80.7 g) was added to the solution, and it was stirred for a minimum of 10 min. p-Toluenesulfonic acid (853 g, 4.44 mol) was added to the reaction mixture in portions over approximately 15 min. The reaction mixture was heated to reflux and held at that temperature for a minimum of 30 min to obtain a solution. The reaction was cooled to 40° C.±5° C. over approximately 2 h. Isopropyl acetate (14.1 L) was added over approximately 1.5 h. The reaction mixture was slowly cooled to ambient temperature over a minimum of 10 h. The mixture was filtered and the filter cake was washed with isopropyl acetate (3.5 L). The isolated product was dried under vacuum at 105° C.±5° C. for between 2 h and 9 h to give 2.19 kg (88.5% yield) of (2S,3R)—N-(2-((3-pyridinyl)methyl)-1-azabicyclo[2.2.2]oct-3-yl)benzofuran-2-carboxamide p-toluenesulfonate, mp 226-228° C. $^1$H NMR (500 MHz, D$_2$O) δ 8.29 (s, 1H), 7.78 (m, J=5.1, 1H), 7.63 (d, J=7.9, 1H), 7.54 (d, J=7.8, 1H), 7.49 (d, J=8.1, 2H), 7.37 (m, J=8.3, 1H), 7.33 (m, J=8.3, 6.9, 1.0, 1H), 7.18 (m, J=7.8, 6.9, 1.0, 1H), 7.14 (d, J=8.1, 2H), 7.09 (s, 1H), 6.99 (dd, J=7.9, 5.1, 1H), 4.05 (m, J=7.7, 1H), 3.74 (m, 1H), 3.47 (m, 2H), 3.28 (m, 1H), 3.22 (m, 1H), 3.15 (dd, J=13.2, 4.7, 1H), 3.02 (dd, J=13.2, 11.5, 1H), 2.19 (s, 3H), 2.02 (m, 2H), 1.93 (m, 2H), 1.79 (m, 1H). $^{13}$C NMR (126 MHz, D$_2$O) δ 157.2, 154.1, 150.1, 148.2, 146.4, 145.2, 138.0, 137.0, 130.9, 128.2 (2), 126.9, 126.8, 125.5 (2), 123.7, 123.3, 122.7, 111.7, 100.7, 61.3, 50.2, 48.0, 40.9, 33.1, 26.9, 21.5, 20.8, 17.0.

Samples of this material were converted into Compound A free base (for use in salt selection studies) by treatment with aqueous sodium hydroxide and extraction with chloroform. Thorough evaporation of the chloroform left an off-white powder, mp 167-170° C., with the following spectral characteristics: Positive ion electrospray MS [M+H]$^+$ ion m/z=362. $^1$H NMR (500 MHz, DMSO-d$_6$) δ 8.53 (d, J=7.6 Hz, 1H), 8.43 (d, J=1.7 Hz, 1H), 8.28 (dd, J=1.6, 4.7 Hz, 1H), 7.77 (d, J=7.7 Hz, 1H), 7.66 (d, J=8.5 Hz, 1H), 7.63 (dt, J=1.7, 7.7 Hz, 1H), 7.52 (s, 1H), 7.46 (m, J=8.5, 7.5 Hz, 1H), 7.33 (m, J=7.7, 7.5 Hz, 1H), 7.21 (dd, J=4.7, 7.7 Hz, 1H), 3.71 (m, J=7.6 Hz, 1H), 3.11 (m, 1H), 3.02 (m, 1H), 2.80 (m, 2H), 2.69 (m, 2H), 2.55 (m, 1H), 1.80 (m, 1H), 1.77 (m, 1H), 1.62 (m, 1H), 1.56 (m, 1H), 1.26 (m, 1H). $^{13}$C NMR (126 MHz, DMSO-d$_6$) δ 158.1, 154.1, 150.1, 149.1, 146.8, 136.4, 135.4, 127.1, 126.7, 123.6, 122.9, 122.6, 111.8, 109.3, 61.9, 53.4, 49.9, 40.3, 35.0, 28.1, 26.1, 19.6.

The monohydrochloride salt of Compound A (see Example 5) was submitted for x-ray crystallographic analysis. The resulting crystal structure (shown in FIGS. 10A and 10B, respectively) established the 2S,3R absolute configuration of Compound A.

Example 3

Synthesis of (2S,3R)—N-(2-((3-pyridinyl)methyl)-1-azabicyclo[2.2.2]oct-3-yl)benzofuran-2-carboxamide phosphate salt To a round bottom flask was added (2S,3R)—N-(2-((3-pyridinyl)methyl)-1-azabicyclo[2.2.2]oct-3-yl)benzofuran-2-carboxamide (8.18 g, 22.6 mmol) and 2-propanol (180 mL). The mixture was stirred and heated at 65-70° C. until all solids had dissolved. The solution was vigorously stirred at 65-70° C., and phosphoric acid (1.65 mL, 24.3 mmol) was added drop-wise by pipette. Immediately, a white, granular solid formed. The mixture was stirred at 65-70° C. for 30 minutes, cooled to ambient temperature (23° C.) and stirred for an additional 24 h. The white solids were collected by suction filtration, the filter cake was washed with 2-propanol (20 mL) and the solid was air-dried for at least 1 h. The solid was dried further in a vacuum oven at 75° C. overnight (16 h) to give 10.7 g of the product (>quantitative yield), mp 265-273° C. with decomposition, with crystallinity changes observed at ~180° C. $^1$H-NMR (DMSO-$d_6$) indicated the presence of 2-propanol (strong solvate), which may explain the greater than quantitative yield. Chiral LC analysis gave a purity of 97.1% (270 nm).

Example 4

Synthesis of (2S,3R)—N-(2-((3-pyridinyl)methyl)-1-azabicyclo[2.2.2]oct-3-yl)benzofuran-2-carboxamide maleate salt Maleic acid (0.067 g, 0.630 mmol) was added to a hot slurry of (2S,3R)—N-(2-((3-pyridinyl)methyl)-1-azabicyclo [2.2.2]oct-3-yl)benzofuran-2-carboxamide (0.203 g, 0.560 mmol) in isopropyl acetate (2 mL), depositing fine, white solids, along with a gummy residue. Additional isopropyl acetate (3 mL) and maleic acid (0.006 g) were added, and the mixture was heated to reflux. Isopropanol (5 mL) was added at reflux. The resulting mixture of white solids was cooled to ambient temperature, filtered, and the solids were washed with isopropyl acetate (2 mL). The product was dried under vacuum at 60° C. for 18 h to give 0.228 g of an off-white, flaky solid (84.7% yield), mp 180-182° C. $^1$H NMR (DMSO-$d_6$) indicated a mono-salt stoichiometry. Calc'd for $C_{22}H_{23}N_3O_2 \cdot C_4H_4O_4$: C, 65.40; H, 5.70; N, 8.80. Found: C, 65.35, 65.29; H, 5.86, 5.68; N, 8.69, 8.78.

Example 5

Synthesis of (2S,3R)—N-(2-((3-pyridinyl)methyl)-1-azabicyclo[2.2.2]oct-3-yl)benzofuran-2-carboxamide hydrochloride salts Monohydrochloride: A hydrochloric acid/THF solution was prepared by adding of concentrated hydrochloric acid (1.93 mL of 12M, 23.2 mmol) drop-wise to 8.5 mL of chilled THF. The solution was warmed to ambient temperature. To a round bottom flask was added (2S,3R)—N-(2-((3-pyridinyl) methyl)-1-azabicyclo[2.2.2]oct-3-yl)benzofuran-2-carboxamide (8.49 g, 23.5 mmol) and acetone (85 mL). The mixture was stirred and heated at 45-50° C. until a complete solution was obtained. The hydrochloric acid/THF solution prepared above was added drop-wise over a 5 min period, with additional THF (1.5 mL) used in the transfer. Granular, white solids began to form during the addition of the acid solution. The mixture was cooled to ambient temperature, and stirred overnight (16 h). The solids were collected by suction filtration, the filter cake was washed with acetone (10 mL), and the solid was air-dried with suction for 30 min. The solid was further dried in a vacuum oven at 75° C. for 2 h to give 8.79 g of the fine white crystals (94% yield), mp 255-262° C. Chiral LC analysis gave a purity of 98.8% (270 nm). $^1$H-NMR (DMSO-$d_6$) shows no residual solvents and confirms mono stoichiometry. $^1$H NMR (300 MHz, DMSO-$d_6$) δ 10.7 (broad s, 1H-quaternary ammonium), 8.80 (broad s, 1H-amide H), 8.54 (s, 1H), 8.23 (d, 1H), 7.78 (d, 1H), 7.74 (d, 1H), 7.60 (d, 1H), 7.47 (m, 2H), 7.33 (m, 1H), 7.19 (m, 1H), 4.19 (m, 1H), 4.08 (m, 1H), 3.05-3.55 (m, 6H), 2.00-2.10 (m, 3H), 1.90 (m, 1H), 1.70 (m, 1H). An x-ray crystallographic analysis of this salt established stereochemical assignment and stoichiometry (see FIGS. 10A and 10B).

Dihydrochloride: Hydrogen chloride gas was slowly bubbled into a ice cooled solution of (2S,3R)—N-(2-((3-pyridinyl)methyl)-1-azabicyclo[2.2.2]oct-3-yl)benzofuran-2-carboxamide (1.9 g, 5.3 mmol) in anhydrous ether (25 mL). The volatiles were removed, first in a nitrogen stream and then with high vacuum (sodium hydroxide scrubber in high vacuum line). The residue was triturated several times with small volumes of anhydrous ether (discarded), and the remaining solid was dried under high vacuum. This gave 2.17 g (94% yield) of off-white powder, mp 210-212° C. (hygroscopic). Chiral LC analysis gave a purity of 93.7% (270 nm). Positive ion electrospray MS [M+H]$^+$ ion m/z=362. $^1$H NMR (300 MHz, CD$_3$OD) δ 9.15 (s, 1H), 8.84 (d, 1H), 8.63 (d, 1H), 7.97 (t, 1H), 7.75 (d, 1H), 7.61 (d, 1H), 7.52 (m, 2H), 7.35 (t, 1H), 4.50 (m, 1H), 4.32 (m, 1H), 3.40-3.85 (m, 6H), 1.95-2.40 (m, 5H).

Example 6

Synthesis of (2S,3R)—N-(2-((3-pyridinyl)methyl)-1-azabicyclo[2.2.2]oct-3-yl)benzofuran-2-carboxamide hemigalactarate salt Galactaric (mucic) acid (36.3 mg, 0.173 mmol) was added to a solution of (2S,3R)—N-(2-((3-pyridinyl)methyl)-1-azabicyclo[2.2.2]oct-3-yl)benzofuran-2-carboxamide (125 mg, 0.346 mmol) in hot ethanol (1 mL). The mixture was refluxed as water (8 drops) was added; then the hot mixture was filtered through a cotton plug, which was subsequently rinsed with ethanol (1 mL). Cooling failed to give a precipitate. The volatiles were removed by rotary evaporation, and the residue (white foam) was triturated with isopropanol (discarded), and the remaining solid dissolved in refluxing acetone/water (4 mL of 7:1). Slow cooling to 5° C. produced a white solid, which was filtered off, washed with isopropanol (3×1 mL), and dried under high vacuum. This left 118 mg (73% yield) fine white plates, mp 134-139° C. $^1$H NMR (300 MHz, D$_2$O) δ 8.29 (s, 1H), 7.78 (d, 1H), 7.62 (d, 1H), 7.54 (d, 1H), 7.35 (m, 2H), 7.18 (t, 1H), 7.10 (s, 1H), 6.98 (m, 1H), 4.08 (s, 1H, galactaric acid), 3.98 (d, 1H), 3.77 (s, 1H, galactaric acid), 3.66 (m, 1H), 3.35 (m, 1H), 2.95-3.30 (m, 4H), 1.65-2.05 (m, 5H).

Example 7

Synthesis of (2S,3R)—N-(2-((3-pyridinyl)methyl)-1-azabicyclo[2.2.2]oct-3-yl)benzofuran-2-carboxamide D-tartrate salt Tartaric acid (25.6 mg, 0.173 mmol) was added to a solution of (2S,3R)—N-(2-((3-pyridinyl)methyl)-1-azabicyclo [2.2.2]oct-3-yl)benzofuran-2-carboxamide (125 mg, 0.346 mmol) in hot ethanol (1 mL). The resulting solution was slowly cooled to ambient temperature. No solids precipitated, so the solution was concentrated to give a white foam. Attempts to crystallize in isopropanol failed. The foam was dissolved in methanol and another half-equivalent of tartaric acid (25.6 mg, 0.173 mmol) was added. The mixture was concentrated to give a white foam, which would not crystallize from mixtures of methanol and isopropanol. The concentrated material (mixture of solid and gummy liquid) was then slurried in ethyl acetate (1 mL), producing a white solid. This was isolated by filtration (ethyl acetate wash) and drying in a vacuum oven (18 h at 40° C.), to give 141 mg (79.7% yield) of the mono stoichiometry salt (NMR), mp 136-140° C. Chiral LC analysis gave a purity of 98.1% (270 nm). $^1$H NMR (300 MHz, D$_2$O) δ 8.50 (s, 1H), 8.01 (d, 1H), 7.86 (d, 1H), 7.75 (d, 1H), 7.56 (m, 2H), 7.38 (t, 1H), 7.32 (s, 1H), 7.21 (t, 1H), 4.34

(s, 2H, tartaric acid), 4.26 (d, 1H), 3.95 (m, 1H), 3.64 (m, 2H), 3.15-3.55 (m, 4H), 1.90-2.30 (m, 5H).

Example 8

Synthesis of (2S,3R)—N-(2-((3-pyridinyl)methyl)-1-azabicyclo[2.2.2]oct-3-yl)benzofuran-2-carboxamide methanesulfonate salt Methaesulfonic acid (33.2 mg, 0.346 mmol) was added to a solution of (2S,3R)—N-(2-((3-pyridinyl)methyl)-1-azabicyclo[2.2.2]oct-3-yl)benzofuran-2-carboxamide (125 mg, 0.346 mmol) in hot ethanol (1 mL). Cooling failed to produce a precipitate. The mixture was refluxed, and the hot mixture was filtered through a cotton plug, which was subsequently rinsed with methanol (1 mL). The volatiles were removed by rotary evaporation, and the residue (light yellow foam) was dissolved in hot isopropanol (1 mL). Again, cooling failed to give a precipitate. The isopropanol was evaporated, and the residue was slurried in acetone (1 mL). Filtration and vacuum oven drying (18 h at 50° C.) gave 146 mg (92.5% yield) of light beige solid, mp 240-243° C. $^1$H NMR (300 MHz, D$_2$O) δ 8.32 (s, 1H), 7.82 (d, 1H), 7.66 (d, 1H), 7.57 (d, 1H), 7.38 (m, 2H), 7.20 (m, 1H), 7.12 (s, 1H), 7.01 (m, 1H), 4.09 (d, 1H), 3.75 (m, 1H), 3.47 (m, 2H), 3.00-3.40 (m, 4H), 2.67 (s, 3H, methanesulfonic acid), 1.75-2.15 (m, 5H).

Example 9

Synthesis of (2S,3R)—N-(2-((3-pyridinyl)methyl)-1-azabicyclo[2.2.2]oct-3-yl)benzofuran-2-carboxamide D-mandelate salt D-Mandelic acid (52.6 mg, 0.346 mmol) was added to a solution of (2S,3R)—N-(2-((3-pyridinyl)methyl)-1-azabicyclo[2.2.2]oct-3-yl)benzofuran-2-carboxamide (125 mg, 0.346 mmol) in hot ethanol (1 mL). Dilution with ethyl acetate (4 mL) and cooling failed to produce a precipitate. The volatiles were removed by rotary evaporation, and the residue (white foam) was dissolved in hot isopropanol (0.5 mL). Cooling to 5° C. produced white crystals which were collected by suction filtration. Vacuum oven drying (18 h at 45° C.) gave 111 mg (62.4% yield) of light beige solid, mp 188.5-193° C. $^1$H NMR (300 MHz, D$_2$O) δ 8.33 (s, 1H), 7.83 (s, 1H), 7.67 (d, 1H), 7.60 (d, 1H), 7.27 (m, 8H, includes mandelic acid), 7.12 (s, 1H), 7.01 (m, 1H), 4.85 (s, 1H, mandelic acid), 4.10 (d, 1H), 3.75 (m, 1H), 3.48 (m, 2H), 3.00-3.40 (m, 4H), 1.75-2.15 (m, 5H).

Example 10

Synthesis of (2S,3R)—N-(2-((3-pyridinyl)methyl)-1-azabicyclo[2.2.2]oct-3-yl)benzofuran-2-carboxamide R-camphorsulfonate salt R-10-Camphorsulfonic acid (80.3 mg, 0.346 mmol) was added to a solution of (2S,3R)—N-(2-((3-pyridinyl)methyl)-1-azabicyclo[2.2.2]oct-3-yl)benzofuran-2-carboxamide (125 mg, 0.346 mmol) in hot ethanol (1 mL). Cooling failed to deposit any precipitate. The volatiles were removed by rotary evaporation, and the residue (white foam) was dissolved in hot isopropanol (0.5 mL). Cooling to 5° C. produced a few white crystals and a milky suspension. Scratching the sides of the flask with a spatula eventually transformed the mixture into a thick mass of fine white crystals. Another 0.5 mL of isopropanol was added, and the crystals were collected by suction filtration. Vacuum oven drying (5 h at 70° C., followed by 2 h at 110° C.) gave 193 mg (93.8% yield) of white solid, mp 149.5-156° C. $^1$H NMR (300 MHz, D$_2$O) δ 8.30 (s, 1H), 7.79 (d, 1H), 7.64 (d, 1H), 7.55 (d, 1H), 7.36 (m, 2H), 7.18 (m, 1H), 7.11 (s, 1H), 6.99 (m, 1H), 4.07 (d, 1H), 3.73 (m, 1H), 3.45 (m, 2H), 3.95-3.35 (m, 5H, includes camphorsulfonic acid), 2.64 (d, 1H, camphorsulfonic acid), 2.22 (m, 2H), 1.70-2.10 (m, 8H, includes camphorsulfonic acid), 1.45 (m, 1H, camphorsulfonic acid), 1.25 (m, 1H, camphorsulfonic acid), 0.85 (s, 3H, camphorsulfonic acid), 0.68 (s, 3H, camphorsulfonic acid).

Example 11

Synthesis of (2S,3R)—N-(2-((3-pyridinyl)methyl)-1-azabicyclo[2.2.2]oct-3-yl)benzofuran-2-carboxamide S-camphorsulfonate salt S-10-Camphorsulfonic acid (80.3 mg, 0.346 mmol) was added to a solution of (2S,3R)—N-(2-((3-pyridinyl)methyl)-1-azabicyclo[2.2.2]oct-3-yl)benzofuran-2-carboxamide (125 mg, 0.346 mmol) in hot ethanol (1 mL). Dilution with ethyl acetate (4 mL) and cooling failed to deposit any precipitate. The volatiles were removed by rotary evaporation, and the residue (white foam) was dissolved in hot isopropanol (1.5 mL). Cooling to 5° C. produced white crystals. The mixture was concentrated to ~0.5 mL and cooled again to 5° C. The solid was then collected by suction filtration and vacuum dried, initially 18 h at 45° C., but then at successively higher temperatures (finally at 110° C.) to remove residual isopropanol. This provided 143 mg (69.7% yield) of white solid, mp 153.5-157° C. $^1$H NMR (300 MHz, D$_2$O) δ 8.29 (s, 1H), 7.79 (d, 1H), 7.63 (d, 1H), 7.54 (d, 1H), 7.34 (m, 2H), 7.18 (m, 1H), 7.10 (s, 1H), 6.99 (m, 1H), 4.05 (d, 1H), 3.73 (m, 1H), 3.44 (m, 2H), 3.95-3.35 (m, 5H, includes camphorsulfonic acid), 2.67 (d, 1H, camphorsulfonic acid), 2.23 (m, 2H), 1.70-2.10 (m, 8H, includes camphorsulfonic acid), 1.46 (m, 1H, camphorsulfonic acid), 1.25 (m, 1H, camphorsulfonic acid), 0.84 (s, 3H, camphorsulfonic acid), 0.64 (s, 3H, camphorsulfonic acid).

Using procedures similar to those reported above (examples 3-11), several other salt forms were characterized. The results of these preparations are reported in examples 12-14.

Example 12

Synthesis of (2S,3R)—N-(2-((3-pyridinyl)methyl)-1-azabicyclo[2.2.2]oct-3-yl)benzofuran-2-carboxamide sulfate salt A sulfate salt was precipitated from a mixture of isopropyl acetate and water. MP 278° C. $^1$H NMR (400 MHz, DMSO-d$_6$) δ 9.28 (broad s, 1H, amide), 8.56 (dd, 1H), 8.24 (t, 1H), 7.77 (d, 1H), 7.74 (d, 1H), 7.60 (s, 1H), 7.40 (m, 2H), 7.35 (s, 1H), 7.21 (m, 1H), 4.21 (m, 1H), 3.93 (m, 2H), 3.10-3.60 (m, 5H), 2.05 (m, 3H), 1.92 (m, 1H), 1.73 (m, 1H).

Example 13

Synthesis of (2S,3R)—N-(2-((3-pyridinyl)methyl)-1-azabicyclo[2.2.2]oct-3-yl)benzofuran-2-carboxamide ketoglutarate salt An α-ketoglutarate salt was precipitated from isopropyl acetate. MP 177° C. $^1$H NMR (400 MHz, DMSO-d$_6$) δ 8.64 (s, 1H, amide), 8.50 (d, 1H), 8.20 (d, 1H), 7.74 (d, 1H), 7.70 (d, 1H), 7.60 (m, 1H), 7.45 (m, 1H), 7.32 (m, 2H), 7.18 (m, 1H), 4.10 (m, 1H), 3.78 (m, 2H), 3.00-3.45 (m, 5H), 2.81 (m, 2H, ketoglutaric acid), 2.41 (m, 2H, ketoglutaric acid), 1.96 (m, 3H), 1.83 (m, 1H), 1.60 (m, 1H).

Example 14

Synthesis of (2S,3R)—N-(2-((3-pyridinyl)methyl)-1-azabicyclo[2.2.2]oct-3-yl)benzofuran-2-carboxamide hippurate salt A hippurate salt was precipitated from acetone (too hygroscopic to obtain melting point). $^1$H NMR (400 MHz, DMSO-$d_6$) δ 8.79 (s, 1H, amide), 8.56 (d, 1H), 8.44 (s, 1H, hippuric acid), 8.29 (m, 1H), 7.87 (m, 2H, hippuric acid), 7.76 (d, 1H), 7.65 (m, 1H), 7.54 (m, 1H), 7.49 (m, 4H, includes hippuric acid), 7.34 (m, 2H), 7.21 (m, 1H), 3.91 (m, 1H), 3.74 (m, 2H), 3.00-3.50 (m, 5H), 2.80 (m, 2H, hippuric acid), 1.79 (m, 2H), 1.60 (m, 2H), 1.30 (m, 1H).

Example 15

Isolation of (2R,3R)- and (2S,3S)—N-(2-((3-pyridinyl)methyl)-1-azabicyclo[2.2.2]oct-3-yl)benzofuran-2-carboxamide and conversion to galactaric acid salts A sample of the supernatant from the isolation of (2S,3R)—N-(2-((3-pyridinyl)methyl)-1-azabicyclo[2.2.2]oct-3-yl)benzofuran-2-carboxamide p-toluenesulfonate (Example 2) was concentrated by rotary evaporation, adjusted pH 10 with 10% aqueous sodium hydroxide and extracted with dichloromethane. The dichloromethane extract was evaporated, and the residue (1.8 g) was dissolved in absolute ethanol (55 mL) containing 0.5% di-n-butylamine. This solution was injected, in 0.25 mL portions, onto a 25 cm×2.1 cm Chiralpak® AD chiral HPLC column, eluting with 60:40:0.2 hexane/ethanol/di-n-butylamine (flow rate=30 mL/min), monitored at 270 nm. Isolation of the effluent eluting at ~7.5 min and that eluting at ~13.5 min gave, after evaporation of the solvent, 0.48 g (98% chiral purity) and 0.47 g (99% chiral purity) respectively of colorless oil. The two NMR spectra were identical. $^1$H NMR (300 MHz, CDCl$_3$) δ 8.49 (s, 1H), 8.45 (d, 1H), 7.74 (d, 1H), 7.52 (m, 4H), 7.35 (t, 1H), 7.20 (dd, 1H), 7.05 (d, 1H), 4.55 (dt, 1H), 3.43 (m, 1H), 3.22 (m, 1H), 2.90 (m, 5H), 2.09 (m, 1H), 1.88 (m, 4H).

A warm solution of each free base samples in absolute ethanol (10 mL) was treated with one equivalent of galactaric acid. The resulting mixtures were heated at 75° C. for 5 min and cooled, with stirring, to ambient temperature. The resulting solids were collected by suction filtration and vacuum dried, giving 0.65 g (87% yield) and 0.62 g (85% yield) respectively of white granular solid (mp 200-205° C. in each case). $^1$H NMR (300 MHz, D$_2$O) δ 8.38 (s, 1H), 8.28 (d, 1H), 7.94 (d, 1H), 7.70 (d, 1H), 7.59 (d, 1H), 7.48 (t, 1H), 7.40 (m, 1H), 7.32 (m, 2H), 4.42 (m, 1H), 4.21 (s, 2H), 3.87 (s, 2H), 3.68 (m, 1H), 3.35 (m, 6H), 2.25 (m, 2H), 2.02 (m, 3H).

Example 16

Synthesis of (2R,3R)—N-(2-((3-pyridinyl)methyl)-1-azabicyclo[2.2.2]oct-3-yl)benzofuran-2-carboxamide p-chlorobenzoate salt Solid p-chlorobenzoic acid (46.8 mg, 0.299 mmol) was added in one portion to a solution of the earlier eluting isomer of N-(2-((3-pyridinyl)methyl)-1-azabicyclo[2.2.2]oct-3-yl]benzofuran-2-carboxamide from Example 15 (108 mg, 0.299 mmol) in acetone (10 mL). This mixture was warmed to near reflux for 30 min and cooled to ambient temperature. No precipitate formed, so the solution was concentrated to about 20% of its former volume (hot plate), at which point crystals began to form. The mixture was cooled and diluted with isopropanol (2 mL). This mixture was concentrated by slow evaporation of solvent at ambient temperature, and the resulting solids were collected and dried. This produced 145 mg (94% yield) of light yellow crystals, mp 150-152° C. $^1$H NMR (300 MHz, CDCl$_3$) δ 8.49 (s, 1H), 8.38 (d, 1H), 7.93 (d, 2H, p-chlorobenzoic acid), 7.67 (m, 2H), 7.57 (d, 1H), 7.45 (m, 1H), 7.36 (d, 2H, p-chlorobenzoic acid), 7.30 (m, 1H), 7.27 (s, 1H), 7.16 (m, 1H), 7.00 (d, 1H, amide), 6.90 (broad s, quaternary ammonium), 4.62 (m, 1H), 3.85 (dd, 1H), 3.36 (m, 1H), 2.95-3.25 (m, 5H), 2.16 (s, 1H), 1.70-2.10 (m, 4H).

Figure 11A:
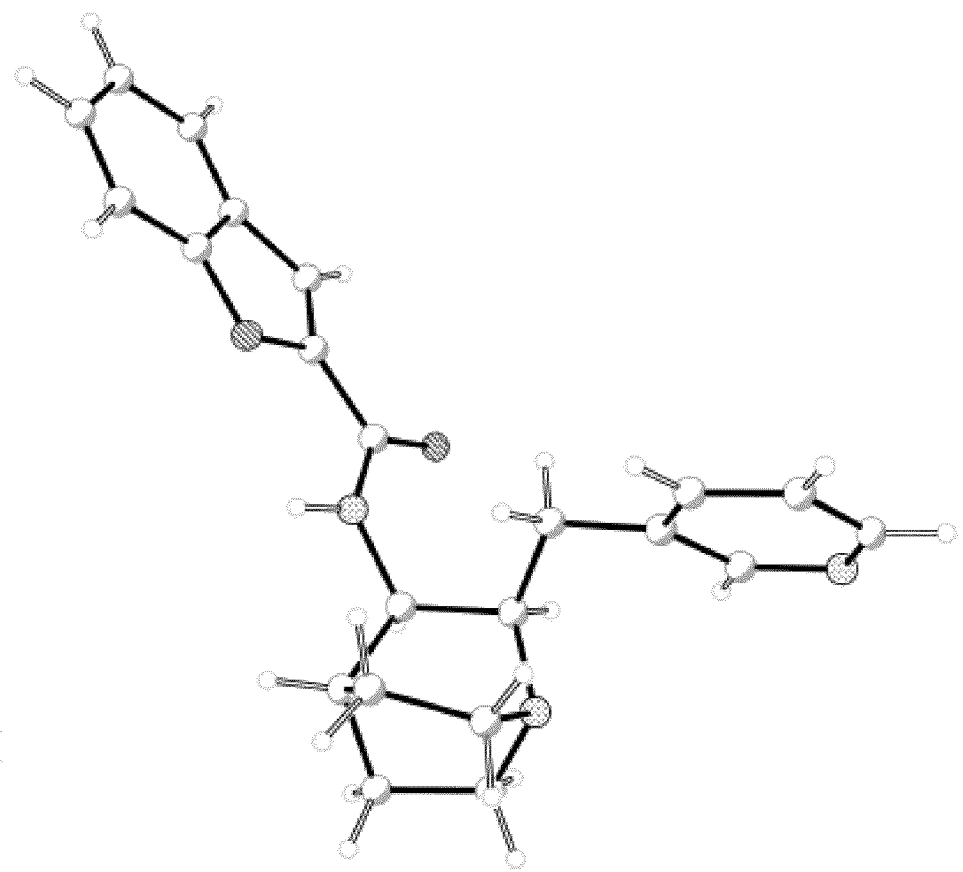
FIG. 11A illustrates the results of the x-ray crystallographic analysis of (2R,3R)—N-(2-((3-pyridinyl)methyl)-1-azabicyclo [2.2.2]oct-3-yl)benzofuran-2-carboxamide p-chlorobenzoate, establishing the absolute stereochemistry of this material.
Figure 11B:
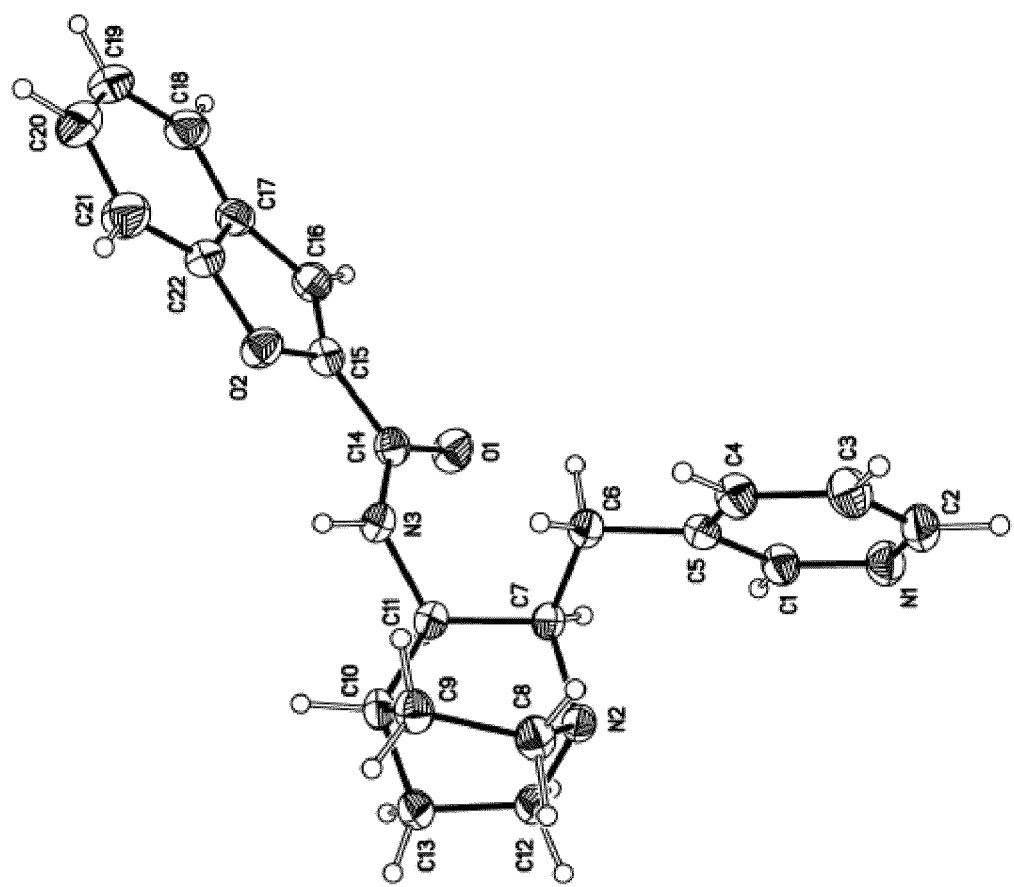
FIG. 11B illustrates the results of the x-ray crystallographic analysis of (2R,3R)—N-(2-((3-pyridinyl)methyl)-1-azabicyclo [2.2.2]oct-3-yl)benzofuran-2-carboxamide p-chlorobenzoate, establishing the absolute stereochemistry of this material, depicted with a numbering scheme for reference.

X-ray crystallographic analysis of this sample revealed its absolute stereochemistry to be 2R,3R (see FIGS. 11A and 11B). The later eluting isomer in Example 15 thus by elimination, has 2S,3S absolute configuration.

Example 17

Chiral Chromatographic Method for Analysis of the Stereoisomers

Figure 12:
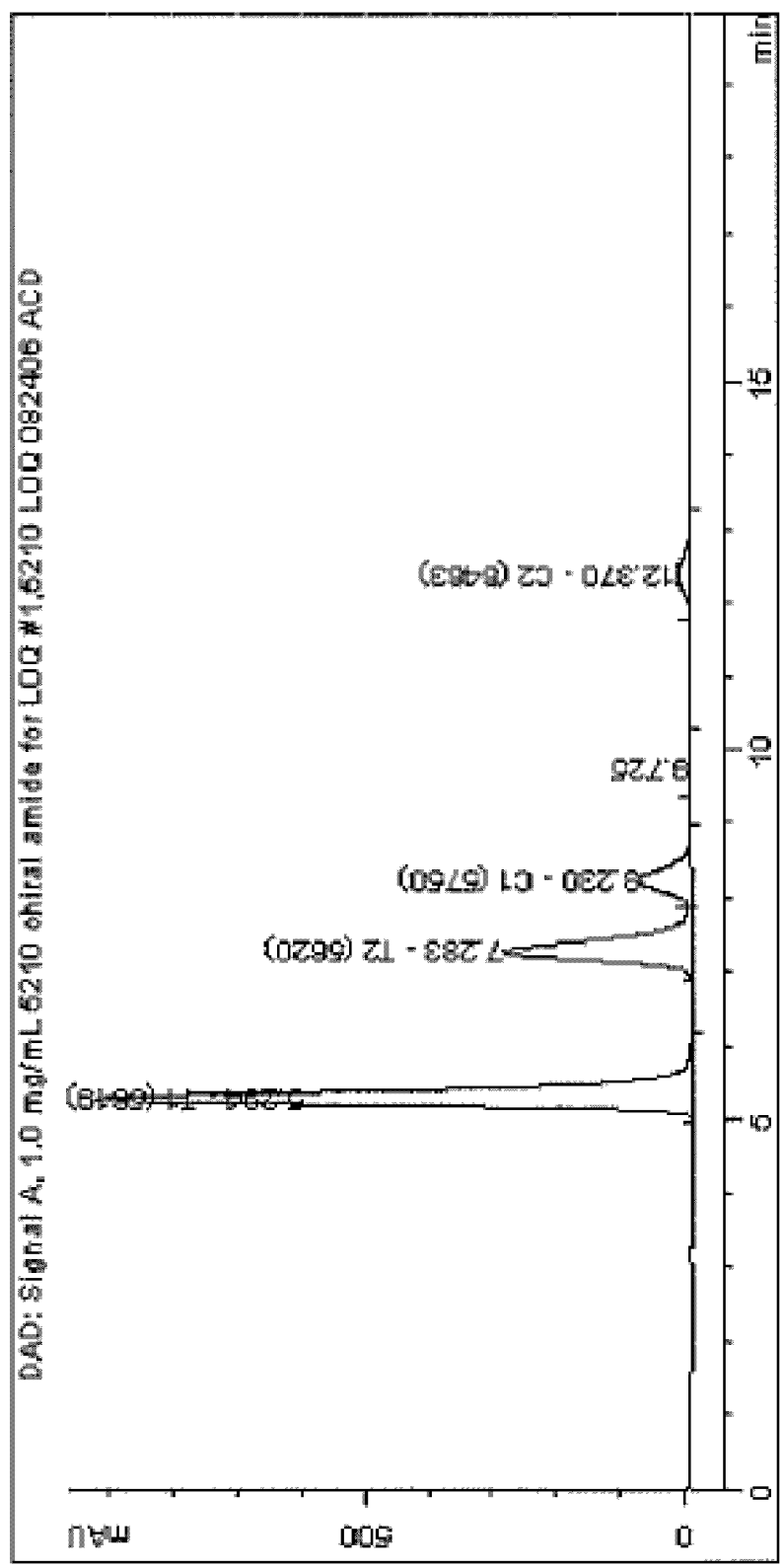
FIG. 12 illustrates a full chromatogram characterizing four stereoisomers of N-(2-((3-pyridinyl)methyl)-1-azabicyclo [2.2.2]oct-3-yl)benzofuran-2-carboxamide, where the 2S,3R demonstrates a peak at retention time of 5.3 minutes, the 2R,3S demonstrates a peak at retention time of 7.3 minutes, the 2R,3R demonstrates a peak at retention time of 8.2 minutes, and the 2S,3S demonstrates a retention time of 12.4 minutes. As described herein, the mobile phase required analysis to provide adequate resolution, resulting in a composition of 60:40:0.2 hexanes:ethanol:di-n-butylamine at 1.0 ml/min, with a column temperature of 20° C., and UV detection at 270 nm.

Generation of a chiral chromatographic method for separation of the four stereoisomers, one from another, proved very challenging. The initial attempts (using hexane/isopropanol/triethylamine mobile phase) resulted in overlapping peaks and less than optimal peak shapes. Switching from isopropanol to ethanol and from triethylamine to di-n-butylamine improved resolution and peak shape and shortened the run time. The details of the method are as follows:

Analytical Column: Chiralpak® AD (250×4.6 mm, 5 urn)
Mobile Phase: 60:40:0.2 hexanes/ethanol/di-n-butylamine
Injection Volume: 10 μL
Flow Rate: 1.0 mL per minute
Temperature: 20° C.
Detection: UV at 270 nm
Total Run Time: ~25 minutes
Elution Order (RT): 2S,3R (5.3 min); 2R,3S (7.3 min); 2R,3R (8.3 min); 2S,3S (12.1 min) A representative chromatogram of the stereoisomer analogues is shown in FIG. 12.

Example 18

XRPD

XRPD analysis was performed for several salt samples herein described. Diffraction patterns for the hydrocloride (FIG. 13) and the tosylate (FIG. 14) salts are provided.
X-Ray Powder Diffraction (XRPD)

X-Ray Powder Diffraction patterns were collected either or both of two instruments. Some were collected on a Siemens D5000 diffractometer using CuKα radiation (40 kV, 40 mA), 0-0 goniometer, V20 divergence and receiving slits, a graphite secondary monochromator and a scintillation counter. The instrument was performance checked using a certified Corundum standard (NIST 1976). Samples run under ambient conditions were prepared as flat plate specimens using powder as received. Approximately 35 mg of the sample was gently packed into a cavity cut into polished, zero-background (510) silicon wafer. The sample was rotated in its own plane during analysis, scanning from 2° to 42° in steps of 0.05° at 4 seconds per step, using CuKα1 (λ=1.5406 Å).

Some X-Ray Powder Diffraction patterns were collected on a Bruker AXS C2 GADDS diffractometer using CuKα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence (i.e. the effective size of the X-ray beam on the sample) was approximately 4 mm. A θ-θ continuous scan mode was employed with a sample-detector distance of 20 cm which gives an effective 2θ range of 3.2°-30.0°. Typically the sample would be exposed to the X-ray beam for 120 seconds. Samples run under ambient conditions were prepared as flat plate specimens using powder as received without grinding. Approximately 1-2 mg of the sample was lightly pressed on a silicon wafer to obtain a flat surface. Samples run under non-ambient conditions were mounted on a silicon wafer with heat-conducting compound. The sample was then heated to the appropriate temperature at ca. 10° C./min and subsequently held isothermally for about 5 min before data collection was initiated.

Differential Scanning Calorimetry (DSC)

DSC data were collected on a TA Instruments Q1000 equipped with a 50 position auto-sampler. The instrument was calibrated for energy and temperature calibration using certified indium. Typically 0.5-1.5 mg of each sample, in a pin-holed aluminium pan, was heated at 10° C./min from 25° C. to 175-200° C. A nitrogen purge at 30 mL/min was maintained over the sample.

Thermo-Gravimetric Analysis (TGA)

TGA data were collected on a TA Instruments Q500 TGA, equipped with a 16 position auto-sampler. The instrument was temperature calibrated using certified Alumel. Typically 5-10 mg of each sample was loaded onto a pre-tared platinum crucible and aluminium DSC pan, and was heated at 10° C./min from ambient temperature to 350° C. A nitrogen purge at 60 mL/min was maintained over the sample.

Polarized Light Microscopy (PLM)

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a λ false-color filter.

Hot Stage Microscopy (HSM)

Hot Stage Microscopy was carried out using a Leica LM/DM polarized light microscope combined with a Mettler-Toledo MTFP82HT hot-stage and a digital video camera for image capture. A small amount of each sample was placed onto a glass slide with individual particles separated as well as possible. The sample was viewed with appropriate magnification and partially polarized light, coupled to a λ false-color filter, whilst being heated from ambient temperature typically at 10° C./min.

Gravimetric Vapor Sorption (GVS)

Sorption isotherms were determined on either or both of two instruments. Some were experiments were run using a VTI Corporation SGA-100 moisture sorption analyzer, controlled by VTI FlowSystem 4 software. The sample temperature was maintained at 25° C. with the aid of a Polyscience constant temperature bath. The humidity was controlled by mixing streams of dry and wet nitrogen. The weight change as a function of % RH was monitored using a Cahn Digital Recording Balance D-200 with an accuracy of +/−0.0001 g.

Typically a 10-20 mg sample was placed on the tared balance pan under ambient conditions. The sample was dried at 50° C. for 1 h. The standard adsorption isotherm was performed at 25° C. at 5% RH intervals over a 5-95% RH range, and the desorption isotherm was similarly done at 25° C. at 5% RH intervals over a 95-5% RH range. Sample equilibration criteria included 0.0100 wt % in 5 min or a maximum equilibration time of 180 min for each % RH data point.

Some sorption isotherms were obtained using a Hiden IGASorp moisture sorption analyser, controlled by CFRSorp software. The sample temperature was maintained at 25° C. by a Huber re-circulating water bath. The humidity was controlled by mixing streams of dry and wet nitrogen, with a total flow rate of 250 mL/min. The relative humidity was measured by a calibrated Vaisala RH probe (dynamic range of 0-95% RH), located near the sample. The weight change, (mass relaxation) of the sample as a function of % RH was constantly monitored by the microbalance (accuracy ±0.001 mg). Typically 10-20 mg of sample was placed in a tared mesh stainless steel basket under ambient conditions. The sample was loaded and unloaded at 40% RH and 25° C. (typical ambient conditions). A moisture sorption isotherm was performed as outlined below (2 scans giving 1 complete cycle). The standard isotherm was performed at 25° C. at 10% RH intervals over a 0-90% RH range.

| GVS Generic method parameters | |
|---|---|
| Parameters | Values |
| Adsorption - Scan 1 | 40-90 |
| Desorption/Adsorption - Scan 2 | 85-Dry, Dry-40 |
| Intervals (% RH) | 10 |
| Number of Scans | 2 |
| Flow rate (mL/min) | 250 |
| Temperature (° C.) | 25 |
| Stability (° C./min) | 0.05 |
| Minimum Sorption Time (hours) | 1 |
| Maximum Sorption Time (hours) | 4 |
| Mode | AF2 |
| Accuracy (%) | 98 |

The software uses a least squares minimization procedure together with a model of the mass relaxation, to predict an asymptotic value. The measured mass relaxation value must be within 5% of that predicted by the software, before the next % RH value is selected. The minimum equilibration time was set to 1 h and the maximum to 4 h. Typically, samples were recovered after completion of the isotherm and re-analyzed by XRPD.

Water Determination by Karl Fischer (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determination were made.

Thermodynamic Aqueous Solubility by HPLC

Aqueous solubility was determined by suspending sufficient compound in 0.25 mL of water to give a maximum final concentration of ≥10 mg/mL of the parent free-form of the compound. The suspension was equilibrated at 25° C. for 24 h, and then the pH was measured. The suspension was then filtered through a glass fiber C filter into a 96 well plate. The filtrate was then diluted by a factor of 101. Quantitation was by HPLC with reference to a standard solution of approximately 0.1 mg/mL in DMSO. Different volumes of the standard, diluted and undiluted sample solutions were injected. The solubility was calculated using the peak areas determined by integration of the peak found at the same retention time as the principal peak in the standard injection. If there was sufficient solid in the filter plate, the XRPD was collected.

| Generic method details for thermodynamic aqueous solubility method | |
|---|---|
| Type of method: | Reverse phase with gradient elution |
| Column: | Phenomenex Luna, C18 (2) 5 µm, 50 × 4.6 mm |
| Column Temperature (° C.): | 25 |
| Injection (µL): | 5, 8 and 50 |
| Detection: Wavelength, Bandwidth (nm): | 260, 80 |
| Flow Rate (mL/min): | 2 |
| Phase A: | 0.1% TFA in water |
| Phase B: | 0.085% TFA in acetonitrile |

| | Time (min) | % Phase A | % Phase B |
|---|---|---|---|
| Timetable: | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Chemical Purity by HPLC

Purity analysis was performed on an Agilent HP1100 series system equipped with a diode array detector and using ChemStation software v9. One of the two methods detailed below was used.

| Method 1 | |
|---|---|
| Type of method | Reverse phase with gradient elution |
| Column: | Kromasil 5 µm C18, 150 × 4.6 mm |
| Column Temperature (° C.): | 26 |
| Injection (µL): | 10 |
| Detection: Wavelength, Bandwidth(nm): | 302, 8 |
| Flow Rate (mL/min): | 1.0 |
| Phase A: | 0.0256M KH2PO4 + 0.02M 1-hexane sulphonic acid Na salt |
| Phase B: | Acetonitrile |

| | Time (min) | % Phase A | % Phase B |
|---|---|---|---|
| Timetable: | 0 | 90 | 10 |
| | 8 | 90 | 10 |
| | 40 | 10 | 90 |
| | 41 | 90 | 10 |
| | 49 | 90 | 10 |
| | 50 | 90 | 10 |

| Method 2 | |
|---|---|
| Type of method | Reverse phase with gradient elution |
| Column: | Phenomenex Luna C18 (2), 150 × 4.6 mm, 5 µm |
| Column Temperature (° C.): | 25 |
| Injection (µL): | 5 |
| Detection: Wavelength, Bandwidth(nm): | 255, 90 |
| Flow Rate (mL/min): | 1 |
| Phase A: | 0.1% TFA in water |
| Phase B: | 0.085% TFA in acetonitrile |

| | Time (min) | % Phase A | % Phase B |
|---|---|---|---|
| Timetable: | 0 | 95 | 5 |
| | 25 | 5 | 95 |
| | 25.2 | 95 | 5 |
| | 30 | 95 | 5 |

Ion Chromatography

Data were collected on a Metrohm 861 Advanced Compact IC using IC Net software v2.3. Samples were prepared as 1000 ppm stocks in water. Where sample solubility was low, a suitable co-solvent such as DMSO was used. Samples were diluted to 50 ppm or 100 ppm with an appropriate solvent prior to testing. Quantification was achieved by comparison with standard solutions of known concentration of the ion being analyzed.

| Ion Chromatography method for anions | |
|---|---|
| Type of method | Anion exchange |
| Column: | Metrosep A Supp 5-250 (4.0 × 250 mm) |
| Column Temperature (° C.): | Ambient |
| Injection (µL): | 20 |
| Detection: | Conductivity detector |
| Flow Rate (mL/min): | 0.7 |
| Eluent: | 3.2 mM sodium carbonate, 1.0 mM sodium hydrogen carbonate in water |

| Ion Chromatography method for cations | |
|---|---|
| Type of method | Cation exchange |
| Column: | Metrosep C 2-250 (4.0 × 250 mm) |
| Column Temperature (° C.): | Ambient |
| Injection (µL): | 20 |
| Detection: | Conductivity detector |
| Flow Rate (mL/min): | 1.0 |
| Eluent: | 4.0 mM Tartaric acid, 0.75 mM Dipicolinic acid in water |

Figure 13:
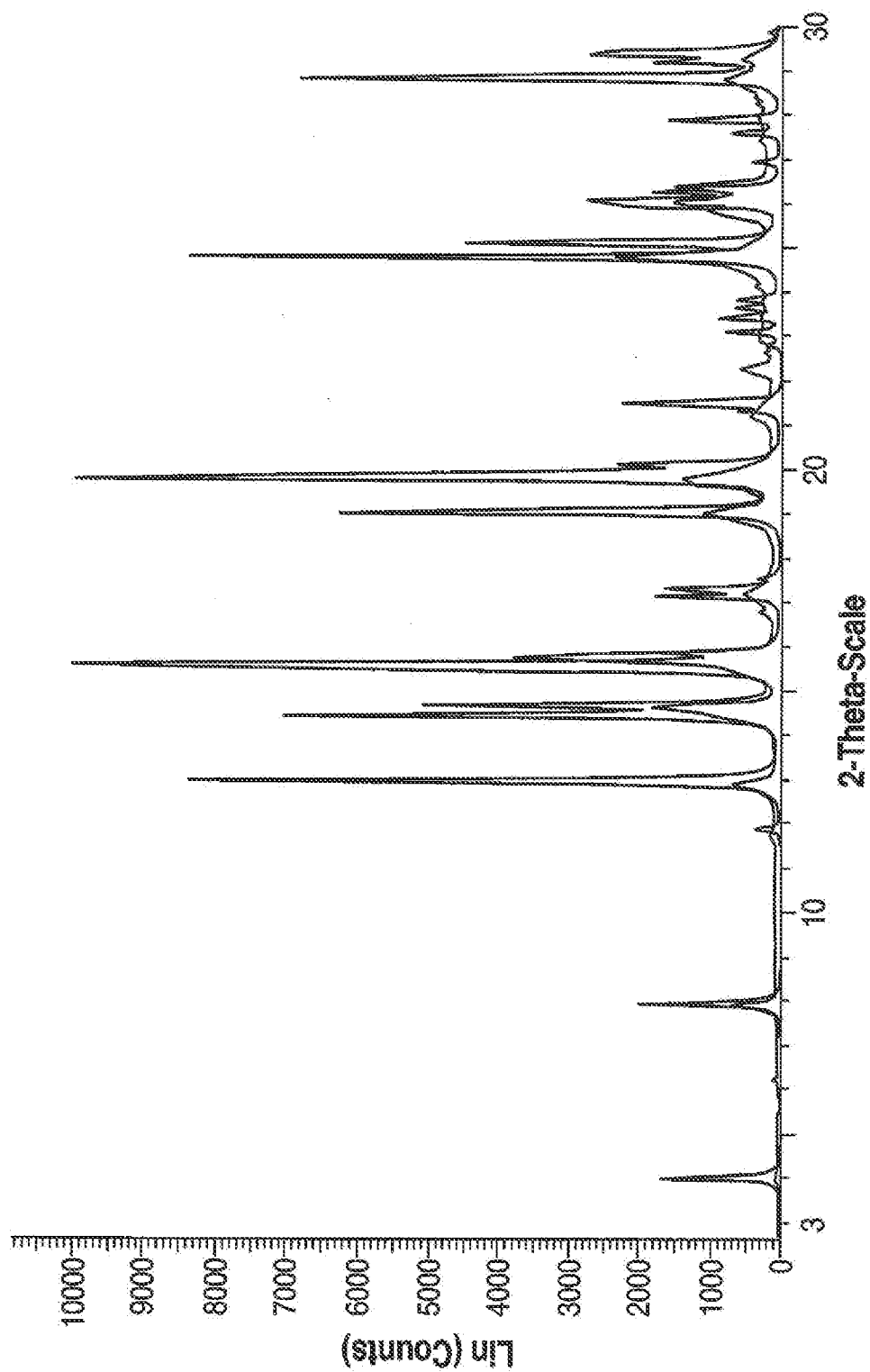
FIG. 13 is an XRPD of (2S,3R)—N-(2-((3-pyridinyl)methyl)-1-azabicyclo [2.2.2]oct-3-yl)benzofuran-2-carboxamide monohydrochloride illustrating both observed (lighter) and calculated (darker) patterns. Both patterns are in agreement in respect of 2θ values and minor difference in intensities and peak widths may be attributed to instrument resolution and preferred orientation effects. As described herein, further minor differences may be attributed to a temperature shift due to the observed data being collected at room temperature and calculated data from a structure at 120K.

Approximately 50 mg of (2S,3R)—N-(2-((3-pyridinyl)methyl)-1-azabicyclo [2.2.2]oct-3-yl)benzofuran-2-carboxamide hydrochloride was weighed into a glass vial and heated to 50° C. 100 µl portions of 1-butanmol/water (5 volume % water) were added to the solid until a clear solution was formed (500 µl total). The sample was stirred for 50° C. for 1 hour and observations were made. After heating at 50° C. for an hour the sample remained a clear solution and was cooled from 50° C. to 25° C. at a rate of 1.4° C. per hour. The sample remained a clear solution on cooling and was covered with parafilm, pin-holed, and left to evaporate at ambient temperature. After 2 weeks, large crystals were seen in the partially evaporated sample. FIG. 13 is an XRPD of (2S,3R)—N-(2-((3-pyridinyl)methyl)-1-azabicyclo [2.2.2]oct-3-yl)benzofuran-2-carboxamide monohydrochloride illustrating both observed (lighter) and calculated (darker) patterns.

Figure 10A:
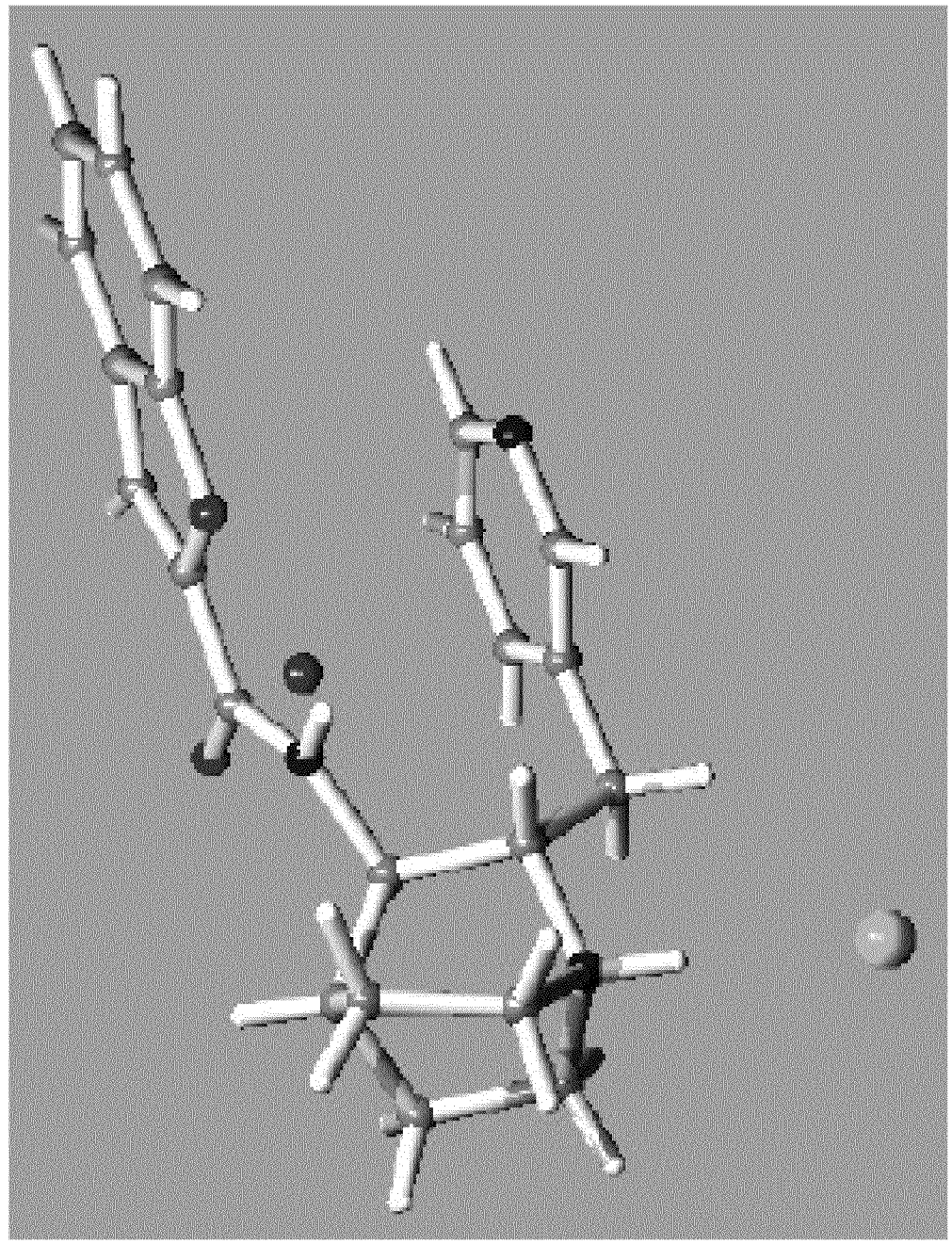
FIG. 10A illustrates the results of the x-ray crystallographic analysis of (2S,3R)—N-(2-((3-pyridinyl)methyl)-1-azabicyclo [2.2.2]oct-3-yl)benzofuran-2-carboxamide monohydrochloride, establishing the absolute stereochemistry of this material. The depicted compound is the partially hydrated hydrochloride salt, as shown with the fully ordered chloride anion and partially occupied molecule of water in the asymmetric unit.
Figure 10B:
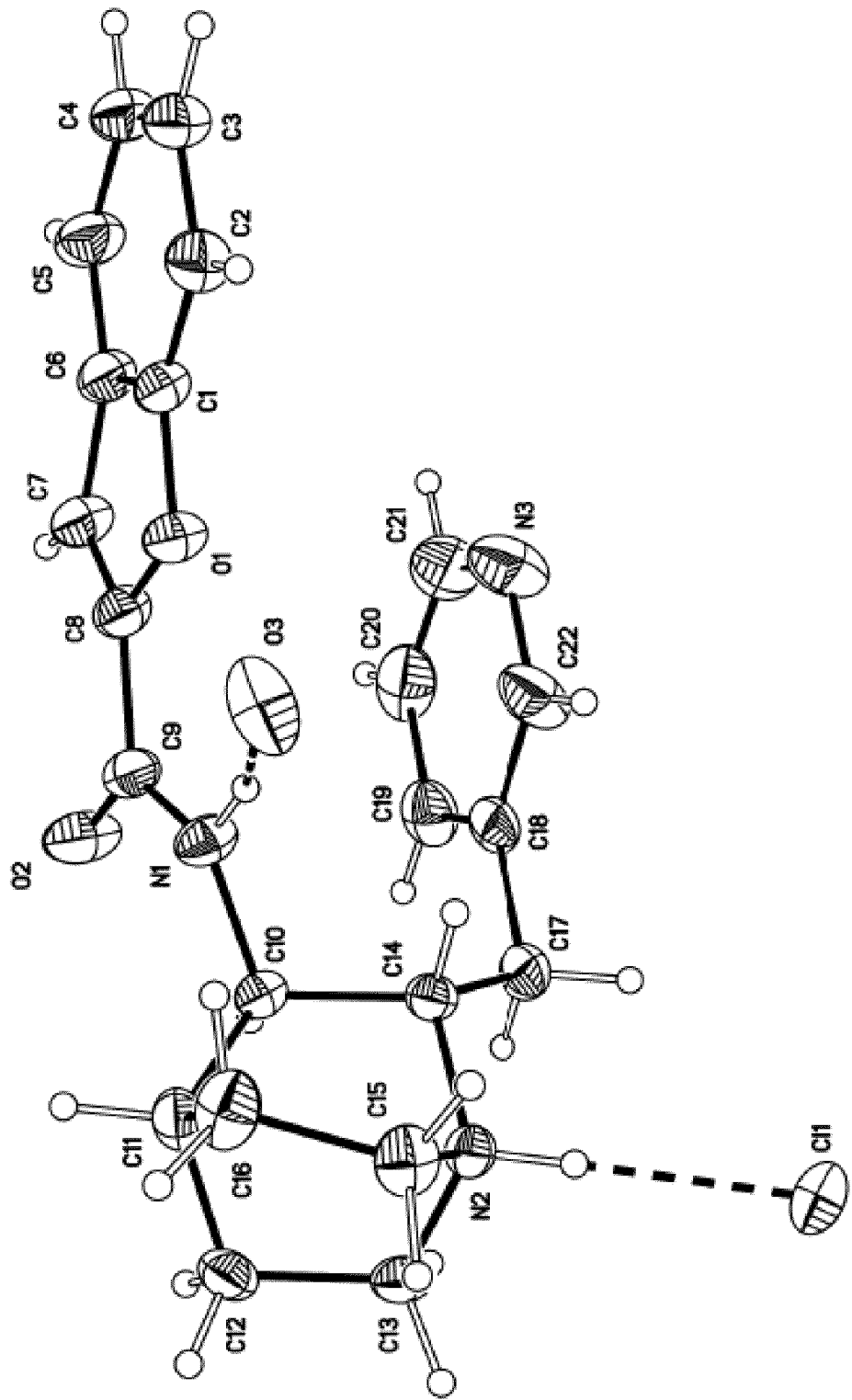
FIG. 10B illustrates the results of the x-ray crystallographic analysis of (2S,3R)—N-(2-((3-pyridinyl)methyl)-1-azabicyclo [2.2.2]oct-3-yl)benzofuran-2-carboxamide monohydrochloride, establishing the absolute stereochemistry of this material, depicted with a numbering scheme for reference. The view is looking down the crystallographic b-axis of the unit cell. The inter-molecular hydrogen bonds are shown as dashed lines.

The experimental pattern is from the sample of (2S,3R)—N-(2-((3-pyridinyl)methyl)-1-azabicyclo [2.2.2]oct-3-yl) benzofuran-2-carboxamide monohydrochloride while the calculated example is from the single crystal X-ray structure as herein described and depicted in FIGS. 10A and 10B. Both patterns are in agreement in respect of 20 values and minor difference in intensities and peak widths may be attributed to instrument resolution and preferred orientation effects. Further, minor differences may be attributed to a temperature shift due to the observed data being collected at room temperature and calculated data taken from a structure at 120K.

Figure 14:
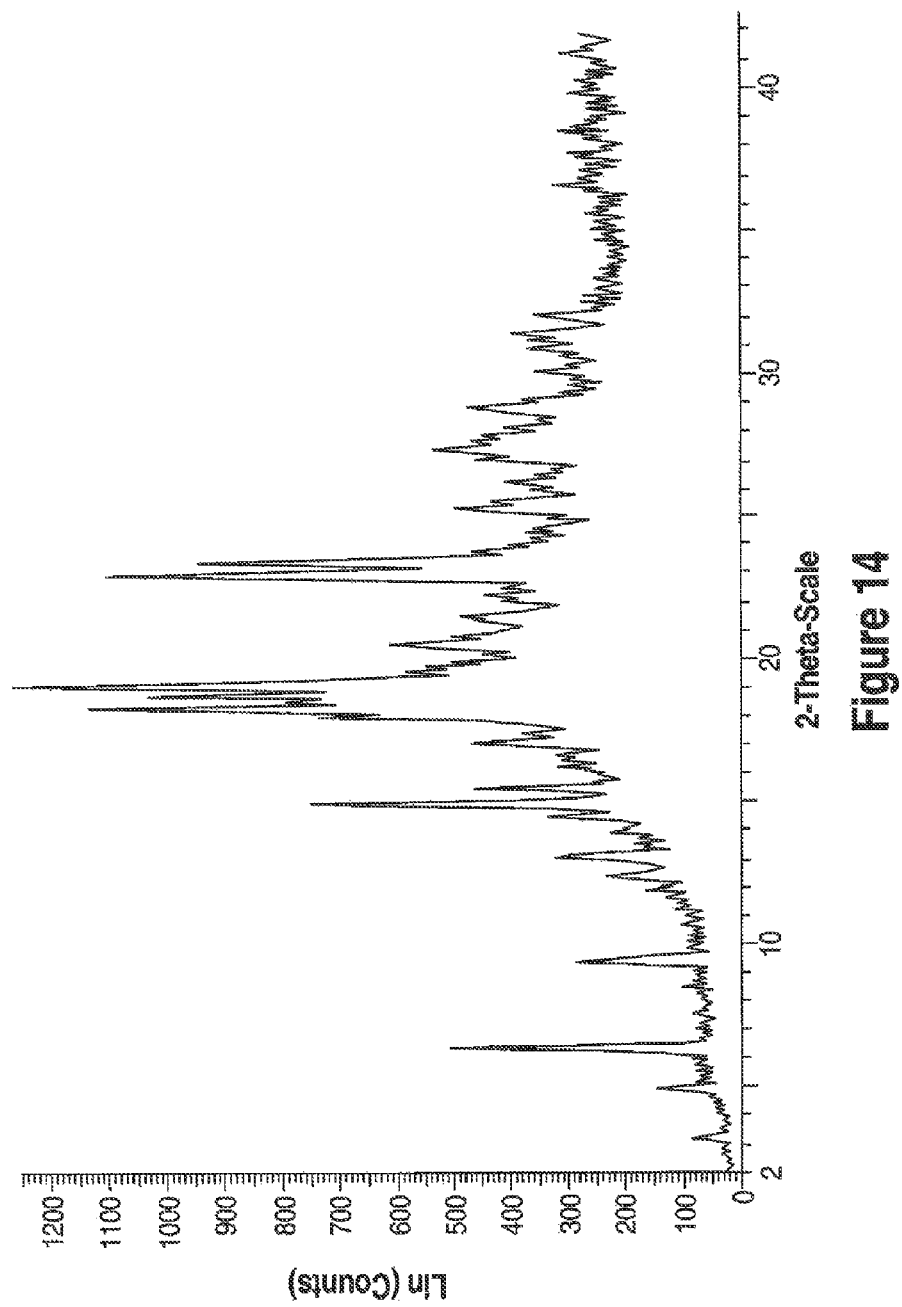
FIG. 14 is an XRPD of (2S,3R)—N-(2-((3-pyridinyl)methyl)-1-azabicyclo [2.2.2]oct-3-yl)benzofuran-2-carboxamide monotosylate.

The tosylate salt, specifically the crystalline mono salt, was confirmed and the diffraction pattern is shown in FIG. 14 using CuKα radiation (40 kV, 40 mA), 0-0 goniometer, V20 divergence and receiving slits, a graphite secondary monochromator, and a scintillation counter. An XRPD diffractogram of the tosylate salt after 1 week at 40° C./75% RH reveals a change but the sample is still Form 1. Likely, the change is due to a more hydrated form.

VII. Biological Assays

The ability of Compound A and its stereoisomers to bind to and modulate the function of various NNR subtypes was assessed as described in U.S. Pat. No. 6,953,855 to Mazurov et al, the contents of which are hereby incorporated by reference. Receptor selectivity profiling for Compound A (including 5HT$_3$ and muscarinic) was conducted by NovaScreen® Biosciences Corporation.

Electrophysiological measurement of α7 NNR response were taken in two expression systems: rat α7 NNR in mammalian GH4C1 cells and human α7 NNR in *Xenopus* oocytes.

The GH4C1 cells expressing the rat α7 NNR were prepared as described by Placzek et al., *Mol. Pharm.* 68(6): 1863-1876 (2005), incorporated by reference. Electrophysiological measurements of agonist activity were achieved using the Dynaflow rapid perfusion system and patch clamp using this GH4C1 cell expression system. Both acetylcholine and nicotine produced concentration-dependent activation of the α7 mediated current. Agonist EC$_{50}$ values from literature were comparable to those obtained using this method (see Dunlop et al. *Biochem Pharmacol in press* (2007) and Dynaflow online materials (www.cellectricon.cam), each incorporated by reference with regard to such method).

Whole-cell currents recorded with an Axopatch 700A amplifier were filtered at 1 kHz and sampled at 5 kHz by a PCI card (National Instrument). Compared with previous studies the saline solutions were modified as indicated to increase the current stability. Cells were recorded at room temperature in the following extracellular medium: 130 mM NaCl, 5 mM KCl, 2 mM CaCl$_2$, 2 mM MgCl$_2$, 10 mM HEPES, adjusted to pH 7.4 with aqueous NaOH. Borosilicate electrodes (3-5 MΩ) were filled with the following medium: 130 mM TRIS phosphate, 5 mM NaCl, 2 mM MgCl$_2$, 10 mM HEPES, 10 mM EGTA, adjusted to pH 7.4 with aqueous KOH (see Wu et al., *J. Physiol.* 576: 103-118 (2006), incorporated by reference with regard to such teaching). Under these conditions, the macro-current activity obtained with NNR whole-cell recording lasts up to 60 min when elicited with a 1000 μM acetylcholine (ACh) concentration.

Cell handling procedures were adopted from Cellectricon application notes for Dynaflow. Briefly, after removal from the incubator, cells were washed thoroughly three times with recording medium and placed on the stage of a inverted Zeiss microscope. On average 5 min was necessary before the whole-cell recording configuration was established. To avoid modification of the cell conditions, a single cell was recorded per single load of cells into Dynaflow silicon chip. No differences in the fraction of responsive cells could be detected among experimental conditions. More than 95% of the cells responded to ACh, and every cell presenting a measurable current was taken into account. Cells were held at −60 mV throughout the experiment. All test article solutions were prepared daily from stock solutions. Fresh acetylcholine (ACh) stock solution was made daily in Ringer's solution and diluted. Dose response curves were described by single Hill equations using Prism 5.0 software.

*Xenopus* oocytes expressing human α7 NNR were prepared as described by Papke and Papke, *Brit. J. Pharmacol.* 137: 49-61 (2002), incorporated by reference. Mature (>9 cm) female *Xenopus laevis* African toads (Nasco, Ft. Atkinson, Wis.) were used as a source of oocytes. Prior to surgery, the toads were anesthetized by placing the animal in a 1.5 g/L solution of 3-aminobenzoic acid ethyl ester for 30 min. Oocytes were removed from an incision made in the abdomen.

In order to remove the follicular cell layer, harvested oocytes were treated with 1.25 mg/mL collagenase from Worthington Biochemical Corporation (Freehold, N.J.) for 2 hours at room temperature in calcium-free Barth's solution (88 mM NaCl, 1 mM KCl, 15 mM HEPES pH 7.6, 0.81 mM MgSO$_4$, 2.38 mM NaHCO$_3$, 0.1 mg/mL gentamicin sulfate). Subsequently, stage 5 oocytes were isolated and injected with 50 mL (5-20 ng) each of the human α7 cRNA. Recordings were made 2 to 7 days after injection. Fresh acetylcholine (ACh) stock solutions were made daily in Ringer's solution.

Experiments were conducted using OpusXpress 6000A (Axon Instruments, Union City Calif.). OpusXpress is an integrated system that provides automated impalement and voltage clamp of up to eight oocytes in parallel. Both the voltage and current electrodes were filled with 3 M KCl. Cells were voltage-clamped at a holding potential of −60 mV. Data were collected at 50 Hz and filtered at 20 Hz. Cells were bath-perfused with Ringer's solution, and agonist solutions were delivered from a 96-well plate via disposable tips, which eliminated any possibility of cross-contamination. Flow rates were set at 2 mL/min. Drug applications alternated between ACh controls and experimental agonists. Applications were 12 seconds in duration followed by 181 second washout periods.

Responses were calculated as net charge (see Papke and Papke, Brit. J. Pharmacol. 137: 49-61 (2002), as cited above) for α7 receptors. Each oocyte received an initial control application of ACh, then an experimental drug application, and then a follow-up control application of ACh (300 μM). Responses to experimental drug applications were calculated relative to the preceding ACh control responses in order to normalize the data, compensating for the varying levels of channel expression among the oocytes. Note that 300 μM ACh evoked maximal net charge responses from α7 receptors so that normalization to the ACh controls effectively normalized the data to ACh maximum responses. Means and standard errors (SEM) were calculated from the normalized responses of at least four oocytes for each experimental concentration. For concentration-response relations, data derived from net charge analyses were plotted using Kaleidagraph 3.0.2 (Abelbeck Software; Reading, Pa.), and curves were generated from the Hill equation.

Behavioral characterization of Compound A was conducted according to the following protocols. The object recognition (OR) task was performed in accord with the description of Ennaceur and Delacour *Behav. Brain Res.* 100: 85-92 (1988), incorporated by reference. The radial arm maze (RAM) paradigm was performed in accord with the description of Levin et al., *Behav. Pharm.* 10: 675-680 (1999), incorporated by reference. The pre-pulse inhibition (PPI) assay was performed in accord with the description of Suemaru et al., *Brit. J. Pharmacol.* 142(5): 843-850 (2004). The reversal of apomorphine-induced locomotor activity (APO LOCO) assay was performed in accord with the description of Roux et al., *Curr. Protocols in Pharmacol. Unit* 5.17 (1999).

Summary of In Vitro Biological Activity

Compound A competitively inhibits the binding of radiolabeled MLA to rat brain hippocampus α7 NNRs with an equilibrium constant (Ki) values of ~1 nM, indicating that it has a very high affinity for the α7 NNR subtype. The stereoisomers of Compound A have the following Ki values at rat α7 NNRs: 2R,3S (42 nM) [previously reported as 28 nM]; 2R,3R (1 nM); 2S,3S (25 μM) (see FIG. 1A). As illustrated in FIG. 1A.2, Compound A, the 2S,3R enantiomer, demonstrates an activity at the α7 subtype in contrast to its three enantiomeric analogs, which are represented as overlapping points with weak activity. Compound A does not bind to α4β2 NNRs with any significant affinity (Ki values>2 μM).

The functional activity of (2S,3R)—N-(2-((3-pyridinyl)methyl)-1-azabicyclo[2.2.2]oct-3-yl)benzofuran-2-carboxamide or a pharmaceutically acceptable salt thereof (Compound A) and its stereoisomers was examined using patch clamp electrophysiological techniques with rat α7 NNRs stably expressed in GH4C1 (mammalian) cells. In these experiments, Compound A produced a remarkably different functional profile in comparison to the other individual isomers and to the racemic mixture of all four isomers. As can be seen in FIGS. 1A and 1B, Compound A is much more potent and efficacious at eliciting functional response ($E_{max}$=93% relative to acetylcholine (ACh); $EC_{50}$=14 nM) than any of the other isomers or the mixture of four isomers. Indeed, Compound A (the 2S,3R isomer) is the only isomer of N-(2-((3-pyridinyl)methyl)-1-azabicyclo[2.2.2]oct-3-yl)benzofuran-2-carboxamide that is able to provide potent agonism throughout the concentration range of 1-50 nM, with 10 nM being associated with in vivo activity as herein described, as shown in FIG. 1B.

The functional activity of Compound A was also electrophysiologically evaluated in *Xenopus* oocytes transiently expressing human α7 NNRs. In this system, Compound A has an $EC_{50}$ value of 33 nM and an E. of 100% of ACh response. There were decreases in subsequent control responses to ACh following the application of (2S,3R)—N-(2-((3-pyridinyl)methyl)-1-azabicyclo[2.2.2]oct-3-yl)benzofuran-2-carboxamide at concentrations greater than 100 nM ($IC_{50}$=200 nM). In contrast to previously described α7 full agonists (see Astles et al., *Current Drug Targets CNS Neurological Disorders* 1(4): 337-348 (2002), incorporated by reference with regard to such reporting), the separation between $EC_{50}$ and $IC_{50}$ values for (2S,3R)—N-(2-((3-pyridinyl)methyl)-1-azabicyclo[2.2.2]oct-3-yl)benzofuran-2-carboxamide indicates that concentrations which produce the half-maximal functional response of α7 lead to minimal, rather than full, residual inhibition. There was no detectable activation when (2S,3R)—N-(2-((3-pyridinyl)methyl)-1-azabicyclo[2.2.2]oct-3-yl)benzofuran-2-carboxamide was applied to oocytes expressing the human α4β2 sub-type and no significant decreases in subsequent control responses to ACh, indicating that (2S,3R)—N-(2-((3-pyridinyl)methyl)-1-azabicyclo[2.2.2]oct-3-yl)benzofuran-2-carboxamide is neither an agonist nor antagonist at α4β2.

The compounds exhibited little or no agonist activity in functional models bearing muscle-type receptors (α1β1γδ subtype in human TE671/RD clonal cells), or ganglion-type receptors (α3β4 subtype in the Shooter subclone of rat pheochromocytoma PC12 cells and in human SHSY-5Y clonal cells), generating ≤10% (human muscle), ≤20% (rat ganglion) and ≤10% (human ganglion) of nicotine's response at these subtypes. These data indicate selectivity for CNS sub-types over PNS subtypes.

Due to the close sequence and structural homology between α7 and 5-hydroxytryptamine ($5HT_3$) receptors, and cross-reactivity to these 2 receptors observed with other nicotinic ligands, the affinity of Compound A to $5HT_3$ receptors was investigated. Compound A (10 μM) displayed 59% inhibition of radioligand binding at the mouse $5HT_3$ receptor and 25% inhibition at the human receptor. Investigation of functional activation at the human $5HT_3$ receptor suggests minimal to no activation (i.e., a maximal response of 15% activation was obtained at 100 μM).

Muscarinic receptors are another area of concern due to interactions that have been observed with other nicotinic ligands. Compound A displayed minimal to no interaction when examined in competitive binding inhibition assays for M1, M2, nonselective central and nonselective peripheral muscarinic receptors.

The data show that Compound A is selective for α7 NNR ligands. Compound A does not bind well at those subtypes of the nicotinic receptor that are characteristic of the peripheral nervous system or at muscarinic or $5HT_3$ serotinergic receptors. Thus, Compound A possesses therapeutic potential in treating central nervous system disorders without producing side effects associated with interaction with the peripheral nervous system.

Summary of In Vivo Biological Activity

Figure 3:
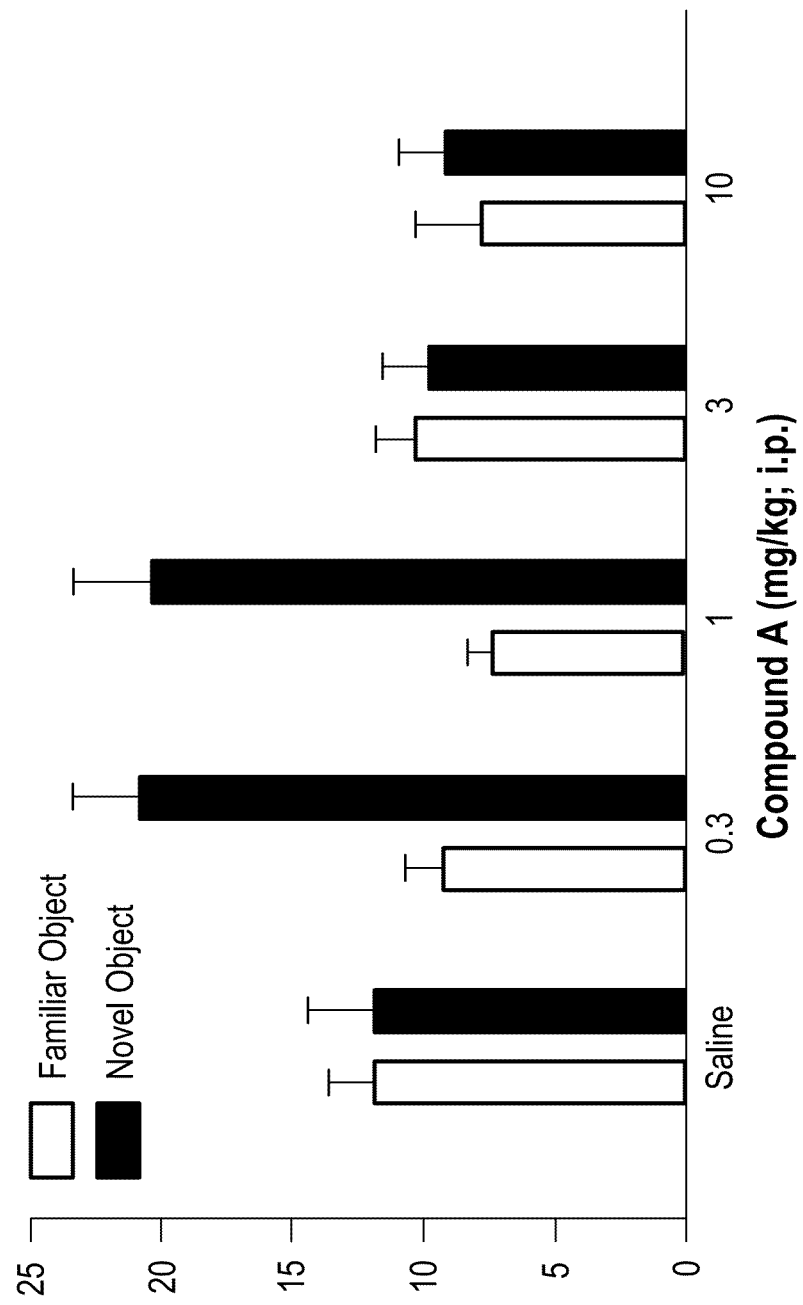
FIG. 3 illustrates an assessment of cognitive effects in an object recognition (OR) paradigm, demonstrating that (2S,3R)—N-(2-((3-pyridinyl)methyl)-1-azabicyclo [2.2.2]oct-3-yl)benzofuran-2-carboxamide has positive effects at 0.3 and 1 mg/kg administered i.p., *p<0.5.
Figure 4:
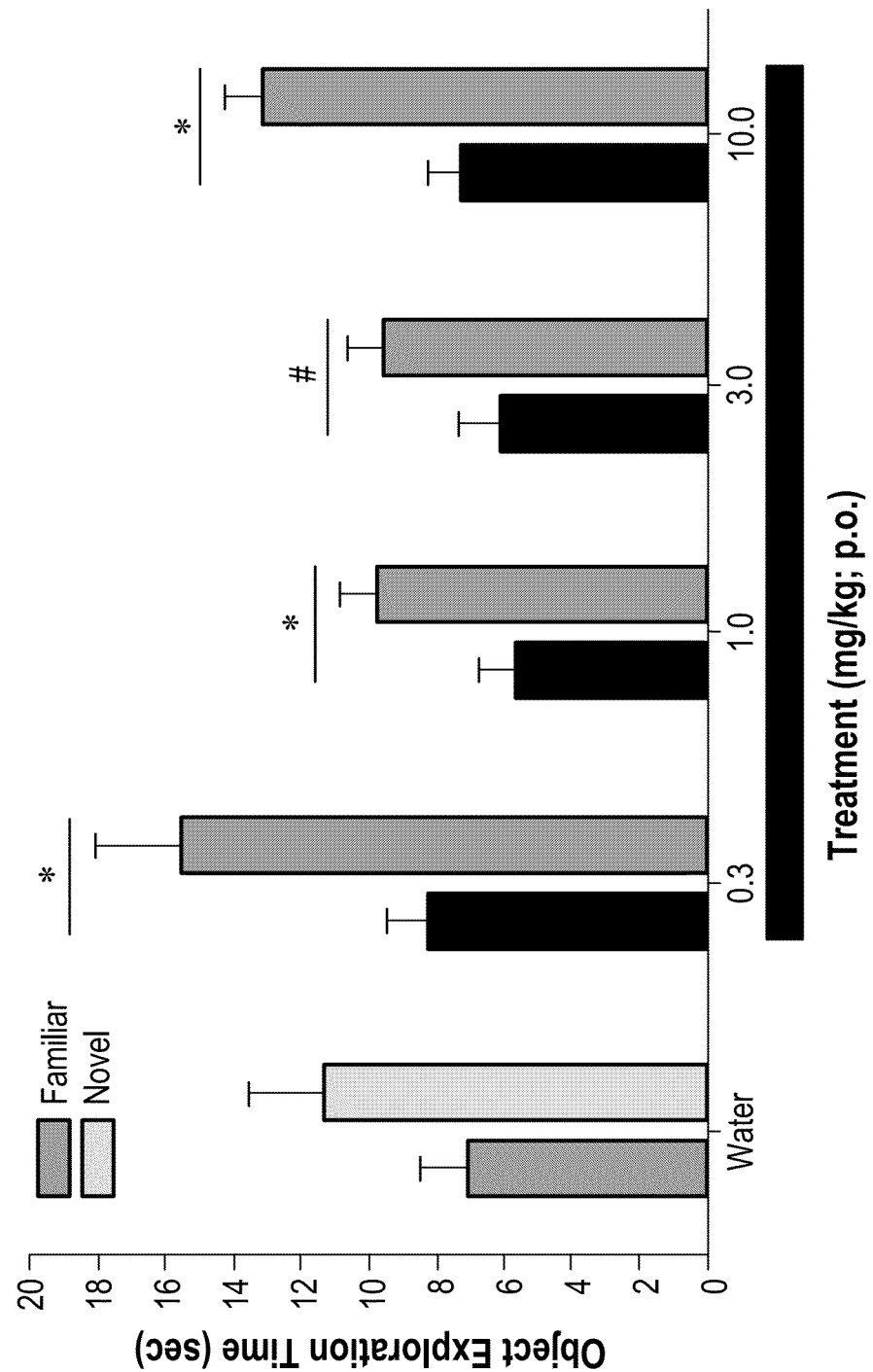
Figure 5B:
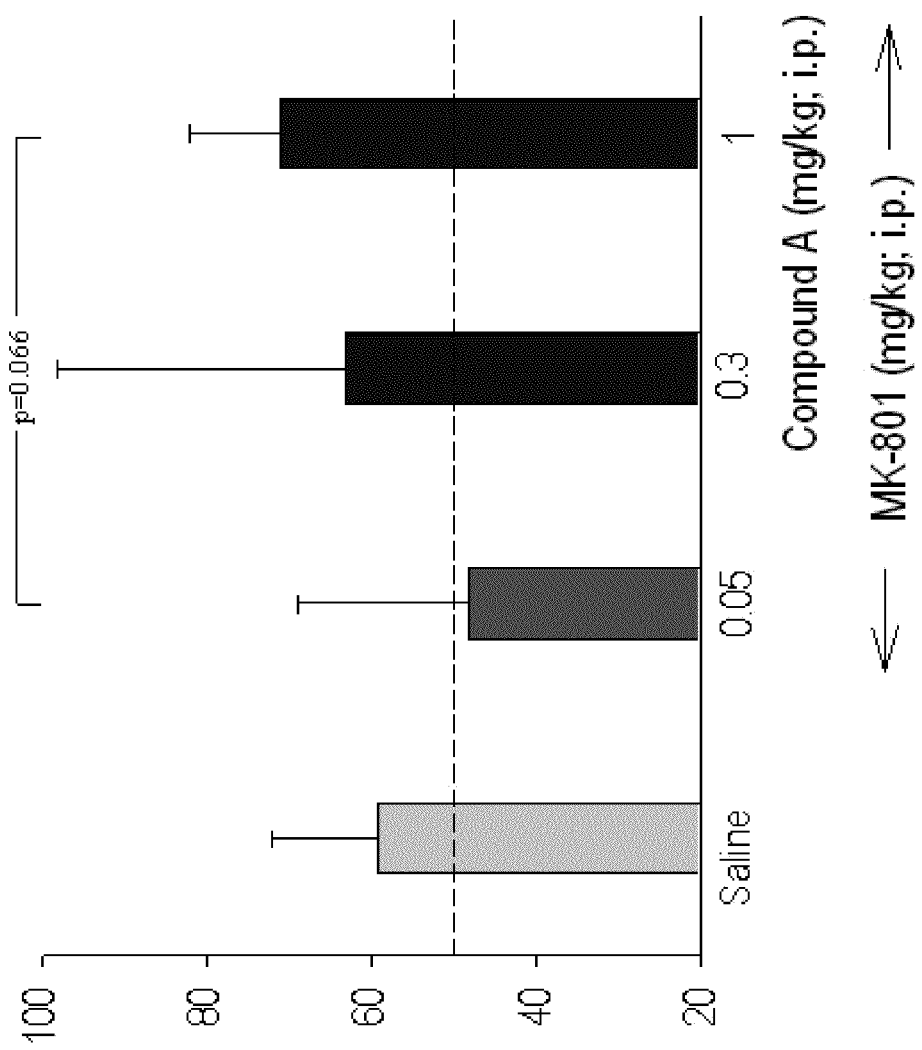
Figure 6:
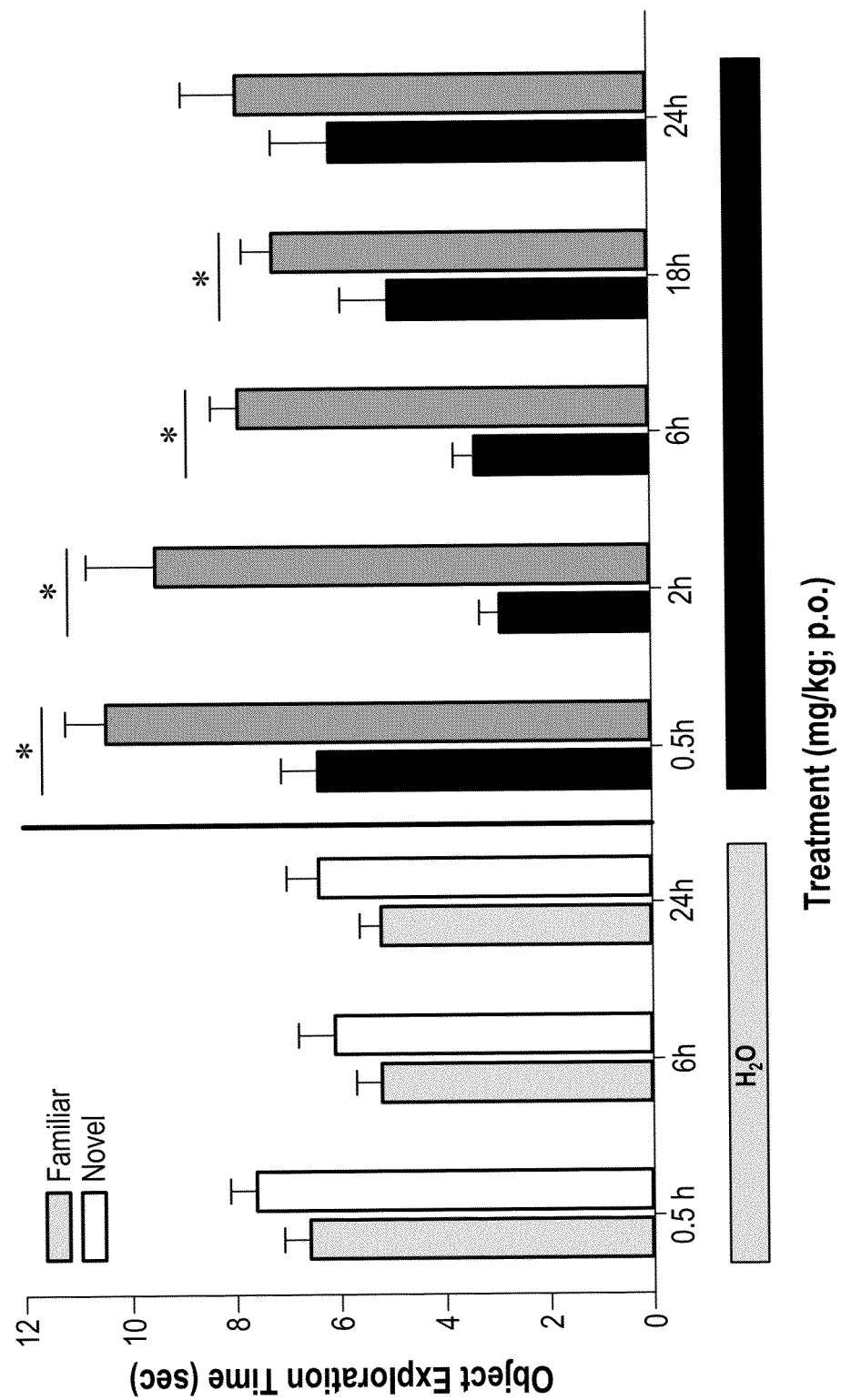
FIG. 6 illustrates that an average time spent on object A versus object B, in OR task, by the vehicle-treated group at 30 min, 6 h, or 24 h after the final sub-acute administration (p.o.) trial was not significantly different (p=0.17, p=0.35 and p=0.12, respectively). Alternatively, at 30 min, 2 h, 6 h, and 18 h after the final sub-acute administration of 0.3 mg/kg (2S,3R)—N-(2-((3-pyridinyl)methyl)-1-azabicyclo [2.2.2]oct-3-yl)benzofuran-2-carboxamide, subjects spend significantly (P<0.05) more time investigating object B (novel) than object A (familiar). Moreover, at 2 h (75%) and 6 h (71%) the recognition index was significantly improved in animals treated with 0.3 mg/kg (2S,3R)—N-(2-((3-pyridinyl)methyl)-1-azabicyclo [2.2.2]oct-3-yl)benzofuran-2-carboxamide compared to the recognition index (54%) of the vehicle-treated group at 30 minutes after final administration.
Figure 7:
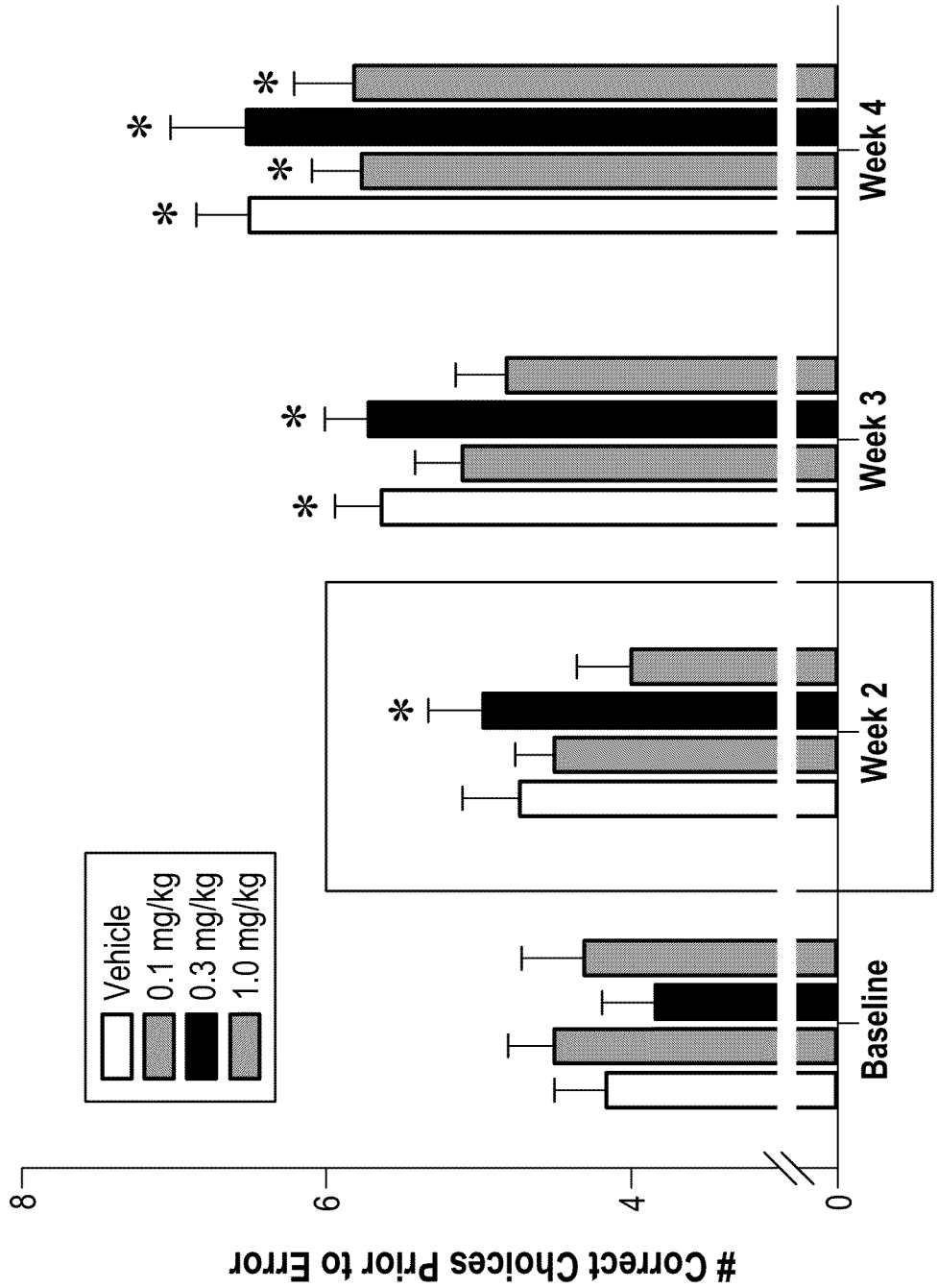
FIG. 7 illustrates an assessment of cognitive effects in a radial arm maze (RAM) paradigm. (2S,3R)—N-(2-((3-Pyridinyl)methyl)-1-azabicyclo [2.2.2]oct-3-yl)benzofuran-2-carboxamide (0.1, 0.3 and 1.0 mg/kg) was administered p.o. 30 minutes prior to the daily session. An improvement in performance on the task was evident in the group treated with 0.3 mg/kg (2S,3R)—N-(2-((3-pyridinyl)methyl)-1-azabicyclo [2.2.2]oct-3-yl)benzofuran-2-carboxamide during the second week of administration.

Compound A, (2S,3R)—N-(2-((3-pyridinyl)methyl)-1-azabicyclo[2.2.2]oct-3-yl)benzofuran-2-carboxamide or a pharmaceutically acceptable salt thereof, displays significant efficacy in two behavioral models of cognition. Compound A demonstrated potent activity in the object recognition paradigm in rats, following both i.p. (intraperitoneal, FIG. 3) and p.o. (oral, FIG. 4) administration, and also demonstrated activity across a wide dose range following oral administration (FIG. 4). Administered intraperitoneally at the same low doses (0.3 and 1 mg/kg) Compound A tends to reverse MK-801 induced deficits in the OR task (FIGS. 5A and 5B), and administered orally at 0.3 mg/kg Compound A's cognitive effects last for at least 18 hours (FIG. 6). In the radial arm maze (RAM) (FIG. 7) paradigm examining working memory, Compound A significantly increased the number of correct choices prior to error. These results show potential for (2S,3R)—N-(2-((3-pyridinyl)methyl)-1-azabicyclo[2.2.2]oct-3-yl)benzofuran-2-carboxamide in treating cognitive deficits and dysfunctions associated with schizophrenia, including those of working memory.

Figure 8:
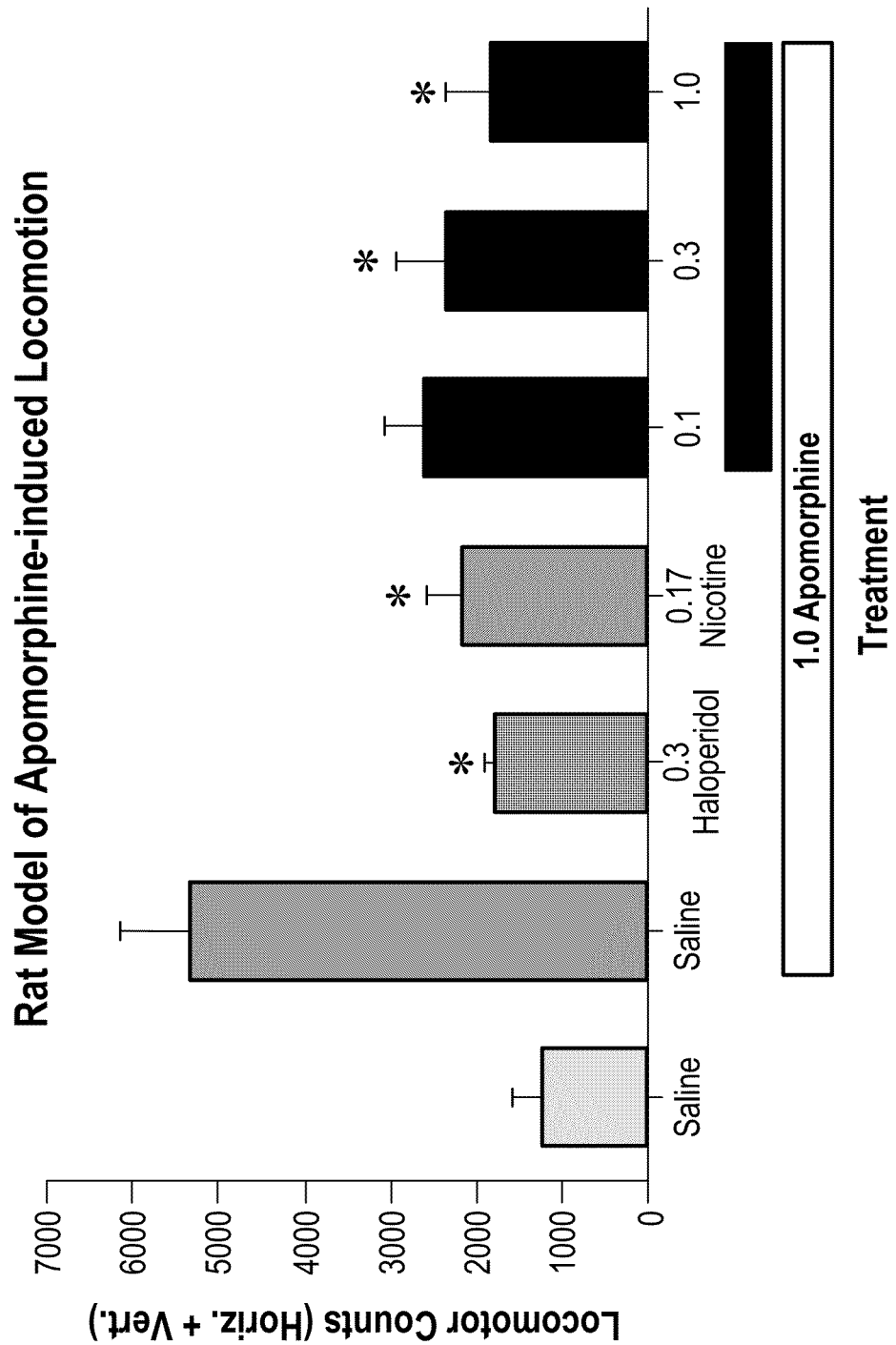
FIG. 8 illustrates a study of antipsychotic effects, measured as hyperactivity behavior induced by dopamine over-stimulation, showing that (2S,3R)—N-(2-((3-pyridinyl)methyl)-1-azabicyclo [2.2.2]oct-3-yl)benzofuran-2-carboxamide (0.3 and 1.0 mg/kg; s.c.) attenuates locomotor hyperactivity induced by apomorphine (1.0 mg/kg) following subcutaneous administration in rats.

For a compound to be useful for treating the cognitive dysfunction in schizophrenia, it must not diminish the effects of classical or atypical antipsychotics against the positive symptoms of schizophrenia. Thus, it is compelling that, in addition to its cognitive enhancing properties, Compound A also displays effectiveness in reversing apomorphine-induced locomotor activity (APO LOCO) (FIG. 8) and prepulse inhibition (PPI) (FIG. 9) models of positive symptoms of schizophrenia. Thus, (2S,3R)—N-(2-((3-pyridinyl)methyl)-1-azabicyclo[2.2.2]oct-3-yl)benzofuran-2-carboxamide would be expected to provide an additional benefit against the positive, as well as the cognitive, symptoms associated with schizophrenia.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A method for treating one or more of mild cognitive impairment, age-associated memory impairment, pre-senile dementia, early onset Alzheimer's disease, senile dementia, dementia of the Alzheimer's type, or Alzheimer's disease comprising administering to a subject in need thereof a therapeutically effective amount of a compound (2S,3R)—N-(2-((3-pyridinyl)methyl)-1-azabicyclo[2.2.2]oct-3-yl)benzofuran-2-carboxamide or a pharmaceutically acceptable salt thereof, substantially free of (2S,3S)—N-(2-((3-pyridinyl)methyl)-1-azabicyclo[2.2.2]oct-3-yl)benzofuran-2-carboxamide, (2R,3S)—N-(2-((3-pyridinyl)methyl)-1-azabicyclo

[2.2.2]oct-3-yl)benzofuran-2-carboxamide, (2R,3R)—N-(2-((3-pyridinyl)methyl)-1-azabicyclo[2.2.2]oct-3-yl)benzofuran-2-carboxamide, and pharmaceutically acceptable salts thereof.

2. The method of claim 1, wherein the treatment is for Alzheimer's disease.

3. The method of claim 1, wherein the treatment is for early onset Alzheimer's disease.

* * * * *